(12) United States Patent
Curran

(10) Patent No.: US 10,294,534 B2
(45) Date of Patent: May 21, 2019

(54) RESPIRATORY INFECTION ASSAY

(71) Applicant: THE SECRETARY OF STATE FOR HEALTH, Whitehall, London (GB)

(72) Inventor: Martin Curran, Sailsbury (GB)

(73) Assignee: THE SECRETARY OF STATE FOR HEALTH, London (GB)

( * ) Notice: Subject to any disclaimer, the term of this patent is extended or adjusted under 35 U.S.C. 154(b) by 82 days.

(21) Appl. No.: 14/363,533

(22) PCT Filed: Dec. 10, 2012

(86) PCT No.: PCT/GB2012/053076
§ 371 (c)(1),
(2) Date: Jun. 6, 2014

(87) PCT Pub. No.: WO2013/084010
PCT Pub. Date: Jun. 13, 2013

(65) Prior Publication Data
US 2015/0099261 A1    Apr. 9, 2015

(30) Foreign Application Priority Data
Dec. 9, 2011   (GB) .................................. 1121210.7

(51) Int. Cl.
C12Q 1/68      (2018.01)
C12P 19/34     (2006.01)
C12Q 1/70      (2006.01)

(52) U.S. Cl.
CPC .............. *C12Q 1/701* (2013.01); *C12Q 1/70* (2013.01)

(58) Field of Classification Search
CPC ..... C12Q 1/70; C12Q 2561/113; C12Q 1/701
See application file for complete search history.

(56) References Cited

U.S. PATENT DOCUMENTS

| | | | |
|---|---|---|---|
| 2001/0053519 A1* | 12/2001 | Fodor | B01J 19/0046 435/6.11 |
| 2005/0136395 A1 | 6/2005 | Mittmann et al. | |
| 2005/0202414 A1 | 9/2005 | Jia et al. | |
| 2006/0003352 A1 | 1/2006 | Lipkin et al. | |
| 2006/0177849 A1 | 8/2006 | Oh et al. | |
| 2006/0257860 A1 | 11/2006 | Marlowe et al. | |
| 2007/0092871 A1 | 4/2007 | Lodes et al. | |
| 2010/0086908 A1 | 4/2010 | Prudent et al. | |
| 2010/0105025 A1 | 4/2010 | Engelhard | |
| 2010/0279273 A1 | 11/2010 | Bergeron et al. | |
| 2013/0023443 A1 | 1/2013 | Shirai et al. | |

FOREIGN PATENT DOCUMENTS

| | | | |
|---|---|---|---|
| CN | 101985664 A * | 3/2011 | |
| CN | 102031314 | 4/2011 | |
| EP | 1837403 A2 | 9/2007 | |
| EP | 2 077 337 | 7/2009 | |
| JP | 2006-180878 A | 7/2006 | |
| JP | 2009-523451 A | 6/2009 | |
| JP | 2010-178687 | 8/2010 | |
| WO | 00/17391 A1 | 3/2000 | |
| WO | 2004/045365 A2 | 6/2004 | |
| WO | 2004/057021 A2 | 7/2004 | |
| WO | 2005/005658 A1 | 1/2005 | |
| WO | 2005/038427 A2 | 4/2005 | |
| WO | WO 2005061698 A1 * | 7/2005 | ............. A61K 35/76 |
| WO | 2005/118885 A2 | 12/2005 | |
| WO | 2008/042450 A2 | 4/2008 | |
| WO | WO 2008/054830 | 5/2008 | |
| WO | 2008/140513 A1 | 11/2008 | |
| WO | 2011/122034 A1 | 10/2011 | |

OTHER PUBLICATIONS

Ellis J.S. et al. Diagnostic Virology Protocols, vol. 665 of the series Methods in Molecular Biology pp. 161-181.*
Kodani, M.J. et al. Journal of Clinical Microbiology, Jun. 2011, p. 2175-2182.*
Altschul et al., "Optimal Sequence Alignment Using Affine Gap Costs," Bulletin of Mathematical Biology, 48 (5/6):603-616 (1986).
Brittain-Long et al., "Multiplex Real-time PCR for Detection of Respiratory Tract Infections," Journal of Clinical Virology, 41:53-56 (2008).
Depiereux et al., "Match-Box: A Fundamentally New Algorithm for the Simultaneous Alignment of Several Protein Sequences," 8(5):501-509 (1992).
Goth, "Significant Improvement in Accuracy of Multiple Protein Sequence Alignments by Iterative Refinement as Assessed by Reference to Structural Alignments," J. Mol. Biol., 264:823-838 (1996).
Henikoff et al., "Amino Acid Substitution Matrices from Protein Blocks," Proc. Natl. Acad. Sci. USA, 89:10915-10919 (Nov. 1992).
Lawrence et al., "Detecting Subtle Sequence Signals: A Gibbs Sampling Strategy for Multiple Alignment," Science, 262:208-214 (Oct. 8, 1993).
Murray et al., "Mortality by Cause for Eight Regions of the World: Global Burden of Disease Study," The Lancet, 349:1269-1276 (May 3, 1997).
Smith, "Adventures with Multiplex Real-time PCR", Biocompare Buyers Guide for Life Scientists, retrieved from http://www.biocompare.com/Articles/FeaturedArticle/1146/Adventures-with-Multipl . . . (Oct. 18, 2010) XP-007915436.
Thompson et al., "Clustal W: Improving the Sensitivity of Progressive Multiple Sequence Alignment through Sequence Weighting, Position-specific Gap Penalties and Weight Matrix Choice," Nucleic Acids Research, 22 (22):4673-4680 (1994).
Van Walle et al., "Align-m—A New Algorithm for Multiple Alignment of Highly Divergent Sequences," Bioinformatics, 20(9):1428-1435 (2004).
International Search Report and Written Opinion for International Application. No. PCT/GB2012/053076 dated Mar. 3, 2013. (16 pages).
Brittain-Long et al. "Muliplex real-time PCR for detection of respiratory tract infections." *J. of Clin. Virol.* vol. 41. 2008. pp. 53-56.

(Continued)

Primary Examiner — Stephen T Kapushoc
(74) Attorney, Agent, or Firm — Merchant & Gould P.C.

(57) ABSTRACT

The present invention provides nucleic acid products and corresponding methods for screening a biological sample for the presence of a respiratory infection-causing microorganism.

18 Claims, 1 Drawing Sheet

Specification includes a Sequence Listing.

(56) References Cited

OTHER PUBLICATIONS

Smith. "Adventrues with Multiplex Real-Time PCR." Retrieved from: http://www.biocompare.com/Articles/FeaturedArticle/1146/Adventures-with-Multiplex-Real-time-PCR.html. 2010.

Creer et al. (2006) "Aetiological role of viral and bacterial infections in acute adult lower respiratory tract infection (LRTI) in primary care" Thorax 61: 75-79.

Brittain-Long et al. (2008) "Multiplex real-time PCR for detection of respiratory tract infections" Journal of Clinical Virology 41: 53-36.

Tang et al. (1999) "A colorimetric microtiter plate PCR system detects respiratory syncytial virus in nasal aspirates and discriminates subtypes A and B" Diagn Microbiol Infect Dis 34: 333-337.

White et al., "Development of a Generic Real-time PCR Assay for Simultaneous Detection of Proviral DNA of Simian Betaretrovirus Serotypes 1, 2, 3, 4 and 5 and Secondary Uniplex Assays for Specific Serotype Identification", J. Virol. Methods. 162 (1-2): 148-154 (2009).

* cited by examiner

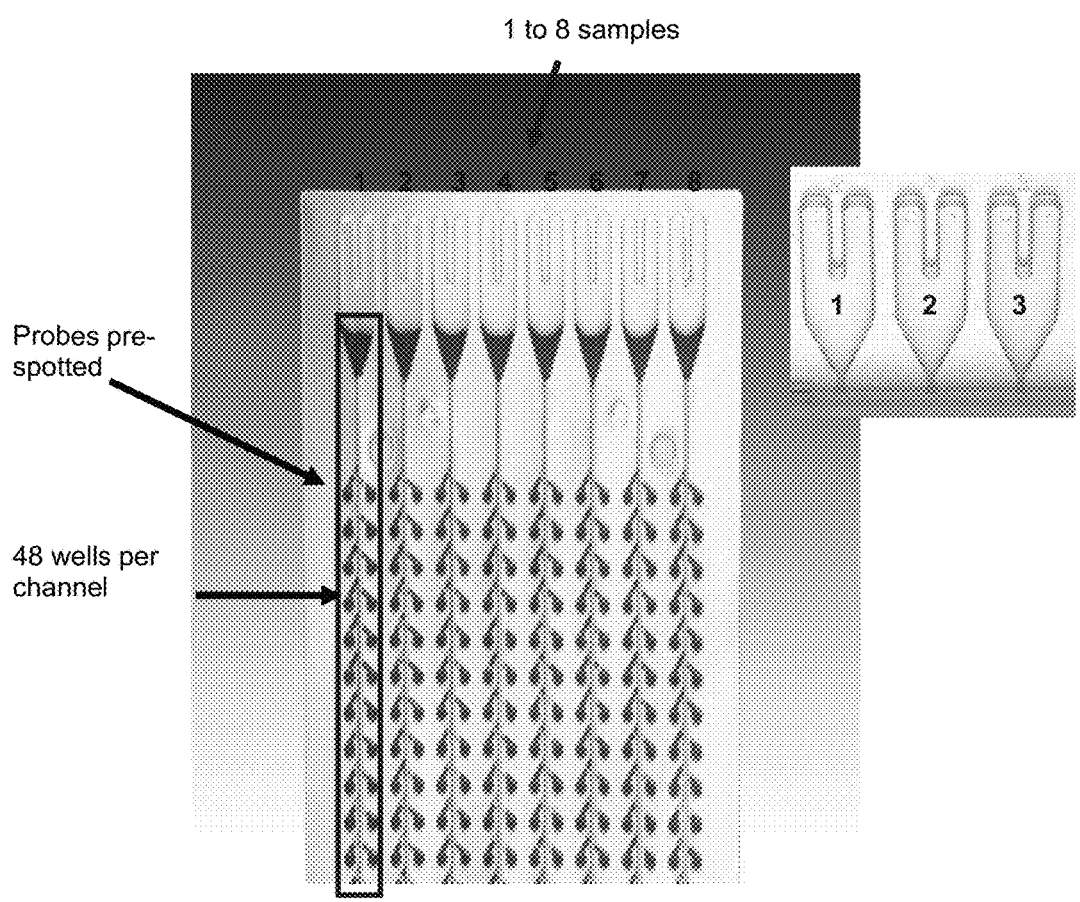

RESPIRATORY INFECTION ASSAY

This application is a National Stage Application of PCT/GB2012/053076, filed 10 Dec. 2012, which claims benefit of Serial No. 1121210.7, filed 9 Dec. 2011 in Great Britain and which applications are incorporated herein by reference. To the extent appropriate, a claim of priority is made to each of the above disclosed applications.

The present invention relates to nucleic acid products and to corresponding methods for screening a biological sample for the presence of a respiratory infection-causing microorganism.

Respiratory infections are among the most common causes of human disease worldwide (see Murray and Lopez (1997)—Lancet, 349, pages 1269-1276). Compromised individuals (cardiac, pulmonary, immune systems), the elderly and infants are especially at risk of developing serious complications. Historically, rapid laboratory diagnosis of respiratory infections has been performed via a suite of multiplexed Real-Time (RT) PCR Taqman assays. However, a significant problem associated with this multiplexed approach is the need to prepare, run and monitor parallel screening assays. This represents an undesirable financial burden as each assay performed leads to a doubling of consumable costs vis-a-vis a single assay and places additional operating burden in terms of wear and tear on the expensive equipment employed to perform these assays. Said multiplexed approach also imposes an additional time and manpower burden associated with performance of the multiple assays.

There is therefore a need for a more efficient screening system.

The present invention solves one or more of the above-identified problems by providing a simple, one-step assay (i.e. a singleplex format) for detecting the presence or absence of multiple respiratory infection-causing microorganisms in a single isolated sample.

In more detail, the present invention provides a method for detecting the presence of one or more of at least six respiratory infection-causing microorganisms in a sample or detecting the absence of said microorganisms in said sample, said method comprising:

A) applying a sample to a test card, wherein said test card comprises six discrete wells:
  1) a first well that includes a first probe, wherein the first probe has a nucleic acid sequence that comprises a nucleic acid sequence having at least 80% sequence identity to the nucleic acid sequence GGCAATGCWG (SEQ ID NO: 1);
  2) a second well that includes a second probe, wherein the second probe has a nucleic acid sequence that comprises a nucleic acid sequence having at least 80% sequence identity to the nucleic acid sequence GAYGGGACCR (SEQ ID NO: 2);
  3) a third well that includes a third probe, wherein the third probe has a nucleic acid sequence that comprises a nucleic acid sequence having at least 80% sequence identity to the nucleic acid sequence CACCAGACAC (SEQ ID NO: 3);
  4) a fourth well that includes a fourth probe, wherein the fourth probe has a nucleic acid sequence that comprises a nucleic acid sequence having at least 80% sequence identity to the nucleic acid sequence GGTCATTGGR (SEQ ID NO: 4);
  5) a fifth well that includes a fifth probe, wherein the fifth probe has a nucleic acid sequence that comprises a nucleic acid sequence having at least 80% sequence identity to the nucleic acid sequence CACTGGGCAC (SEQ ID NO: 5);
  6) a sixth well that includes a sixth probe, wherein the sixth probe has a nucleic acid sequence that comprises a nucleic acid sequence having at least 80% sequence identity to the nucleic acid sequence RGTGTTCATT (SEQ ID NO: 6);

B) allowing nucleic acid present in the sample to contact with the probes within said wells;
C) detecting for the presence of bound nucleic acid complex in which sample nucleic acid has bound to one or more of said probes;
D) wherein the presence of bound nucleic acid complex confirms that nucleic acid from one or more of said six respiratory infection-causing microorganisms is present within the sample, and wherein the absence of bound nucleic acid complex confirms that nucleic acid from all of said six respiratory infection-causing microorganisms is absent within the sample.

One key prior art problem that has been addressed by Applicant is the provision of a robust set of probes that are mutually compatible (i.e. retain accurate binding specificity) within a single set of assay conditions (i.e. a singleplex format). One particular advantage associated with the method of the present invention is speed. By way of example, the method of the invention is typically completed within 2.5 hours, preferably within 2 or 1.5 hours. In contrast, existing multiplex assays typically take at least 4-5 hours, typically at least 5 hours.

Another advantage associated with the uniplex (aka singleplex) assay method of the present invention is an increased sensitivity, which enables quantitative detection of microorganisms (for example, viral and/or bacterial load) in the sample, in addition to simply determining the presence or absence of a particular pathogen in the sample.

Microorganisms (for example, viruses and bacteria) in the sample can be subjected to load calibration for each microorganism target. This enables the quantification of specific load of each microorganism in the sample. Advantageously, this feature of the present invention allows the determination of the predominant microorganism(s) in samples where multiple microorganisms are present. For example, the uniplex assay method of the invention permits one to ascertain the predominant virus in samples where multiple viruses are present. In addition, the method of the invention allows for the quantitative detection of viruses in samples over time, which is particularly useful when there is fluctuation in viral load of specific viruses.

Moreover, while existing systems employ hybridisation performed on a membrane, the assay method of the present invention is carried out in a closed (e.g. sterile) system, thus reducing the likelihood of contamination, which provides another advantage.

Probes 1-6 respectively permit sensitive detection of:
  1) Respiratory syncytial virus (RSV A & B);
  2) Rhinoviruses;
  3) Human Metapneumovirus (hMPV);
  4) Influenza B (Flu B Quad);
  5) Influenza A (Flu A CDC DC); and
  6) Influenza A subtype H5 (H5 FRET)

Thus, the above-defined method provides a rapid assay for the detection of any one or more of said respiratory infection-causing microorganisms in a uniplex (aka single-plex) assay format. Similarly, said method provides a rapid assay for the confirmation that all of said respiratory infection-causing microorganisms are absent from a sample in a single (uniplex) assay. A uniplex assay means that each of the multiple individual detection well assays is performed under the same assay conditions and/or substantially at the same time. In use, a single sample is applied to the test card, which sample is then populated into each test well.

In one embodiment, the method employs a test card comprising one or more additional wells and corresponding one or more additional probes selected from:
7) a seventh well that includes a seventh probe, wherein the seventh probe has a nucleic acid sequence that comprises a nucleic acid sequence having at least 80% sequence identity to the nucleic acid sequence TTTCAGGGG (SEQ ID NO: 7);
8) an eighth well that includes an eighth probe, wherein the eighth probe has a nucleic acid sequence that comprises a nucleic acid sequence having at least 80% sequence identity to the nucleic acid sequence CCGCAAGTCA (SEQ ID NO: 8);
9) a ninth well that includes a ninth probe, wherein the ninth probe has a nucleic acid sequence that comprises a nucleic acid sequence having at least 80% sequence identity to the nucleic acid sequence TTGCCTGGTG (SEQ ID NO: 9);
10) a tenth well that includes a tenth probe, wherein the tenth probe has a nucleic acid sequence that comprises a nucleic acid sequence having at least 80% sequence identity to the nucleic acid sequence TAARGTAGGT (SEQ ID NO: 10);
11) an eleventh well that includes an eleventh probe, wherein the eleventh probe has a nucleic acid sequence that comprises a nucleic acid sequence having at least 80% sequence identity to the nucleic acid sequence CGGCRTCATY (SEQ ID NO: 11);
12) a twelfth well that includes a twelfth probe, wherein the twelfth probe has a nucleic acid sequence that comprises a nucleic acid sequence having at least 80% sequence identity to the nucleic acid sequence ATARTGRTAA (SEQ ID NO: 12);
13) a thirteenth well that includes a thirteenth probe, wherein the thirteenth probe has a nucleic acid sequence that comprises a nucleic acid sequence having at least 80% sequence identity to the nucleic acid sequence ATAGTAATAA (SEQ ID NO: 13); wherein the same method steps are employed as hereinbefore described.

In one embodiment, the test card may include two or more, three or more, four or more, five or more, six or more, or all seven of said seventh through to thirteenth wells (plus corresponding probes).

Probes 7-13 respectively permit sensitive detection of:
7) Human parainfluenza virus type 1 (HPIV 1);
8) Human parainfluenza virus type 2 (HPIV 2);
9) Human parainfluenza virus type 3 (HPIV 3);
10) Human parainfluenza virus type 4 (HPIV 4);
11) Human Adenoviruses #2;
12) Influenza A H1 2009 Tamiflu sensitive; and
13) Influenza A H1 2009 Tamiflu resistant.

Thus, the above-defined method provides a rapid assay for the detection of any one or more of said respiratory infection-causing microorganisms in a uniplex format assay. Similarly, said method provides a rapid assay for the confirmation that all of said respiratory infection-causing microorganisms are absent from a sample in a uniplex format assay.

In one embodiment, the method employs a test card comprising one or more additional wells and corresponding one or more additional probes selected from:
14) a fourteenth well that includes a fourteenth probe, wherein the fourteenth probe has a nucleic acid sequence that comprises a nucleic acid sequence having at least 80% sequence identity to the nucleic acid sequence TACTGTGACA (SEQ ID NO: 14);
15) a fifteenth well that includes a fifteenth probe, wherein the fifteenth probe has a nucleic acid sequence that comprises a nucleic acid sequence having at least 80% sequence identity to the nucleic acid sequence YRGCGGAACC (SEQ ID NO: 15);
16) a sixteenth well that includes a sixteenth probe, wherein the sixteenth probe has a nucleic acid sequence that comprises a nucleic acid sequence having at least 80% sequence identity to the nucleic acid sequence TAACGAGTGT (SEQ ID NO: 16);
17) a seventeenth well that includes a seventeenth probe, wherein the seventeenth probe has a nucleic acid sequence that comprises a nucleic acid sequence having at least 80% sequence identity to the nucleic acid sequence CGAATGAATG (SEQ ID NO: 17);
18) an eighteenth well that includes an eighteenth probe, wherein the eighteenth probe has a nucleic acid sequence that comprises a nucleic acid sequence having at least 80% sequence identity to the nucleic acid sequence YTCTAAGCAT (SEQ ID NO: 18),
19) a nineteenth well that includes a nineteenth probe, wherein the nineteenth probe has a nucleic acid sequence that comprises a nucleic acid sequence having at least 80% sequence identity to the nucleic acid sequence TTCTAAGCAT (SEQ ID NO: 19);
20) a twentieth well that includes a twentieth probe, wherein the twentieth probe has a nucleic acid sequence that comprises a nucleic acid sequence having at least 80% sequence identity to the nucleic acid sequence GAGTAYCTSA (SEQ ID NO: 20);
21) a twenty first well that includes a twenty first probe, wherein the twenty first probe has a nucleic acid sequence that comprises a nucleic acid sequence having at least 80% sequence identity to the nucleic acid sequence ACTGCATCCG (SEQ ID NO: 21),
22) a twenty second well that includes a twenty second probe, wherein the twenty second probe has a nucleic acid sequence that comprises a nucleic acid sequence having at least 80% sequence identity to the nucleic acid sequence TGTCACCTCT (SEQ ID NO: 22);
23) a twenty third well that includes a twenty third probe, wherein the twenty third probe has a nucleic acid sequence that comprises a nucleic acid sequence having at least 80% sequence identity to the nucleic acid sequence AGTGTGTYAC (SEQ ID NO: 23),
24) a twenty fourth well that includes a twenty fourth probe, wherein the twenty fourth probe has a nucleic acid sequence that comprises a nucleic acid sequence having at least 80% sequence identity to the nucleic acid sequence GAATTTCTGG (SEQ ID NO: 24);
25) a twenty fifth well that includes a twenty fifth probe, wherein the twenty fifth probe has a nucleic acid sequence that comprises a nucleic acid sequence having at least 80% sequence identity to the nucleic acid sequence TTGCCGGATG (SEQ ID NO: 25),
26) a twenty sixth well that includes a twenty sixth probe, wherein the twenty sixth probe has a nucleic acid sequence that comprises a nucleic acid sequence having at least 80% sequence identity to the nucleic acid sequence CAGCAACTGT (SEQ ID NO: 26);
27) a twenty seventh well that includes a twenty seventh probe, wherein the twenty seventh probe has a nucleic acid sequence that comprises a nucleic acid sequence having at least 80% sequence identity to the nucleic acid sequence TGCTCCAGAA (SEQ ID NO: 27);

28) a twenty eighth well that includes a twenty eighth probe, wherein the twenty eighth probe has a nucleic acid sequence that comprises a nucleic acid sequence having at least 80% sequence identity to the nucleic acid sequence TNGCCATTGY (SEQ ID NO: 28);

29) a twenty ninth well that includes a twenty ninth probe, wherein the twenty ninth probe has a nucleic acid sequence that comprises a nucleic acid sequence having at least 80% sequence identity to the nucleic acid sequence GTYCCGTGRA (SEQ ID NO: 29);

30) a thirtieth well that includes a thirtieth probe, wherein the thirtieth probe has a nucleic acid sequence that comprises a nucleic acid sequence having at least 80% sequence identity to the nucleic acid sequence CTGGARTCTG (SEQ ID NO: 30);

31) a thirty first well that includes a thirty first probe, wherein the thirty first probe has a nucleic acid sequence that comprises a nucleic acid sequence having at least 80% sequence identity to the nucleic acid sequence CRACTGTGTC (SEQ ID NO: 31);

32) a thirty second well that includes a thirty second probe, wherein the thirty second probe has a nucleic acid sequence that comprises a nucleic acid sequence having at least 80% sequence identity to the nucleic acid sequence GTGTCACCGC (SEQ ID NO: 32);

33) a thirty third well that includes a thirty third probe, wherein the thirty third probe has a nucleic acid sequence that comprises a nucleic acid sequence having at least 80% sequence identity to the nucleic acid sequence GAYGGRACCR (SEQ ID NO: 33);

wherein the same method steps are employed as hereinbefore described.

In one embodiment, the test card may include two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or all twenty of said fourteenth through to thirty third wells (plus corresponding probes). Said one or more fourteenth through to thirtieth wells (plus corresponding probes) may be employed in combination with or alternatively to said one or more seventh through to thirteenth wells (plus corresponding probes).

Probes 14-30 respectively permit sensitive detection of:
14) Respiratory syncytial virus (RSV #2); (RSV #3)
15) Enteroviruses;
16) Severe Acute Respiratory Syndrome coronavirus (SARS);
17) Group 2 Coronaviruses OC43 and HKU1 (GP2 OC43/HKU1);
18) Group 1 Coronavirus NL63 (GP1 NL63);
19) Group 1 Coronavirus 229E (GP1 229E);
20) Human Adenoviruses;
21) Bocavirus;
22) Influenza A (Flu A Quad);
23) Influenza A H1 2009 (H1 sw 2009);
24) Influenza A N1 2009 (N1 CFI);
25) Influenza A H1 seasonal (H1 seasonal CFI);
26) Influenza A H3 Seasonal (H3 seasonal CFI);
27) Influenza A H5 (H5 CFI);
28) Influenza A H7 (H7);
29) Influenza A H9 (H9 a);
30) Influenza A H9 (H9 b);
31) Human parainfluenza virus type 1 (HPIV 1 #2);
32) Human parainfluenza virus type 3 (HPIV 1 #3); and
33) Rhinoviruses #2.

Thus, the above-defined method provides a rapid assay for the detection of any one or more of said respiratory infection-causing microorganisms in a uniplex format assay. Similarly, said method provides a rapid assay for the confirmation that all of said respiratory infection-causing microorganisms are absent from a sample in uniplex format assay.

In one embodiment, the method employs a test card comprising one or more additional wells and corresponding one or more additional probes, wherein said additional probes bind to (and thus detect) causative agents of atypical pneumonia. Patients infected with atypical bacterial respiratory infections do not respond to conventional antibiotics, often exacerbating their condition and draining healthcare resources. Conventional laboratory identification of the organisms associated with atypical bacterial pneumonia can be difficult, slow and expensive, and the present invention therefore provided a dramatic improvement in this regard. Thus, in this embodiment, one or more additional probes are employed to detect one or more of: *Chlamydophila pneumoniae*, *Chlamydophila psittaci*, *Legionella pneumophila*, *Mycoplasma pneumonia*, and *Coxiella burnettii*. Accordingly, in one embodiment, the method of the present invention employs a test card comprising one or more additional wells and corresponding one or more additional probes selected from:

34) a thirty fourth well that includes a thirty fourth probe, wherein the thirty fourth probe has a nucleic acid sequence that comprises a nucleic acid sequence having at least 80% sequence identity to the nucleic acid sequence AATTGGCTTT (SEQ ID NO: 34), 35) a thirty fifth well that includes a thirty fifth probe, wherein the thirty fifth probe has a nucleic acid sequence that comprises a nucleic acid sequence having at least 80% sequence identity to the nucleic acid sequence GGAGAGTGTG (SEQ ID NO: 35);

36) a thirty sixth well that includes a thirty sixth probe, wherein the thirty sixth probe has a nucleic acid sequence that comprises a nucleic acid sequence having at least 80% sequence identity to the nucleic acid sequence CAGACGCTGG (SEQ ID NO: 36);

37) a thirty seventh well that includes a thirty seventh probe, wherein the thirty seventh probe has a nucleic acid sequence that comprises a nucleic acid sequence having at least 80% sequence identity to the nucleic acid sequence CGGCGTTTAT (SEQ ID NO: 37);

38) a thirty eighth well that includes a thirty eighth probe, wherein the thirty eighth probe has a nucleic acid sequence that comprises a nucleic acid sequence having at least 80% sequence identity to the nucleic acid sequence CTTGGTGTGA (SEQ ID NO: 38);

39) a thirty ninth well that includes a thirty ninth probe, wherein the thirty ninth probe has a nucleic acid sequence that comprises a nucleic acid sequence having at least 80% sequence identity to the nucleic acid sequence CTTGGTGTGA (SEQ ID NO: 39);

wherein the same method steps are employed as hereinbefore described.

In one embodiment, the test card may include two or more, three or more, four or more, five or more, or all six of said thirty fourth through to thirty ninth wells (plus corresponding probes). Said one or more thirty fourth to thirty ninth wells (plus corresponding probes) may be employed in combination with or alternatively to said fourteenth through to thirty third wells (plus corresponding probes) and/or in combination with or alternatively to said one or more seventh through to thirteenth wells (plus corresponding probes).

Probes 34-39 respectively permit sensitive detection of:
34) *Legionella pneumophilia;*
35) *Mycoplasma pneumoniae;*
36) *Chlamydiophilia pneumoniae;*
37) *Coxiella burnetti;*
38) *Chlamydiophilia psittaci*; and
39) *Chlamydiophilia abortus.*

Thus, the above-defined method provides a rapid assay for the detection of any one or more of said respiratory infection-causing microorganisms in a uniplex format assay. Similarly, said method provides a rapid assay for the confirmation that all of said respiratory infection-causing microorganisms are absent from a sample in a uniplexed format assay.

In one embodiment, the method of the present invention employs a test card comprising one or more additional 'control' wells and corresponding one or more additional 'control' probes selected from:
40) a fortieth well that includes a fortieth probe, wherein the fortieth probe has a nucleic acid sequence that comprises a nucleic acid sequence having at least 80% sequence identity to the nucleic acid sequence AGAT-CAAGGT (SEQ ID NO: 40);
41) a forty first well that includes a forty first probe, wherein the forty first probe has a nucleic acid sequence that comprises a nucleic acid sequence having at least 80% sequence identity to the nucleic acid sequence ACCTGAAGGC (SEQ ID NO: 41)

wherein the same method steps are employed as hereinbefore described.

In one embodiment, the test card may include one or both of said fortieth or forty first wells (plus corresponding probes). Alternative 'control' probe/probe targets may be employed. Said 'control' probes may be used in combination with any of the hereinbefore described embodiments.

Control probes 40-41 respectively permit sensitive detection of:
40) *Escherichia coli* Bacteriophage MS2 (MS2 IC); and
41) Human Ribonuclease P gene (RNAse P).

The presence of one or more 'control' probes allows (substantially simultaneous) confirmation that the assay is otherwise performing normally. For example, the sample is spiked with *Escherichia coli* bacteriophage MS2 (MS2 IC) prior to nucleic acid extraction. Detection of bacteriophage MS2 nucleic acid in the sample using bacteriophage MS2 probe allows confirmation of the various stages involved in the uniplex assay being completed successfully. Bacteriophage MS2 simply provides one example of an internal control, although any suitable alternative may be utilised with the method of the present invention.

In one embodiment, the test card includes a probe which permits detection of human ribonuclease P gene (RNAse P). The presence of human RNAse P nucleic acid in the sample indicates that human biological material has been collected. Alternatively, other human genome markers may be used as probe targets and their corresponding probes may be included on the test card.

The assay method of the present invention may include a nucleic acid amplification step, in which case each probe of the present invention is employed in combination with a pair of (forward and reverse) primers—said primer pair cooperate to amplify a stretch of target nucleic acid, which is then recognised by the probe (by binding thereto) during the detection step. By way of example, primers 1f (forward) & 1r (reverse) coordinate with the first probe, and in use all three nucleic acid sequences are included in the first well. The same applies to primers 2f & 2r in combination with the second probe (within the second well) through to primers 41f & 41r in combination with the forty first probe (within the forty first well).

In one embodiment, the method employs a test card comprising one or more additional wells and corresponding one or more additional probes selected from:
42) a forty second well that includes a forty second probe, wherein the forty second probe has a nucleic acid sequence that comprises a nucleic acid sequence having at least 80% sequence identity to the nucleic acid sequence GTGCARTTYG (SEQ ID NO: 338);
43) a forty third well that includes a forty third probe, wherein the forty third probe has a nucleic acid sequence that comprises a nucleic acid sequence having at least 80% sequence identity to the nucleic acid sequence YGCYTCGGAR (SEQ ID NO: 339);
44) a forty fourth well that includes a forty fourth probe, wherein the forty fourth probe has a nucleic acid sequence that comprises a nucleic acid sequence having at least 80% sequence identity to the nucleic acid sequence CTTGTGGANC (SEQ ID NO: 340);
45) a forty fifth well that includes a forty fifth probe, wherein the forty fifth probe has a nucleic acid sequence that comprises a nucleic acid sequence having at least 80% sequence identity to the nucleic acid sequence CATTCCATTC (SEQ ID NO: 341);
46) a forty sixth well that includes an forty sixth probe, wherein the forty sixth probe has a nucleic acid sequence that comprises a nucleic acid sequence having at least 80% sequence identity to the nucleic acid sequence WGTGTTTGCA (SEQ ID NO: 342);
47) a forty seventh well that includes a forty seventh probe, wherein the forty seventh probe has a nucleic acid sequence that comprises a nucleic acid sequence having at least 80% sequence identity to the nucleic acid sequence ACCACGGGAT (SEQ ID NO: 343);
48) a forty eighth well that includes a forty eighth probe, wherein the forty eighth probe has a nucleic acid sequence that comprises a nucleic acid sequence having at least 80% sequence identity to the nucleic acid sequence GTCCTCGCTG (SEQ ID NO: 344);
49) a forty ninth well that includes a forty ninth probe, wherein the forty ninth probe has a nucleic acid sequence that comprises a nucleic acid sequence having at least 80% sequence identity to the nucleic acid sequence GCCCGCGACG (SEQ ID NO: 345);

wherein the same method steps are employed as hereinbefore described.

Probes 42-49 respectively permit sensitive detection of:
42) Adenovirus
43) ADP17 Adenovirus;
44) Parechovirus;
45) Influenza virus B;
46) Influenza virus B;
47) *Mycobacterium tuberculosis;*
48) *Mycobacterium tuberculosis;*
49) *Mycobacteria* (general);

Thus, the above-defined method provides a rapid assay for the detection of any one or more of said respiratory infection-causing microorganisms in a uniplex format assay. Similarly, said method provides a rapid assay for the confirmation that all of said respiratory infection-causing microorganisms are absent from a sample in a uniplexed format assay.

Primer 1f comprises a nucleic acid sequence that has at least 80% sequence identity to AAGCWGGATTCTACC (SEQ ID NO: 42), and primer 1r comprises a nucleic acid sequence that has at least 80% sequence identity to TCCCATTATGCCTAG (SEQ ID NO: 43).

Primer 2f comprises a nucleic acid sequence that has at least 80% sequence identity to CCTGAATGYGGCTAA (SEQ ID NO: 44), and primer 2r comprises a nucleic acid sequence that has at least 80% sequence identity to CGGACACCCAAAGTA (SEQ ID NO: 45).

Primer 3f comprises a nucleic acid sequence that has at least 80% sequence identity to ATCCCACAAAAYCAG (SEQ ID NO: 46), and primer 3r comprises a nucleic acid sequence that has at least 80% sequence identity to CTACACATAATAARA (SEQ ID NO: 47).

Primer 4f comprises a nucleic acid sequence that has at least 80% sequence identity to GATGTCCATCAAGCT (SEQ ID NO: 48), and primer 4r comprises a nucleic acid sequence that has at least 80% sequence identity to TARAGCAATAGGTCT (SEQ ID NO: 49).

Primer 5f comprises a nucleic acid sequence that has at least 80% sequence identity to CCTGTCACCTCTGAC (SEQ ID NO: 50), and primer 5r comprises a nucleic acid sequence that has at least 80% sequence identity to TGGACAAAKCGTCTA (SEQ ID NO: 51).

Primer 6f comprises a nucleic acid sequence that has at least 80% sequence identity to GGRTACGCTGCAGAC (SEQ ID NO: 52), and primer 6r comprises a nucleic acid sequence that has at least 80% sequence identity to AGTCCAGACATCTAG (SEQ ID NO: 53).

Primer 7f comprises a nucleic acid sequence that has at least 80% sequence identity to ATACTCAGAGACCCA (SEQ ID NO: 54), and primer 7r comprises a nucleic acid sequence that has at least 80% sequence identity to ATAYTGTTGCATAGC (SEQ ID NO: 55).

Primer 8f comprises a nucleic acid sequence that has at least 80% sequence identity to TGCTCCTGATCARCC (SEQ ID NO: 56), and primer 8r comprises a nucleic acid sequence that has at least 80% sequence identity to TCCCACCATRGCATA (SEQ ID NO: 57).

Primer 9f comprises a nucleic acid sequence that has at least 80% sequence identity to TATCCTCAGAGATCC (SEQ ID NO: 58), and primer 9r comprises a nucleic acid sequence that has at least 80% sequence identity to ACATACTGTTGCATG (SEQ ID NO: 59).

Primer 10f comprises a nucleic acid sequence that has at least 80% sequence identity to CTTGTACAGGARATG (SEQ ID NO: 60), and primer 6r comprises a nucleic acid sequence that has at least 80% sequence identity to TCCCACCATRGCATA (SEQ ID NO: 61).

Primer 11f comprises a nucleic acid sequence that has at least 80% sequence identity to RGTSGAYCCCATGGA (SEQ ID NO: 62), and primer 11r comprises a nucleic acid sequence that has at least 80% sequence identity to SGGYGTRCGSAGGTA (SEQ ID NO: 63).

Primer 12f comprises a nucleic acid sequence that has at least 80% sequence identity to AGTCAAATCAGTCGA (SEQ ID NO: 64), and primer 12r comprises a nucleic acid sequence that has at least 80% sequence identity to CCCTGCAYACACATG (SEQ ID NO: 65).

Primer 13f comprises a nucleic acid sequence that has at least 80% sequence identity to AGTCAAATCAGTCGA (SEQ ID NO: 66), and primer 13r comprises a nucleic acid sequence that has at least 80% sequence identity to CCCTGCAYACACATG (SEQ ID NO: 67).

Primer 14f comprises a nucleic acid sequence that has at least 80% sequence identity to CATCTGYTTAACAAG (SEQ ID NO: 68) or GGARACATACGTGAA (SEQ ID NO: 260), and primer 14r comprises a nucleic acid sequence that has at least 80% sequence identity to AAGAIACTGATCCTG (SEQ ID NO: 69) or ATTGTAYTGAACAGC (SEQ ID NO: 261).

Primer 15f comprises a nucleic acid sequence that has at least 80% sequence identity to CCTGAATGYGGCTAA (SEQ ID NO: 70), and primer 15r comprises a nucleic acid sequence that has at least 80% sequence identity to CGGACACCCAAAGTA (SEQ ID NO: 71).

Primer 16f comprises a nucleic acid sequence that has at least 80% sequence identity to TTATCCAAAATGTGA (SEQ ID NO: 72), and primer 16r comprises a nucleic acid sequence that has at least 80% sequence identity to GCATCACCGGATGAT (SEQ ID NO: 73).

Primer 17f comprises a nucleic acid sequence that has at least 80% sequence identity to TTATCCTAARTGTGA (SEQ ID NO: 74), and primer 17r comprises a nucleic acid sequence that has at least 80% sequence identity to ATCACCACTRCTAGT (SEQ ID NO: 75).

Primer 18f comprises a nucleic acid sequence that has at least 80% sequence identity to TTATCCCAAATGTGA (SEQ ID NO: 76), and primer 18r comprises a nucleic acid sequence that has at least 80% sequence identity to AGCRTCACCAGAAGT (SEQ ID NO: 77).

Primer 19f comprises a nucleic acid sequence that has at least 80% sequence identity to CTATCCTAAGTGTGA (SEQ ID NO: 78), and primer 19r comprises a nucleic acid sequence that has at least 80% sequence identity to TGCATCACCAGAAGT (SEQ ID NO: 79).

Primer 20f comprises a nucleic acid sequence that has at least 80% sequence identity to KCNTACATGCACATC (SEQ ID NO: 80), and primer 20r comprises a nucleic acid sequence that has at least 80% sequence identity to GGGRTTYCTRAACTT (SEQ ID NO: 81).

Primer 21f comprises a nucleic acid sequence that has at least 80% sequence identity to CAGGAARTGACGTAT (SEQ ID NO: 82), and primer 21r comprises a nucleic acid sequence that has at least 80% sequence identity to TGTTCACTCGCCGGA (SEQ ID NO: 83).

Primer 22f comprises a nucleic acid sequence that has at least 80% sequence identity to MGAGGTCGAAACGTA (SEQ ID NO: 84), and primer 22r comprises a nucleic acid sequence that has at least 80% sequence identity to CACGGTGAGCGTRAA (SEQ ID NO: 85).

Primer 23f comprises a nucleic acid sequence that has at least 80% sequence identity to TGTAGACACAGTACT (SEQ ID NO: 86), and primer 23r comprises a nucleic acid sequence that has at least 80% sequence identity to ATGCTTGTCTTCTAG (SEQ ID NO: 87).

Primer 24f comprises a nucleic acid sequence that has at least 80% sequence identity to ATCAGTTGGCTAACA (SEQ ID NO: 88), and primer 24r comprises a nucleic acid sequence that has at least 80% sequence identity to AGCCACTGCCCCATT (SEQ ID NO: 89).

Primer 25f comprises a nucleic acid sequence that has at least 80% sequence identity to GCCCCCCTACAATTG (SEQ ID NO: 90), and primer 25r comprises a nucleic acid sequence that has at least 80% sequence identity to ATTCTGGGTTTCCTA (SEQ ID NO: 91).

Primer 26f comprises a nucleic acid sequence that has at least 80% sequence identity to TGTTGAACGCAGCAA (SEQ ID NO: 92), and primer 26r comprises a nucleic acid sequence that has at least 80% sequence identity to GCAACTAGTGACCTA (SEQ ID NO: 93).

Primer 27f comprises a nucleic acid sequence that has at least 80% sequence identity to ATGATGCMATMAAYT (SEQ ID NO: 94), and primer 27r comprises a nucleic acid sequence that has at least 80% sequence identity to CCATTGGAGTTTGAC (SEQ ID NO: 95).

Primer 28f comprises a nucleic acid sequence that has at least 80% sequence identity to CTTCGGGGCRTCATG (SEQ ID NO: 96) or YAGYGGITACAARGA (SEQ ID NO: 262), and primer 28r comprises a nucleic acid sequence that has at least 80% sequence identity to CYGCATGTTTCCRTT (SEQ ID NO: 97) or AIRAARCATGAYGCC (SEQ ID NO: 263).

Primer 29f comprises a nucleic acid sequence that has at least 80% sequence identity to IGGYYACCARTCAAC (SEQ ID NO: 98), and primer 29r comprises a nucleic acid sequence that has at least 80% sequence identity to YARCATYCCATTGTG (SEQ ID NO: 99).

Primer 30f comprises a nucleic acid sequence that has at least 80% sequence identity to YGAYCARTGCATGGA (SEQ ID NO: 100), and primer 30r comprises a nucleic acid sequence that has at least 80% sequence identity to GGCRACAGTIGAATA (SEQ ID NO: 101).

Primer 31f comprises a nucleic acid sequence that has at least 80% sequence identity to GGATGGAACCGTYAA (SEQ ID NO: 102), and primer 31r comprises a nucleic acid sequence that has at least 80% sequence identity to TTGTTGTGACCTCAT (SEQ ID NO: 103).

Primer 32f comprises a nucleic acid sequence that has at least 80% sequence identity to RGCTTTCAGACAAGA (SEQ ID NO: 104), and primer 32r comprises a nucleic acid sequence that has at least 80% sequence identity to GACCGCATGATTGAC (SEQ ID NO: 105).

Primer 33f comprises a nucleic acid sequence that has at least 80% sequence identity to CCTGAATGYGGCTAA (SEQ ID NO: 106), and primer 33r comprises a nucleic acid sequence that has at least 80% sequence identity to CGGACACCCAAAGTA (SEQ ID NO: 107).

Primer 34f comprises a nucleic acid sequence that has at least 80% sequence identity to ATGCAAGACGCTATG (SEQ ID NO: 108), and primer 34r comprises a nucleic acid sequence that has at least 80% sequence identity to GTCTTTCATTTGCTG (SEQ ID NO: 109).

Primer 35f comprises a nucleic acid sequence that has at least 80% sequence identity to GTGGCAGTTGGGTCA (SEQ ID NO: 110), and primer 35r comprises a nucleic acid sequence that has at least 80% sequence identity to CTTGATCCGCCCACA (SEQ ID NO: 111).

Primer 36f comprises a nucleic acid sequence that has at least 80% sequence identity to TATAAAGGCGTTGCT (SEQ ID NO: 112), and primer 36r comprises a nucleic acid sequence that has at least 80% sequence identity to GATGGTCGCAGACTT (SEQ ID NO: 113).

Primer 37f comprises a nucleic acid sequence that has at least 80% sequence identity to CATCGTTCCCGGCAG (SEQ ID NO: 114), and primer 37r comprises a nucleic acid sequence that has at least 80% sequence identity to GTTTACTAATCCCCA (SEQ ID NO: 115).

Primer 38f comprises a nucleic acid sequence that has at least 80% sequence identity to TGGGAAGGTGCTTCA (SEQ ID NO: 116), and primer 38r comprises a nucleic acid sequence that has at least 80% sequence identity to CGCGGATGCTAATGG (SEQ ID NO: 117).

Primer 39f comprises a nucleic acid sequence that has at least 80% sequence identity to TGGGAAGGTGCTTCA (SEQ ID NO: 118), and primer 39r comprises a nucleic acid sequence that has at least 80% sequence identity to TCCTGCGCGGATGCT (SEQ ID NO: 119).

Primer 40f comprises a nucleic acid sequence that has at least 80% sequence identity to CTCTCCGTATTCACG (SEQ ID NO: 120), and primer 40r comprises a nucleic acid sequence that has at least 80% sequence identity to GACCCCACGATGAC (SEQ ID NO: 121).

Primer 41f comprises a nucleic acid sequence that has at least 80% sequence identity to TTGGACCTGCGAGCG (SEQ ID NO: 122), and primer 41r comprises a nucleic acid sequence that has at least 80% sequence identity to GCTGTCTCCACAAGT (SEQ ID NO: 123).

Primer 42f comprises a nucleic acid sequence that has at least 80% sequence identity to KCNTACATGCACATC (SEQ ID NO: 80), and primer 42r comprises a nucleic acid sequence that has at least 80% sequence identity to GGGRTTYCTRAACTT (SEQ ID NO: 81).

Primer 43f comprises a nucleic acid sequence that has at least 80% sequence identity to ITACATGCAYATCKC (SEQ ID NO: 267), and primer 43r comprises a nucleic acid sequence that has at least 80% sequence identity to GGCRAAYTGCACCAG (SEQ ID NO: 268) or GGCAAACTGCACGAG (SEQ ID NO: 269).

Primer 44f comprises a nucleic acid sequence that has at least 80% sequence identity to AGATGGCGTRCCATA (SEQ ID NO: 272), and primer 44r comprises a nucleic acid sequence that has at least 80% sequence identity to ACTAGAGGATGGCTG (SEQ ID NO: 273).

Primer 45f comprises a nucleic acid sequence that has at least 80% sequence identity to GCTATGAACACAGCA (SEQ ID NO: 276), and primer 45r comprises a nucleic acid sequence that has at least 80% sequence identity to TTGGACGTCTTCTCC (SEQ ID NO: 277).

Primer 46f comprises a nucleic acid sequence that has at least 80% sequence identity to GATGTCCATCAAGCT (SEQ ID NO: 48), and primer 46r comprises a nucleic acid sequence that has at least 80% sequence identity to TARAGCAATAGGTCT (SEQ ID NO: 49).

Primer 47f comprises a nucleic acid sequence that has at least 80% sequence identity to GTAACACGTGGGTGA (SEQ ID NO: 280), and primer 47r comprises a nucleic acid sequence that has at least 80% sequence identity to ACCGCTAAAGCGCTT (SEQ ID NO: 281).

Primer 48f comprises a nucleic acid sequence that has at least 80% sequence identity to TTCGTCRTACGCAAT (SEQ ID NO: 284), and primer 48r comprises a nucleic acid sequence that has at least 80% sequence identity to GGTCGGGACGGTGAG (SEQ ID NO: 285).

Primer 49f comprises a nucleic acid sequence that has at least 80% sequence identity to TTCGTCRTACGCAAT (SEQ ID NO: 284), and primer 49r comprises a nucleic acid sequence that has at least 80% sequence identity to GGTCGGGACGGTGAG (SEQ ID NO: 285).

The biological sample is typically a sample that has been taken from a patient (i.e. an ex vivo and/or isolated sample). In one embodiment, a nucleic acid extraction step may be performed on the sample—conventional nucleic acid extraction protocols are well known in the art. The extracted nucleic acid sample is then applied to the test card so that is contacts each of the wells (and thus each of the probes within said wells).

The nucleic acid 'hybridization reaction' (comprising probe and primers working together) step of the present invention is typically performed at a temperature of 50-70° C. (for example, 55-65° C. or 56-64° C. or 57-63° C. or 58-62° C. or 59-61° C. or approximately 60° C.). Said temperature is typically held for a time period of 10-30 seconds (for example, 15-25 seconds or 17-23 seconds or 19-21 seconds or approximately 20 seconds). If a nucleic acid amplification step is included in the method of the invention, said 'hybridization reaction' (comprising probe and primers added in excess at the beginning) step is preferably included in each cycle of the amplification step.

If a nucleic acid amplification step is employed, this step is typically performed at a temperature of 90-100° C. (for example, 92-98° C. or 94-96° C. or approximately 95° C. degrees) for a typical period of 0.1-10 seconds (for example, 0.5-5 seconds or 0.7-2 seconds or approximately 1 second) followed by a reduced temperature of 50-70° C. (for example, 55-65° C. or 57-63° C. or 59-61° C. or approximately 60° C.) for a period 10-30 seconds (for example, 15-25 seconds or 17-23 seconds or 19-21 seconds or approximately 20 seconds). If a nucleic acid amplification step is employed, said step typically includes 35-55 cycles (for example, 40-50 cycles or 44-46 cycles or approximately 45 cycles). A reverse transcription step is typically employed at the very start at a temperature of 40-60° C. (for example, 45-55° C. or 48-52° C. or approximately 50° C.) for a time period of 3-7 minutes (for example, 4-6 minutes or approximately 5 minutes).

BRIEF DESCRIPTION OF THE DRAWINGS

The Drawing shows a test card comprising a columnar arrangement of wells.

In one embodiment, the method may be performed in an Applied Biosystems 7900HT (high throughput) instrument. By way of example, said instrument may employ a 384 well test card (aka plate) RT-PCR platform that allows, for example, 8 different samples to be analysed in parallel via 8 distinct columns present on a single test card—see the Drawing. Each column may comprise 48 individual target wells, thereby permitting each sample to be (substantially simultaneously) screened for 48 different respiratory infection-causing microorganisms (effectively 46 respiratory infection-causing microorganisms of two 'control' wells are employed). Alternative apparatuses and systems (including corresponding test cards) are available commercially and have equal application in the context of the present invention.

In one embodiment, the method employs PCR such as RT-PCR.

In use, a sample (typically extracted nucleic acid samples) is mixed with 2-times to 5-times concentrated buffer (e.g. PCR buffer; also referred to as reaction mix). For example, Xµl of sample is mixed with the same volume (Xµl) of 2-times concentrated buffer. The sample (including buffer) is then applied to the test card (and into each well)—typically a volume in the range of 0.1-50 µl or 0.5-30 µl or 0.5-20 µl or 0.5-10 µl or 1-5 µl is delivered to each well. Preferably approximately 0.5 µl, 1 µl, 2 µl, 3 µl, 4 µl or 5 µl of sample (including buffer) is delivered to each well.

In the case of a test card comprising a columnar arrangement of wells (see, for example, the Drawing), the sample (including buffer) may simply be applied to a reservoir at the top of each column, and the test card then spun in a centrifuge to deliver sample plus reagent mix (in the volume range as identified above) to each of the wells forming in each column. In the case of the AB7900HT system, each well typically comprises 48 wells so sample is applied by centrifugal delivery to each of said 48 wells. In more detail, up to 8 samples may be added respectively to the 8 reservoirs at the top of each column (e.g. with a fin pipette). Referring to the Drawing, the little pods indicate the discrete assay wells, which in turn include the corresponding probes (and optionally the corresponding primers). The illustrated test card shows a set up in which 48 wells (also referred to as pods) are present per channel—in use, each well typically receives a final 1 µl reaction volume by centrifugal delivery down the columnar channel.

Each well includes one specific probe type of the present invention (and optionally the corresponding primer pair). In one embodiment, said probe is present in its well in a lyophilized form. Thus, once the liquid sample has been applied to the well surface, the lyophilized probe (optionally including the corresponding primer pair) becomes re-hydrated, thereby allowing the detection step to proceed within a liquid medium.

A well of the present invention is designed to hold slightly more than the relevant liquid volume (sample plus buffer/reaction mix) of the assay that is to be performed in said well. Each well is discrete to allow location of a single probe type within a single well, thereby permitting the method to detect the presence or absence of specific target microorganisms. Following application of sample to the test card, all of the wells containing probe(s) may be sealed shut by use of one or more films/sheets, thereby preventing accidental migration of liquid (and potentially probes) between wells. A well of the present invention may be positioned in the same horizontal plane as the test card, though equally may be positioned above or below said plane.

Compared to a standard battery of multiplex reaction set-ups, the present invention offers time and resource savings in both reaction set up manipulations and permits collation of data from multiple instruments.

The present invention also provides a test card for use in the hereinbefore described methods. In one embodiment, the test card is made from a plastics material. For the purpose of assisting the user, the test card should have sufficient rigidity to support the weight of the card (including applied sample), for example when in a substantially horizontal position as typically held by the user during normal use.

The test card comprises a plurality of wells (optionally arranged in a columnar format to permit sample application by centrifugal delivery), wherein at least six wells are provided, and wherein the first well includes the first probe, the second well includes the second probe, the third well includes the third probe, the fourth well includes the fourth probe, the fifth well includes the fifth probe, and the sixth well includes the sixth probe of the present invention as herein defined. Each well typically only includes (a plurality of) one specific probe of the present invention. By way of example, in one embodiment, the first probe is present in the first well (though typically absent from any of the other wells), and the second probe is present in the second well (though typically absent from any of the other wells), and so on.

Each probe may optionally be associated with its corresponding primer pair. Thus, in addition to the first probe, the first well may include the first pair of corresponding forward and reverse primers. Each well typically only includes (a plurality of) one specific primer pair of the present invention. By way of example, in one embodiment, the first primer pair (and the first probe) is present in the first well but typically absent from any of the other wells, and the second primer pair (and the second probe) is present in the second well but typically absent from any of the other wells, and so on. Alternatively, more than one probe (and optionally its corresponding primer pair) may be present in a single well.

Each probe may be immobilised within its respective well—said immobilisation may be permanent (e.g. via a covalent link, optionally introduced by any commercially available chemical cross-linking reagents) or transient (e.g. via a non-covalent bond such as a hydrogen bond, or via an ionic bond). For example, the first probe may be immobilised within the first well, and the second probe may be immobilised within the second well, and so on. Immobilisation of the respective probes makes the test cards easier to handle, improves storage stability, and minimises the risk of probe migration between wells. The probes are preferably immobilised within the wells by simple adsorption on to a surface present in the wells, such as on to a wall of a well. Thus, in one embodiment, a probe-containing solution is prepared, applied to the surface of a well, and then allowed to dry on the surface of the well. Conventional stabilising compounds (e.g. sugars) may be added to the probe-containing solution prior to application to a well surface.

The test card may include one or more additional wells selected from the seventh well through to the thirteenth well (including respectively the seventh though to the thirteenth probes) as herein described. For example, the card may include each of the seventh well through to the thirteenth well (including respectively the seventh though to thirteenth probes).

The test card may alternatively or additionally include one or more additional wells selected from the fourteenth well through to the thirty third well (including respectively the fourteenth though to the thirty third probes) as herein described. For example, the card may include each of the fourteenth well through to the thirty third well (including respectively the fourteenth though to thirty third probes).

Each of the above-described test card embodiments may further include one or more wells for detecting atypical microbial (e.g. bacterial) respiratory infection-causing agents. In this embodiment, the test card may further include one or more additional wells selected from the thirty fourth well through to the thirty ninth well (including respectively the thirty fourth though to the thirty ninth probes) as herein described. For example, the card may include each of the thirty fourth well through to the thirty ninth well (including respectively the thirty fourth though to thirty ninth probes).

Each of the above-described test card embodiments may further include one or more 'control' wells. In this embodiment, the test card may further include one or both of the fortieth and forty first wells (including respectively the fortieth and/or forty first probes) as herein described.

Definitions Section

Reference to at least 80% sequence identity includes at least 82%, at least 84%, at least 86%, at least 88%, at least 90%, at least 91%, at least 92%, at least 93%, at least 94%, at least 95%, at least 96%, at least 97%, at least 98%, at least 99%, and 100% sequence identity (to each and every nucleic acid sequence presented herein and/or to each and every SEQ ID NO presented herein).

The one-letter reference code for nucleotides employed throughout this specification means:

A adenine
C cytosine
G guanine
T thymine
U uracil
I inosine
X inosine
R guanine or adenine
Y thymine or cytosine
K guanine or thymine
M adenine or cytosine
S guanine or cytosine
W adenine or thymine
B not adenine
D not cytosine
H not guanine
V not thymine
N any nucleic acid base All nucleic acid sequences presented herein are presented in a 5'-to-3' (left-to-right) orientation.

The probes of the invention are designed to hybridise to their target nucleic acid sequence present on the target respiratory infection-causing microorganism in question. It is preferred that the binding conditions are such that a high level of specificity is provided—i.e. hybridisation of the probe occurs under "stringent conditions". In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target (or complement) sequence hybridises to a perfectly matched probe. In this regard, the $T_m$ of probes of the present invention, at a salt concentration of about 0.02M or less at pH 7, is for example above 60° C., such as about 70° C.

Premixed buffer solutions are commercially available (e.g. EXPRESSHYB Hybridisation Solution from CLONTECH Laboratories, Inc.), and hybridisation can be performed according to the manufacturer's instructions.

Probes of the present invention are screened to minimise self-complementarity and dimer formation (probe-probe binding), and are selected so as to have minimal homology with human DNA. The selection process typically involves comparing a candidate probe sequence with human DNA and rejecting the probe if the homology is greater than 50%. The aim of this selection process is to reduce annealing of probe to contaminating human DNA sequences and hence allow improved specificity of the assay.

Any of the probes described herein may comprise a tag and/or label. The tag and/or label may, for example, be located (independently of one another) towards the middle or towards or at the 5' or 3' end of the herein described probes, for example at the 5' end.

Hence, following hybridisation of tagged/labelled probe to target nucleic acid, the tag/label is associated with the target nucleic acid. Alternatively, if an amplification step is employed, the probes may act as primers during the method of the invention and the tag/label may therefore become incorporated into the amplification product as the primer is extended.

Examples of suitable labels include detectable labels such as radiolabels or fluorescent or coloured molecules, enzymatic markers or chromogenic markers—e.g. dyes that produce a visible colour change upon hybridisation of the probe. By way of example, the label may be digoxygenin, fluorescein-isothiocyanate (FITC), R-phycoerythrin, Alexa 532 or Cy3. The probes preferably contain a Fam label (e.g. a 5' Fam label), and/or a minor groove binder (MGB). The label may be a reporter molecule, which is detected directly, such as by exposure to photographic or X-ray film. Alternatively, the label is not directly detectable, but may be detected indirectly, for example, in a two-phase system. An example of indirect label detection is binding of an antibody to the label.

Examples of suitable tags include "complement/anti-complement pairs". The term "complement/anti-complement pair" denotes non-identical moieties that form a non-covalently associated, stable pair under appropriate conditions. Examples of suitable tags include biotin and streptavidin (or avidin). By way of example, a biotin tag may be captured using streptavidin, which may be coated onto a substrate or support such as a bead (for example a magnetic bead) or membrane. Likewise, a streptavidin tag may be captured using biotin, which may be coated onto a substrate or support such as a bead (for example a magnetic bead) or membrane. Other exemplary complement/anti-complement pairs include receptor/ligand pairs, antibody/antigen (or hapten or epitope) pairs, and the like. Another example is a nucleic acid sequence tag that binds to a complementary sequence. The latter may itself be pre-labelled, or may be attached to a surface (e.g. a bead) which is separately labelled. An example of the latter embodiment is the well-known Luminex® bead system. Other exemplary pairs of tags and capture molecules include receptor/ligand pairs and antibody/antigen (or hapten or epitope) pairs. Where subsequent dissociation of the complement/anti-complement pair is desirable, the complement/anti-complement pair has a binding affinity of, for example, less than $10^9$ $M^{-1}$.

The probes of the invention may be labelled with different labels or tags, thereby allowing separate identification of each probe when used in the method of the present invention.

Any conventional method may be employed to attach nucleic acid tags to a probe of the present invention (e.g. to the 5' end of the defined binding region of the probe). Alternatively, nucleic acid probes of the invention (with pre-attached nucleic acid tags) may be constructed by commercial providers.

The sample is for example a clinical sample (or is derived from a clinical sample) such as: faeces or blood, sputum, nose and throat swabs, bronchoalveolar lavage, tracheal aspirate, nasopharyngeal aspirates, lung tissue samples, cerebrospinal fluid, archaeological samples. The sample is preferably a human tissue/sample or is a sample derived therefrom (e.g. a nucleic acid extracted sample).

If an amplification step is employed, this step may be carried out using methods and platforms known in the art, for example PCR (for example, with the use of "Fast DNA Polymerase", Life Technologies), such as real-time PCR, block-based PCR, ligase chain reaction, glass capillaries, isothermal amplification methods including loop-mediated isothermal amplification, rolling circle amplification transcription mediated amplification, nucleic acid sequence-based amplification, signal mediated amplification of RNA technology, strand displacement amplification, isothermal multiple displacement amplification, helicase-dependent amplification, single primer isothermal amplification, and circular helicase-dependent amplification.

If employed, amplification may be carried using any amplification platform—as such, an advantage of this embodiment of the assay is that it is platform independent and not tied to any particular instrument.

In one embodiment, a general amplification step (e.g. pre-detection) may be employed to increase the amount of target nucleic acid present in the sample. In this embodiment, PCR amplification primers are typically employed to amplify approximately 100-400 base pair regions of the target/complementary nucleic acid that contain the nucleotide targets of the present invention. In the presence of a suitable polymerase and DNA precursors (dATP, dCTP, dGTP and dTTP), forward and reverse primers are extended in a 5' to 3' direction, thereby initiating the synthesis of new nucleic acid strands that are complementary to the individual strands of the target nucleic acid. The primers thereby drive amplification of target nucleic acid sequences, thereby generating amplification products comprising said target nucleic acid sequences.

In one embodiment, an amplification step may be employed in which the probes of the present invention act as primers. In this embodiment, the probes (acting as primers) are extended from their 3' ends (i.e. in a 5'-to-'3') direction. The resulting amplification products typically comprise 100-400 base pair regions of the target/complementary nucleic acid. This embodiment may be employed in conjunction with a general amplification step, such as the one described above.

The detection step may be carried out by any known means. In this regard, the probe or amplification product may be tagged and/or labelled, and the detection method may therefore comprise detecting said tag and/or label.

In one embodiment, the probe(s) may comprise a tag and/or label. Thus, in one embodiment, following hybridisation of tagged/labelled probe to target nucleic acid, the tag/label becomes associated with the target nucleic acid. Thus, in one embodiment, the assay may comprise detecting the tag/label and correlating presence of tag/label with presence of infectious microorganism nucleic acid.

In one embodiment, tag and/or label may be incorporated during extension of the probe(s). In doing so, the amplification product(s) become tagged/labelled, and the assay may therefore comprise detecting the tag/label and correlating presence of tag/label with presence of amplification product, and hence the presence of infectious microorganism nucleic acid.

By way of example, in one embodiment, the amplification product may incorporate a tag/label (e.g. via a tagged/labelled dNTP such as biotin-dNTP) as part of the amplification process, and the assay may further comprise the use of a binding partner complementary to said tag (e.g. streptavidin) that includes a detectable tag/label (e.g. a fluorescent label, such as R-phycoerythrin). In this way, the amplified product incorporates a detectable tag/label (e.g. a fluorescent label, such as R-phycoerythrin).

In one embodiment, the probe(s) and/or the amplification product(s) may include a further tag/label (as the complement component) to allow capture of the amplification product(s).

By way of example, a "complement/anti-complement" pairing may be employed in which an anti-complement capture component binds to said further tag/label (complement component) and thereby permits capture of the probe(s) and/or amplification product(s). Examples of suitable "complement/anti-complement" partners have been described earlier in this specification, such as a complementary pair of nucleic acid sequences, a complementary antibody-antigen pair, etc. The anti-complement capture component may be attached (e.g. coated) on to a substrate or solid support—examples of suitable substrates/supports include membranes and/or beads (e.g. a magnetic or fluorescent bead). Capture methods are well known in the art. For example, Luminex® beads may be employed. Alternatively, the use of magnetic beads may be advantageous because the beads (plus captured, tagged/labelled amplification product) can easily be concentrated and separated from the sample, using conventional techniques known in the art.

Immobilisation provides a physical location for the anti-complement capture component (or probes), and may serve to fix the capture component/probe at a desired location and/or facilitate recovery or separation of probe. The support may be a rigid solid support made from, for example, glass or plastic, such as a bead (for example a fluorescent or magnetic bead). Alternatively, the support may be a membrane, such as nylon or nitrocellulose membrane. 3D matrices are also suitable supports for use with the present invention—e.g. polyacrylamide or PEG gels. Immobilisation to a support/platform may be achieved by a variety of conventional means. By way of example, immobilisation onto a support such as a nylon membrane may be achieved by UV cross-linking. Alternatively, biotin-labelled molecules may be bound to streptavidin-coated substrates (and vice-versa), and molecules prepared with amino linkers may be immobilised on to silanised surfaces. Another means of immobilisation is via a poly-T tail or a poly-C tail, for example at the 3' or 5' end. Said immobilisation techniques apply equally to the probe component (and primer pair component, if present) of the present invention.

In one embodiment, the probes of the invention comprise a nucleic acid sequence tag/label (e.g. attached to each probe at the 5' end of the defined sequence of the probe that binds to target/complement nucleic acid). In more detail, each of the probes is provided with a different nucleic acid sequence tag/label, wherein each of said tags/labels (specifically) binds to a complementary nucleic acid sequence present on the surface of a bead. Each of the different tags/labels binds to its complementary sequence counterpart (and not to any of the complementary sequence counterparts of the other tags), which is located on a uniquely identifiable bead. In this regard, the beads are uniquely identifiable, for example by means of fluorescence at a specific wavelength. Thus, in use, probes of the invention bind to target nucleic acid (if present in the sample). Thereafter, (only) the bound probes may be extended (in the 3' direction) in the presence of one or more labelled dNTP (e.g. biotin labelled dNTPs, such as biotin-dCTPs).

The extended primers may be contacted with a binding partner counterpart to the labelled dNTPs (e.g. a streptavidin labelled fluorophore, such as streptavidin labelled R-phycoerythrin), which binds to those labelled dNTPs that have become incorporated into the extended primers. Thereafter, the labelled extended primers may be identified by allowing them to bind to their nucleic acid counterparts present on the uniquely identifiable beads. The latter may then be "called" (e.g. to determine the type of bead present by wavelength emission) and the nature of the primer extension (and thus the type of target/complement nucleic acid present) may be determined.

Preferred Embodiments of the Present Invention

The first probe comprises a nucleic acid sequence that has at least 80% sequence identity to TAGGCAATGCWGC (SEQ ID NO: 124).

The second probe comprises a nucleic acid sequence that has at least 80% sequence identity to TCYGGGAYGGGAC-CRACTA (SEQ ID NO: 125).

The third probe comprises a nucleic acid sequence that has at least 80% sequence identity to TCAGCACCAGA-CACACC (SEQ ID NO: 126).

The fourth probe comprises a nucleic acid sequence that has at least 80% sequence identity to TCTGGTCATTG-GRGCC (SEQ ID NO: 127).

The fifth probe comprises a nucleic acid sequence that has at least 80% sequence identity to CGCT-CACTGGGCACGGT (SEQ ID NO: 128).

The sixth probe comprises a nucleic acid sequence that has at least 80% sequence identity to AACTGRGTGT-TCATTTTGT (SEQ ID NO: 129).

The seventh probe comprises a nucleic acid sequence that has at least 80% sequence identity to ATARTTTCCA-GGGGCAAA (SEQ ID NO: 130).

The eighth probe comprises a nucleic acid sequence that has at least 80% sequence identity to CCATCCGCAAGT-CAATG (SEQ ID NO: 131).

The ninth probe comprises a nucleic acid sequence that has at least 80% sequence identity to ATAGTTGCCTGGT-GCGAA (SEQ ID NO: 132).

The tenth probe comprises a nucleic acid sequence that has at least 80% sequence identity to CTGATAARGTAG-GTGCTT (SEQ ID NO: 133).

The eleventh probe comprises a nucleic acid sequence that has at least 80% sequence identity to CGCGGCRT-CATYGA (SEQ ID NO: 134).

The twelfth probe comprises a nucleic acid sequence that has at least 80% sequence identity to CCTCATARTGR-TAATTAG (SEQ ID NO: 135).

The thirteenth probe comprises a nucleic acid sequence that has at least 80% sequence identity to CCTCATAG-TAATAATTAG (SEQ ID NO: 136).

The fourteenth probe comprises a nucleic acid sequence that has at least 80% sequence identity to ATGGTACTGT-GACAATGC (SEQ ID NO: 137) or CACGARGGCTC-CACRTAC (SEQ ID NO: 286).

The fifteenth probe comprises a nucleic acid sequence that has at least 80% sequence identity to TCTGYRGCGGAAC-CGACT (SEQ ID NO: 138).

The sixteenth probe comprises a nucleic acid sequence that has at least 80% sequence identity to AGCTAAC-GAGTGTGCG (SEQ ID NO: 139).

The seventeenth probe comprises a nucleic acid sequence that has at least 80% sequence identity to CTTGCGAAT-GAATGYGC (SEQ ID NO: 140).

The eighteenth probe comprises a nucleic acid sequence that has at least 80% sequence identity to TTGGGYTCTAAGCATGTTA (SEQ ID NO: 141).

The nineteenth probe comprises a nucleic acid sequence that has at least 80% sequence identity to TTAGGT-TCTAAGCATGTCA (SEQ ID NO: 142).

The twentieth probe comprises a nucleic acid sequence that has at least 80% sequence identity to CYTCGGAG-TAYCTSAGYCC (SEQ ID NO: 143).

The twenty first probe comprises a nucleic acid sequence that has at least 80% sequence identity to TCAGACTG-CATCCGGTCT (SEQ ID NO: 144).

The twenty second probe comprises a nucleic acid sequence that has at least 80% sequence identity to TCYT-GTCACCTCTGAC (SEQ ID NO: 145).

The twenty third probe comprises a nucleic acid sequence that has at least 80% sequence identity to ACAGAGTGT-GTYACTGT (SEQ ID NO: 146).

The twenty fourth probe comprises a nucleic acid sequence that has at least 80% sequence identity to TTG-GAATTTCTGGCCC (SEQ ID NO: 147).

The twenty fifth probe comprises a nucleic acid sequence that has at least 80% sequence identity to CGTTGCCG-GATGGA (SEQ ID NO: 148).

The twenty sixth probe comprises a nucleic acid sequence that has at least 80% sequence identity to CCTACAG-CAACTGTTACC (SEQ ID NO: 149).

The twenty seventh probe comprises a nucleic acid sequence that has at least 80% sequence identity to CATT-GCTCCAGAAWAT (SEQ ID NO: 150).

The twenty eighth probe comprises a nucleic acid sequence that has at least 80% sequence identity to TTCTNGCCATTGYAA (SEQ ID NO: 151) or TGGTT-TAGCTTCGGG (SEQ ID NO: 255).

The twenty ninth probe comprises a nucleic acid sequence that has at least 80% sequence identity to CAATGTYCCT-GTRACACA (SEQ ID NO: 152).

The thirtieth probe comprises a nucleic acid sequence that has at least 80% sequence identity to AARCTGGARTCTGARG (SEQ ID NO: 153).

The thirty first probe comprises a nucleic acid sequence that has at least 80% sequence identity to CCTTCRACTGTGTCTCC (SEQ ID NO: 154).

The thirty second probe comprises a nucleic acid sequence that has at least 80% sequence identity to CACTGTGTCACCGCTCA (SEQ ID NO: 155).

The thirty third probe comprises a nucleic acid sequence that has at least 80% sequence identity to TCYGGGAYGGRACCRACTA (SEQ ID NO: 156).

The thirty fourth probe comprises a nucleic acid sequence that has at least 80% sequence identity to CGCTCAATTGGCTTTAACC (SEQ ID NO: 157).

The thirty fifth probe comprises a nucleic acid sequence that has at least 80% sequence identity to CGTGGAGAGTGTGTG (SEQ ID NO: 158).

The thirty sixth probe comprises a nucleic acid sequence that has at least 80% sequence identity to CAACAGACGCTGGCG (SEQ ID NO: 159).

The thirty seventh probe comprises a nucleic acid sequence that has at least 80% sequence identity to TGTCGGCGTTTATTGG (SEQ ID NO: 160).

The thirty eighth probe comprises a nucleic acid sequence that has at least 80% sequence identity to CTACTTGGTGTGAYGC (SEQ ID NO: 161).

The thirty ninth probe comprises a nucleic acid sequence that has at least 80% sequence identity to CTACTTGGTGTGAYGC (SEQ ID NO: 162).

The fortieth probe comprises a nucleic acid sequence that has at least 80% sequence identity to TCGATAGATCAAGGTGCCT (SEQ ID NO: 163).

The forty first probe comprises a nucleic acid sequence that has at least 80% sequence identity to TTCTGACCTGAAGGCTCTG (SEQ ID NO: 164).

The forty second probe comprises a nucleic acid sequence that has at least 80% sequence identity to CTGGTGCARTTYGCCCG (SEQ ID NO: 247).

The forty third probe comprises a nucleic acid sequence that has at least 80% sequence identity to CAGGAYGCYTCGGARTACCT (SEQ ID NO: 248).

The forty fourth probe comprises a nucleic acid sequence that has at least 80% sequence identity to CCAYGCTTGTGGANCTTATGC (SEQ ID NO: 249).

The forty fifth probe comprises a nucleic acid sequence that has at least 80% sequence identity to TTYCCCATTCCATTCATTGT (SEQ ID NO: 250).

The forty sixth probe comprises a nucleic acid sequence that has at least 80% sequence identity to CCCWGTGTTTGCAGTRGA (SEQ ID NO: 251).

The forty seventh probe comprises a nucleic acid sequence that has at least 80% sequence identity to TAGGACCACGGGATGCA (SEQ ID NO: 252).

The forty eighth probe comprises a nucleic acid sequence that has at least 80% sequence identity to AAGTTGTCCTCGCTGCCACTC (SEQ ID NO: 253).

The forty ninth probe comprises a nucleic acid sequence that has at least 80% sequence identity to CAGTGCCCGCGACGGACG (SEQ ID NO: 254).

Primer 1f comprises a nucleic acid sequence that has at least 80% sequence identity to GGGWGGWGAAGCWGGATTCTACC (SEQ ID NO: 165), and primer 1r comprises a nucleic acid sequence that has at least 80% sequence identity to ACCTCTRTACTCTCCCATTATGCCTAG (SEQ ID NO: 166).

Primer 2f comprises a nucleic acid sequence that has at least 80% sequence identity to CGGCCCCTGAATGYGGCTAA (SEQ ID NO: 167), and primer 1r comprises a nucleic acid sequence that has at least 80% sequence identity to GAAACACGGACACCCAAAGTA (SEQ ID NO: 168).

Primer 3f comprises a nucleic acid sequence that has at least 80% sequence identity to CATCAGGTAAYATCCCACAAAAYCAG (SEQ ID NO: 169), and primer 3r comprises a nucleic acid sequence that has at least 80% sequence identity to GTGAATATTAARGCACCTACACATAATAARA (SEQ ID NO: 170).

Primer 4f comprises a nucleic acid sequence that has at least 80% sequence identity to GCAGCTCTGATGTCCATCAAGCT (SEQ ID NO: 171), and primer 4r comprises a nucleic acid sequence that has at least 80% sequence identity to CAGCTTGCTTGCTTARAGCAATAGGTCT (SEQ ID NO: 172).

Primer 5f comprises a nucleic acid sequence that has at least 80% sequence identity to GACCRATCCTGTCACCTCTGAC (SEQ ID NO: 173), and primer 5r comprises a nucleic acid sequence that has at least 80% sequence identity to AGGGCATTYTGGACAAAKCGTCTA (SEQ ID NO: 174).

Primer 6f comprises a nucleic acid sequence that has at least 80% sequence identity to AGTGGRTACGCTGCAGAC (SEQ ID NO: 175), and primer 6r comprises a nucleic acid sequence that has at least 80% sequence identity to GTTCAGCATTATAAGTCCAGACATCTAG (SEQ ID NO: 176).

Primer 7f comprises a nucleic acid sequence that has at least 80% sequence identity to GCYCCTTTYATATGTATACTCAGAGACCCA (SEQ ID NO: 177), and primer 7r comprises a nucleic acid sequence that has at least 80% sequence identity to TGTTCTTCCAGTTACATAYTGTTGCATAGC (SEQ ID NO: 178).

Primer 8f comprises a nucleic acid sequence that has at least 80% sequence identity to AAGTGYATGACTGCTCCTGATCARCC (SEQ ID NO: 179), and primer 8r comprises a nucleic acid sequence that has at least 80% sequence identity to TTGCCAATRTCTCCCACCATRGCATA (SEQ ID NO: 180).

Primer 9f comprises a nucleic acid sequence that has at least 80% sequence identity to GCTCCTTTYATCTGTATCCTCAGAGATCC (SEQ ID NO: 181), and primer 9r comprises a nucleic acid sequence that has at least 80% sequence identity to TGATCTTCCCGTCACATACTGTTGCATG (SEQ ID NO: 182).

Primer 10f comprises a nucleic acid sequence that has at least 80% sequence identity to GGTTATAAGACAATTTCTTGTACAGGARATG (SEQ ID NO: 183), and primer 10r comprises a nucleic acid sequence that has at least 80% sequence identity to TTTGCAATRTCTCCCACCATRGCATA (SEQ ID NO: 184).

Primer 11f comprises a nucleic acid sequence that has at least 80% sequence identity to ATGACTTTTGARGTSGAYCCCATGGA (SEQ ID NO: 185), and primer 11r comprises a nucleic acid sequence that has at least 80% sequence identity to GCCGAGAASGGYGTRCGSAGGTA (SEQ ID NO: 186).

Primer 12f comprises a nucleic acid sequence that has at least 80% sequence identity to AGGGAAARATAGTCAAATCAGTCGA (SEQ ID NO: 187), and primer 12r comprises a nucleic acid sequence that has at least 80% sequence identity to CAGTTATCCCTGCAYACACATG (SEQ ID NO: 188).

Primer 13f comprises a nucleic acid sequence that has at least 80% sequence identity to AGGGAAARATAGT- CAAATCAGTCGA (SEQ ID NO: 189), and primer 13r comprises a nucleic acid sequence that has at least 80% sequence identity to CAGTTATCCCTGCAYACACATG (SEQ ID NO: 190).

Primer 14f comprises a nucleic acid sequence that has at least 80% sequence identity to GAAGGGTCMAACATCT-GYTTAACAAG (SEQ ID NO: 191) or GGGCAAATATG-GARACATACGTGAA (SEQ ID NO: 256), and primer 14r comprises a nucleic acid sequence that has at least 80% sequence identity to GCTWGTGGGAARAAAGAIACT-GATCCTG (SEQ ID NO: 192) or TCTTTTTCTARGACAT-TGTAYTGAACAGC (SEQ ID NO: 257).

Primer 15f comprises a nucleic acid sequence that has at least 80% sequence identity to CGGCCCCTGAATGYG-GCTAA (SEQ ID NO: 193), and primer 15r comprises a nucleic acid sequence that has at least 80% sequence identity to GAAACACGGACACCCAAAGTA (SEQ ID NO: 194).

Primer 16f comprises a nucleic acid sequence that has at least 80% sequence identity to ATGGGTTGGGATTATC-CAAAATGTGA (SEQ ID NO: 195), and primer 16r comprises a nucleic acid sequence that has at least 80% sequence identity to AGCAGTTGTAGCATCACCGGATGAT (SEQ ID NO: 196).

Primer 17f comprises a nucleic acid sequence that has at least 80% sequence identity to ATGGGTTGGGATTATC-CTAARTGTGA (SEQ ID NO: 197), and primer 17r comprises a nucleic acid sequence that has at least 80% sequence identity to GCAGTAGTTGCATCACCACTRCTAGT (SEQ ID NO: 198).

Primer 18f comprises a nucleic acid sequence that has at least 80% sequence identity to ATGGGTTGGGATTATC-CCAAATGTGA (SEQ ID NO: 199), and primer 18r comprises a nucleic acid sequence that has at least 80% sequence identity to GCTGTACTAGCRTCACCAGAAGT (SEQ ID NO: 200).

Primer 19f comprises a nucleic acid sequence that has at least 80% sequence identity to ATGGGATGGGACTATC-CTAAGTGTGA (SEQ ID NO: 201), and primer 19r comprises a nucleic acid sequence that has at least 80% sequence identity to GCTGTAGTTGCATCACCAGAAGT (SEQ ID NO: 202).

Primer 20f comprises a nucleic acid sequence that has at least 80% sequence identity to GCCCCARTGGKCNTA-CATGCACATC (SEQ ID NO: 203), and primer 20r comprises a nucleic acid sequence that has at least 80% sequence identity to GCCACIGTGGGRTTYCTRAACTT (SEQ ID NO: 204).

Primer 21f comprises a nucleic acid sequence that has at least 80% sequence identity to CACKCCCAGGAART-GACGTAT (SEQ ID NO: 205), and primer 21r comprises a nucleic acid sequence that has at least 80% sequence identity to CCAGAGATGTTCACTCGCCGGA (SEQ ID NO: 206).

Primer 22f comprises a nucleic acid sequence that has at least 80% sequence identity to GAGTCTTCTAACMGAG-GTCGAAACGTA (SEQ ID NO: 207), and primer 22r comprises a nucleic acid sequence that has at least 80% sequence identity to GGGCACGGTGAGCGTRAA (SEQ ID NO: 208).

Primer 23f comprises a nucleic acid sequence that has at least 80% sequence identity to TCAACAGACACTGTA-GACACAGTACT (SEQ ID NO: 209), and primer 23r comprises a nucleic acid sequence that has at least 80% sequence identity to GTTTCCCGTTATGCTTGTCT-TCTAG (SEQ ID NO: 210).

Primer 24f comprises a nucleic acid sequence that has at least 80% sequence identity to ATGGCATCAGTTG-GCTAACA (SEQ ID NO: 211), and primer 24r comprises a nucleic acid sequence that has at least 80% sequence identity to ACAGCCACTGCCCCATT (SEQ ID NO: 212).

Primer 25f comprises a nucleic acid sequence that has at least 80% sequence identity to GGAATAGCCCCCCTA-CAATTG (SEQ ID NO: 213), and primer 25r comprises a nucleic acid sequence that has at least 80% sequence identity to AATTCGCATTCTGGGTTTCCTA (SEQ ID NO: 214).

Primer 26f comprises a nucleic acid sequence that has at least 80% sequence identity to CCTTTTTGTTGAACGCA-GCAA (SEQ ID NO: 215), and primer 26r comprises a nucleic acid sequence that has at least 80% sequence identity to CGGATGAGGCAACTAGTGACCTA (SEQ ID NO: 216).

Primer 27f comprises a nucleic acid sequence that has at least 80% sequence identity to GCCGAATGATGCMAT-MAAYT (SEQ ID NO: 217), and primer 27r comprises a nucleic acid sequence that has at least 80% sequence identity to CGCACCCATTGGAGTTTGAC (SEQ ID NO: 218).

Primer 28f comprises a nucleic acid sequence that has at least 80% sequence identity to TGGTTTAGCT-TCGGGGCRTCATG (SEQ ID NO: 219) or GTNAAACT-GAGYAGYGGITACAARGA (SEQ ID NO: 258), and primer 28r comprises a nucleic acid sequence that has at least 80% sequence identity to AATRGTGCACYGCAT-GTTTCCRTT (SEQ ID NO: 220) or GGCIAGAAGIAI-RAARCATGAYGCC (SEQ ID NO: 259).

Primer 29f comprises a nucleic acid sequence that has at least 80% sequence identity to TGCATIGGYYACCART-CAAC (SEQ ID NO: 221), and primer 29r comprises a nucleic acid sequence that has at least 80% sequence identity to GTTGCACAYARCATYCCATTGTG (SEQ ID NO: 222).

Primer 30f comprises a nucleic acid sequence that has at least 80% sequence identity to AATGTGAYGAYCARTG-CATGGA (SEQ ID NO: 223), and primer 30r comprises a nucleic acid sequence that has at least 80% sequence identity to GAGATGAGGCRACAGTIGAATA (SEQ ID NO: 224).

Primer 31f comprises a nucleic acid sequence that has at least 80% sequence identity to ATTCAGACAGGATG-GAACCGTYAA (SEQ ID NO: 225), and primer 31r comprises a nucleic acid sequence that has at least 80% sequence identity to GATACTAAGCTTTGTTGTGACCTCAT (SEQ ID NO: 226).

Primer 32f comprises a nucleic acid sequence that has at least 80% sequence identity to ACCCGATTR-GARGCTTTCAGACAAGA (SEQ ID NO: 227), and primer 32r comprises a nucleic acid sequence that has at least 80% sequence identity to CTGTTGRGACCGCAT-GATTGAC (SEQ ID NO: 228).

Primer 33f comprises a nucleic acid sequence that has at least 80% sequence identity to CGGCCCCTGAATGYG-GCTAA (SEQ ID NO: 229), and primer 33r comprises a nucleic acid sequence that has at least 80% sequence identity to GAAACACGGACACCCAAAGTA (SEQ ID NO: 230).

Primer 34f comprises a nucleic acid sequence that has at least 80% sequence identity to AAAGGCATG-CAAGACGCTATG (SEQ ID NO: 231), and primer 34r comprises a nucleic acid sequence that has at least 80% sequence identity to TGTTAAGAACGTCTTTCATTT-GCTG (SEQ ID NO: 232).

Primer 35f comprises a nucleic acid sequence that has at least 80% sequence identity to CCTTTCGTGGCAGT-TGGGTCA (SEQ ID NO: 233), and primer 35r comprises a nucleic acid sequence that has at least 80% sequence identity to ACTGAGCTTGATCCGCCCACA (SEQ ID NO: 234).

Primer 36f comprises a nucleic acid sequence that has at least 80% sequence identity to CAAGGGC- TATAAAGGCGTTGCT (SEQ ID NO: 235), and primer 36r comprises a nucleic acid sequence that has at least 80% sequence identity to CATGATAATTGATGGTCGCA-GACTT (SEQ ID NO: 236).

Primer 37f comprises a nucleic acid sequence that has at least 80% sequence identity to AATTTCATCGTTCCCG-GCAG (SEQ ID NO: 237), and primer 37r comprises a nucleic acid sequence that has at least 80% sequence identity to GCCGCGTTTACTAATCCCCA (SEQ ID NO: 238).

Primer 38f comprises a nucleic acid sequence that has at least 80% sequence identity to GCACTATGTGGGAAGGT-GCTTCA (SEQ ID NO: 239), and primer 38r comprises a nucleic acid sequence that has at least 80% sequence identity to CTGCGCGGATGCTAATGG (SEQ ID NO: 240).

Primer 39f comprises a nucleic acid sequence that has at least 80% sequence identity to GCACTATGTGGGAAGGT-GCTTCA (SEQ ID NO: 241), and primer 39r comprises a nucleic acid sequence that has at least 80% sequence identity to GTAGTATCCTGCGCGGATGCT (SEQ ID NO: 242).

Primer 40f comprises a nucleic acid sequence that has at least 80% sequence identity to TGGCACTACCCCTCTC-CGTATTCACG (SEQ ID NO: 243), and primer 40r comprises a nucleic acid sequence that has at least 80% sequence identity to GTACGGGCGACCCCACGATGAC (SEQ ID NO: 244).

Primer 41f comprises a nucleic acid sequence that has at least 80% sequence identity to AGATTTGGACCTGC-GAGCG (SEQ ID NO: 245), and primer 41r comprises a nucleic acid sequence that has at least 80% sequence identity to GAGCGGCTGTCTCCACAAGT (SEQ ID NO: 246).

Primer 42f comprises a nucleic acid sequence that has at least 80% sequence identity to GCCCCARTGGKCNTA-CATGCACATC (SEQ ID NO: 203), and primer 42r comprises a nucleic acid sequence that has at least 80% sequence identity to GCCACIGTGGGRTTYCTRAACTT (SEQ ID NO: 204).

Primer 43f comprises a nucleic acid sequence that has at least 80% sequence identity to CARTGGKCITACATG-CAYATCKC (SEQ ID NO: 264), and primer 43r comprises a nucleic acid sequence that has at least 80% sequence identity to GCRCGGGCRAAYTGCACCAG (SEQ ID NO: 265) or GCGCGGGCAAACTGCACGAG (SEQ ID NO: 266).

Primer 44f comprises a nucleic acid sequence that has at least 80% sequence identity to GGTGGYAGATGGCG-TRCCATA (SEQ ID NO: 270), and primer 44r comprises a nucleic acid sequence that has at least 80% sequence identity to TCTRACAAACTTACTAGAGGATGGCTG (SEQ ID NO: 271).

Primer 45f comprises a nucleic acid sequence that has at least 80% sequence identity to ATGGTYTCAGCTAT-GAACACAGCA (SEQ ID NO: 274), and primer 45r comprises a nucleic acid sequence that has at least 80% sequence identity to TGCCAGYTTTTGGACGTCTTCTCC (SEQ ID NO: 275).

Primer 46f comprises a nucleic acid sequence that has at least 80% sequence identity to GCAGCTCTGATGTCCAT-CAAGCT (SEQ ID NO: 171), and primer 46r comprises a nucleic acid sequence that has at least 80% sequence identity to CAGCTTGCTTGCTTARAGCAATAGGTCT (SEQ ID NO: 172).

Primer 47f comprises a nucleic acid sequence that has at least 80% sequence identity to CGAACGGGTGAG-TAACACGTGGGTGA (SEQ ID NO: 278), and primer 47r comprises a nucleic acid sequence that has at least 80% sequence identity to CTCATCCCACAC-CGCTAAAGCGCTT (SEQ ID NO: 279).

Primer 48f comprises a nucleic acid sequence that has at least 80% sequence identity to GACGGGCCTCTTCGT-CRTACGCAAT (SEQ ID NO: 282), and primer 48r comprises a nucleic acid sequence that has at least 80% sequence identity to GAGTGCTAGGTCGGGACGGTGAG (SEQ ID NO: 283).

Primer 49f comprises a nucleic acid sequence that has at least 80% sequence identity to GACGGGCCTCTTCGT-CRTACGCAAT (SEQ ID NO: 282), and primer 49r comprises a nucleic acid sequence that has at least 80% sequence identity to GAGTGCTAGGTCGGGACGGTGAG (SEQ ID NO: 283).

Sequence Homology/Identity

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22 (22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262 (5131) Science 208-214 (1993); Align-M, see, e.g., Ivo Van Walle et al., Align-M—A New Algorithm for Multiple Alignment of Highly Divergent Sequences, 20 (9) Bioinformatics: 1428-1435 (2004). Thus, percent sequence identity is determined by conventional methods. See, for example, Altschul et al., *Bull. Math. Bio.* 48: 603-16, 1986 and Henikoff and Henikoff, *Proc. Natl. Acad. Sci. USA* 89:10915-19, 1992.

Variants of the specific sequences provided above may alternatively be defined by reciting the number of nucleotides that differ between the variant sequences and the specific reference sequences provided above. Thus, in one embodiment, the sequence may comprise (or consist of) a nucleotide sequence that differs from the specific sequences provided above at no more than 2 nucleotide positions, for example at no more than 1 nucleotide position. Conservative substitutions are preferred.

By way of example, variant probe sequences may comprise nucleic acid sequences selected from: GGCAATGCIG (SEQ ID NO: 287); GGCAATGCAG (SEQ ID NO: 288); GGCAATGCTG (SEQ ID NO: 289); AGGCAATGCW (SEQ ID NO: 290) or GCAATGCWGCWCC (SEQ ID NO: 291) for the defined first probe (GGCAATGCWG; SEQ ID NO: 1).

Further examples of variant probe sequences include: GAYGGRACCR (SEQ ID NO: 292); GAYRGGACCR (SEQ ID NO: 293); GATGGGACCR (SEQ ID NO: 294); GACGGGACCR (SEQ ID NO: 295); GAYGGGACCG (SEQ ID NO: 296); GAYGGGACCA (SEQ ID NO: 297); AYGGGACCRA (SEQ ID NO: 298); GGAYGGGACC (SEQ ID NO: 299); GAYGGGACCI (SEQ ID NO: 300); or GAIGGGACCR (SEQ ID NO: 301) for the defined second probe (GAYGGGACCR; SEQ ID NO: 2).

Examples of variant sequences also include: ACCAGACACA (SEQ ID NO: 302); GCACCAGACA (SEQ ID NO: 303); CACIAGACAC (SEQ ID NO: 304); CACCAGAIAC (SEQ ID NO: 305); CACCWGACAC (SEQ ID NO: 306); CACCAGACWC (SEQ ID NO: 307); or CACCARACAC (SEQ ID NO: 308) for the third probe defined as comprising the defined nucleic acid sequence (CACCAGACAC; SEQ ID NO: 3).

More examples of variants include: GGTCATYGGR (SEQ ID NO: 309); GGTCATTGGG (SEQ ID NO: 310); GGTCATTGGA (SEQ ID NO: 311); GTCATTGGRG (SEQ ID NO: 312); TGGTCATTGG (SEQ ID NO: 313); GGTCATCGGR (SEQ ID NO: 314); RGTCATTGGR (SEQ ID NO: 315); AGTCATTGGR (SEQ ID NO: 316); GGTIATTGGR (SEQ ID NO: 317); or GGTCATTIGR (SEQ ID NO: 318) for the fourth probe comprising a defined nucleic acid sequence (GGTCATTGGR; SEQ ID NO: 4).

Further examples of variant probe sequences also comprise: ACTGGGCACG (SEQ ID NO: 319); TCACTGGGCA (SEQ ID NO: 320); CRCTGGGCAC (SEQ ID NO: 321); CGCTGGGCAC (SEQ ID NO: 322); CACTGGGIAC (SEQ ID NO: 323); CAITGGGCAC (SEQ ID NO: 324); CACTGGRCAC (SEQ ID NO: 325); CACTRGGCAC (SEQ ID NO: 326); or CACYGGGCAC (SEQ ID NO: 327) for the fifth probe with a nucleic acid sequence that has been defined (CACTGGGCAC: SEQ ID NO: 5).

Examples of variant probe sequences for the defined sixth probe (RGTGTTCATT; SEQ ID NO: 6) includes: GRGTGTTCAT (SEQ ID NO: 328); GTGTTCATTT (SEQ ID NO: 329); AGTGTTCATT (SEQ ID NO: 330); GGTGTTCATT (SEQ ID NO: 331); RGTGTTIATT (SEQ ID NO: 332); RGTRTTCATT (SEQ ID NO: 333); RGTGTTCAWT (SEQ ID NO: 334); RGTGTWCATT (SEQ ID NO: 335); RGTGTTCWTT (SEQ ID NO: 336); or RGIGTTCATT (SEQ ID NO: 337).

Fragments of the above-mentioned sequences (and sequence variants thereof as defined above) may also be employed, for example, fragments comprising 10, 9, 8, 7, 6, 5, 4, 3, 2 or 1 base pair of the defined sequences described herein.

EXAMPLE 1

H5 Panel Challenge

To confirm the accuracy of our assay, a test card was prepared containing 41 wells—the wells were loaded with the respective first through to forty first probes, respectively.

We challenged the test card with a known H5 influenza proficiency panel of viruses. The protocol employed includes the following steps: 50° C. for 5 mins (RT); 95° C. for 20 seconds; 95° C. for 1 second×45; and 60° C. for 20 seconds.

Referring to Table 1 (see below), the expected Ct results are indicated in the left-hand columns, and the test card results are indicated in the extreme right-hand column. In a real time PCR assay, a positive reaction is detected by accumulation of a fluorescent signal. The Ct (cycle threshold) value is defined as the number of cycles required for the fluorescent signal to cross the threshold (i.e. exceed background level).

The results for the test card correctly called all the specimens. Notably, the test card probes correctly called the tamiflu resistant/sensitive mixture in specimen G*, and the two H5N1 isolates were correctly called with all three relevant probes. The test card probes also correctly subtyped all the specimens, H1/H3 seasonal and H1v2009. All the other probe results were negative.

TABLE 1

HPA Influenza Proficiency Panel (2011) Expected Results

| ID | Virus | Type/ Subtype | Flu A Expected Ct value[1] | Flu B Expected Ct value[1] | H5 Expected Ct value[1] | Non-H5 Subtyping HA Expected Ct Value[2] | Oseltamivir Susceptibility | Respiratory Array Card Results | | | |
|---|---|---|---|---|---|---|---|---|---|---|---|
| A | A/Brisbane/59/2009 | H1N1 | 34.61 | — | — | H1 35.65 | — | Flu A QUAD 36.45 | | 18s | 4.86 |
| | | | | | | | | Flu A CDC 33.84 | | MS2 | 31.36 |
| | | | | | | | | H1 CFI 32.54 H1 32.75 | | Rn P | 23.56 |
| B | A/Perth/16/2009 | H3N2 | 35.27 | — | — | H3 33.54 | — | Flu A QUAD ---- | | 18s | 5.43 |
| | | | | | | | | Flu A CDC 35.30 | | MS2 | 30.89 |
| | | | | | | | | H3 CFI 32.01 H3 33.30 | | Rn P | 23.44 |
| C | B/Brisbane/60/2008 | B | — | 33.39 | — | — | — | | | 18s | 7.08 |
| | | | | | | | | Flu B QUAD 35.51 | | MS2 | 29.69 |
| | | | | | | | | Flu B ABI 33.89 | | Rn P | 24.45 |
| D* | A/England/107/2010 | H1N1 | 32.21 | — | — | H1 27.18 | Sensitive | Flu A Quad 33.10 | Tamiflu Sens 33.04 | 16s | 5.89 |
| | | (2009) | | | | N1 30.50 | | Flu A CDC 29.91 | | MS2 | 32.29 |
| | | | | | | | | H1v 30.9 H1v 31.02 | N1CFI 32.81 | Rn P | 23.91 |
| E | A/England/90/2011 | H1N1 | 34.36 | — | — | H1 28.97 | Resistant | Flu A QUAD 35.70 | Tamiflu Resis 33.04 | 18s | 5.71 |
| | | (2009) | | | | N1 31.66 | | Flu A CDC 32.25 | | MS2 | 32.08 |
| | | | | | | | | H1v 32.04 H1v 32.36 | n1 CFI 32.81 | Rn P | 23.98 |
| F* | B/England/176/2010 | B | — | 21.04 | — | — | — | | | 18s | 7.60 |
| | | | | | | | | Flu B QUAD 29.15 | | MS2 | 31.70 |
| | | | | | | | | Flu B 22.20 | | Rn P | 26.50 |
| G* | A/England/107/2010 & | H1N1 | 30.87 | — | — | H1 25.95 | Sensitive | Flu A QUAD 30.86 | Tamiflu S/R 32.18/31.27 | 18s | 5.16 |
| | A/England/90/2011 | (2009) | | | — | N1 28.45 | Resistant | Flu A CDC 27.99 | | MS2 | 31.60 |
| | | | | | | | Mixture | H1v 28.96 H1v 28.53 | N1CFI 28.71 | RN p | 23.40 |
| H | A/Aragon/3218/2008 | H1N1 | 32.92 | — | — | H1 36.08 | Sensitive | Flu A QUAD 33.79 | | 18s | 6.18 |
| | | | | | | N1 37.94 | | Flu A CDC 32.32 | | MS2 | 30.66 |
| | | | | | | | | N1 31.81 H1 38.70 | | Rn P | 23.44 |
| I | Hep 2 cells (Negative) | — | — | — | — | — | — | All Negative bar the controls | | | |
| J | A/Swine/Italy/1477/96 | H3N2 | 31.95 | — | — | H3 32.97 | — | Flu A QUAD 30.73 | | 18s | 6.01 |
| | | | | | | | | Flu A CDC 23.75 | | MS2 | 31.14 |
| | | | | | | | | H3 CFI 27.36 H3 32.94 | | RN p | 24.56 |
| K | A/Pennsylvania/14/2010 | H3N2 | 20.55 | — | — | H3 35.56 | — | Flu A QUAD 21.37 | | 18s | 6.29 |
| | | | | | | | | Flu A CDC 20.75 | | MS2 | 30.24 |
| | | | | | | | | H3 CFI 24.30 H3 19.35 | | RN p | 24.60 |
| L | A/Egypt/3300NAMRUS/2008 (RG13) | H5N1 | 24.20 | — | 33.49 | — | — | Flu A QUAD 24.55 | Tamiflu Sens 28.43 | 18s | 7.04 |
| | | | | | | | | Flu A CDC 23.70 | N1CFI 38.22 | MS2 | 30.84 |
| | | | | | | | | H5 CFI 29.59 H5 FRET 24.14 H5 24.54 | | Rn P | 24.49 |
| M | A/ck/Vietnam/NCVD-016/2008 (RG12) | H5N1 | 24.39 | — | 27.72 | — | — | Flu A QUAD 25.25 | Tamiflu Sens 34.04 | 18s | 6.19 |
| | | | | | | | | Flu A CDC 24.18 | N1CFI 28.37 | MS2 | 31.32 |
| | | | | | | | | H5 CFI 25.37 H5 FRET 25.23 H5 23.27 | | Rn P | 25.02 |

[1]Mean Ct value from pre-testing using HPA NSM 25 primers/probes
[2]Mean Ct value from pre-testing using HPA NSM 29, 48 and 50 primers/probes

EXAMPLE 2

Flu A/B Panel Challenge

To confirm the accuracy of our assay, a test card was prepared as per Example 1 containing 41 wells—the wells were loaded with our respective first through to forty first probes, respectively.

We challenged the test card with a flu A/B proficiency panel of viruses. Referring to Table 2 (see below), the expected Ct results are indicated in the left-hand columns, and the test card results are indicated in the extreme right-hand column. Again the array correctly called each of the specimens in the panel.

TABLE 2

QCMD 2010 Influenza virus A and B RNA EQA Programme

| Panel code | Matrix | Sample contents | Ct Value | Expected Result | | Real-time in house Ct Value | Array PCR Results |
|---|---|---|---|---|---|---|---|
| INFRNA 10-01 | VTM | Flu-A H3N2 | 30 | Flu-A Positive | core | 25 | Flu A 33.99/31.71 H3 seasonal 30.87/30.49 |
| INFRNA 10-02 | VTM | Flu-A H1N1v | 35 | Flu-A Positive | core | 27 | Flu A 35.97/31.97 H1v 31.37/32.06 N1 32.06 TamS 33.50 |
| INFRNA 10-03 | VTM | Flu-A H1N1 | 33 | Flu-A Positive | | 28 | Flu A 38.71/35.39 H1 seasonal 35.7/33.33 |
| INFRNA 10-04 | VTM | Flu-A/B Neg | | Flu A/B Neg | core | | |
| INFRNA 10-05 | VTM | Flu-A H1N1v | 35 | Flu-A Positive | core | 26 | Flu A 34.91/32.77 H1v 32.17/31.37 N1 31.66 TamS 34.66 |
| INFRNA 10-06 | VTM | Flu-B | 32 | Flu-B Positive | core | 25 | Flu B 31.96/30.42 |
| INFRNA 10-07 | VTM | Flu-B | 39 | Flu-B Positive | core | 32 | Flu B 34.09/28.23 |
| INFRNA 10-08 | VTM | Flu-A H1N1v | 30 | Flu-A Positive | core | 23 | Flu A 31.83/28.49 H1v 28.94/27.88 N1 28.612 TamS 30.47 |
| INFRNA 10-09 | VTM | Flu-A H1N1 | 29 | Flu-A Positive | core | 25 | Flu A 33.16/30.88 H1 seasonal 30.92/30.237 |
| INFRNA 10-10 | VTM | Flu-A/B Neg | | FluA/B Neg | core | | |
| INFRNA 10-11 | VTM | Flu-A H1N1v | 38 | Flu-A Positive | | 29 | Flu A ----/35.53 H1v 33.99/35.75 N1 35.81 TamS 35.71 |
| INFRNA 10-12 | VTM | Flu-A H3N2 | 37 | Flu-A Positive | | 27 | Flu A 39.33/34.35 H3 seasonal 33.41/---- |

EXAMPLE 3

A Specimen from a Patient with Suspect Avian H5 Influenza was Analysed According to the Present Invention in Parallel with Conventional Multiplex Tests A 60 year-old retired teacher from Tasmania, Australia traveled with his wife to Hong Kong on 26 Aug. 2011. The person remained in Hong Kong for 5 days before continuing to UK, arriving on the 31 Aug. 2011. The person presented to hospital on 4 Sep. 2011 but sent home as not considered ill. The person re-presented on 8 Sep. 2011 having become more ill. Respiratory specimens (sputum and nose/throat swab) were taken on 8 Sep. 2011.

On Saturday 10 Sep. 2011 the specimens were tested according to the present invention (assay completed in a total of 2 hours), and the test card results are indicated below.

Probe 22 (Flu A Quad)=26.3
Probe 5 (Flu A CDC)=23.7
Probe 26 (H3)=22.7
Positive controls: probe 40 (MS2 phage)=32.0; probe 41 (RNase P)=22.6
All other probes on the test card were clearly negative.
Test card result: H5 negative, imported H3N2 seasonal influenza In parallel, a conventional multiplex assay was performed (assays completed in a total of 4-5 hours), and the results are provided below:

Flu A Quad=26.4
Flu A CDC=17.9
H3 Cfl=19.7
Routine multiplex result: H5 negative, imported H3N2 seasonal influenza These data confirm that the singleplex test card assay of the present invention was far faster (more than twice as quick) and even more accurate (higher Ct values) in delivering the assay results. Moreover, the singleplex assay card approach of the present invention permits a considerably more comprehensive screen (in terms of the number of different pathogens tested) than conventional multiplex approaches (all in a much reduced timeframe).

EXAMPLE 4

A Second Suspect Avian H5 Case was Analysed According to the Present Invention in Parallel with Conventional Multiplex Tests A 50 year-old lady who had recently traveled to North Somalia, Djibouti and Dubai, presented at a London Hospital with an acute case of bilateral pneumonia (requiring intubation) on the Oct. 11, 2011. Specimens (nose/throat swabs) were tested in accordance with the present invention (total assay time=2 hours), and the test card results are indicated below.

Probe 3 (hMPV)=31.0—this was the only virus entity detected in the specimen
Positive controls: probe 40 (MS2 phage)=31.0: probe 41 (RNase P)=29.4
All other probes on the card were clearly negative.
Result: Avian H5 influenza virus negative, patient has a hMPV infection
Parallel multiplex results (assay time=4-5 hours)
hMPV=25.0
Result: Avian H5 influenza virus negative, and hMPV infection confirmed.

These data confirm that the singleplex test card approach of the present invention proved superior (higher Ct values) and provided quicker results than convention multiplex tests, delivering the results hours earlier and screening the patient for additional virus and bacterial pathogens.

EXAMPLE 5

Performance of the Present Invention was Assessed Using Quality Control for Molecular Diagnostics Panels In order to fully assess the performance of the test card, commercially available external Quality Control for Molecular Diagnostics (QCMD) panels (www.qcmd.org) for a range of different pathogens were tested, thereby providing an International bench mark for the quality, performance and robustness of the test card results.

| | |
|---|---|
| QCMD 2011 *Legionella pneumophila* DNA EQA Programme | 100% CORRECT |
| QCMD 2010 Parainfluenzavirus RNA EQA Programme | 100% CORRECT |
| QCMD 2010 *Rhinovirus* & *Coronavirus* RNA EQA Programme | 100% CORRECT |
| QCMD 2011 *Enterovirus* RNA EQA Programme | 11/12 correct |
| QCMD 2010 *Adenovirus* DNA EQA Programme | 6/8 correct |
| QCMD 2010 *Metapneumovirus* & *Respiratory Syncytial virus* | 10/12 correct |
| QCMD 2011 *C. pneumoniae* & *Mycoplasma pneumoniae* | 9/11 correct |

These data confirm that the singleplex test card approach of the present invention yielded both sensitivity and performance that was comparable to conventional multiplex assays, though concluded in a much shorter timeframe (2 hours versus 4-5 hours).

EXAMPLE 6

A Comparative Head-to-Head Assessment of the Present Invention with Conventional Multiplex Respiratory Assays Using 216 Clinical Specimens Positive for Various Viruses The assay card results are presented below.

| | |
|---|---|
| 30 RSV positive specimens | 100% concordance with routine multiples assays |
| 14 Flu B positive specimens | 100% concordance with routine multiplex assays (the specimens included two co-infections, hMPV & RSV) |
| 54 Flu A positive specimens | 100% concordance with routine multiplex assays (the specimens included a Tamiflu resistant isolate, and a Flu B co-infection) |
| 10 *Boca virus* positive specimens | 100% concordance with routine multiplex assays (8/10 found to be co-infections by the assay card, high bocavirus viral loads-Ct values in the range of 15-26) |
| 31 Human parainfluenza virus positive specimens (types 1-4) | 100% concordance with routine multiplex assays |
| 17 *Adenovirus* positive specimens | 100% concordance with routine multiplex assays |
| 22 *Rhinovirus* positive specimens | 100% concordance with routine multiplex assays |
| 11 *enterovirus* positive specimens | 100% concordance with routine multiplex assays |
| 11 *Coronavirus* positive specimens | 100% concordance with routine multiplex assays |
| 16 *Human metapneumovirus* | 100% concordance with routine multiplex assays |

These data confirm that the singleplex test card approach of the present invention again proved highly specific and sensitive as well as robust, only detecting the correct pathogens. In particular, no false positives were observed with the test card. The only false negative result was with a single coronavirus specimen that had a Ct>32 on our routine real-time multiplex assay and was not detected on the array card. Co-infections were also correctly identified using the test cards. 31 known negative specimens were also processed through the cards and no false positives results were observed for any of the targets.

The invention claimed is:

1. A quantitative uniplex method for detecting the presence of one or more of at least six respiratory infection-causing microorganisms in a sample or detecting the absence of said respiratory infection-causing microorganisms in said sample, said method comprising:
  A) applying a sample to a test card, wherein said test card comprises six discrete wells:
   1) a first well that includes a first probe, for detecting the presence or absence of Respiratory syncytial virus (RSV A & B), wherein the first probe has a nucleic acid sequence that comprises the nucleic acid sequence TAGGCAATGCWGC (SEQ ID NO: 124);
   2) a second well that includes a second probe, for detecting the presence or absence of Rhinoviruses, wherein the second probe has a nucleic acid sequence that comprises the nucleic acid sequence TCYGGGAYGGGACCRACTA (SEQ ID NO: 125);
3) a third well that includes a third probe, for detecting the presence or absence of Human Metapneumovirus (hMPV), wherein the third probe has a nucleic acid sequence that comprises the nucleic acid sequence TCAGCACCAGACACACC (SEQ ID NO: 126);
4) a fourth well that includes a fourth probe, for detecting the presence or absence of Influenza B (Flu B Quad), wherein the fourth probe has a nucleic acid sequence that comprises the nucleic acid sequence TCTGGTCATTGGRGCC (SEQ ID NO: 127);
5) a fifth well that includes a fifth probe, for detecting the presence or absence of Influenza A (Flu A CDC DC), wherein the fifth probe has a nucleic acid sequence that comprises the nucleic acid sequence CGCTCACTGGGCACGGT (SEQ ID NO: 128);
6) a sixth well that includes a sixth probe, for detecting the presence or absence of Influenza A subtype H5 (H5 FRET), wherein the sixth probe has a nucleic acid sequence that comprises the nucleic acid sequence AACTGRGTGTTCATTTTGT (SEQ ID NO: 129);
B) allowing nucleic acid present in the sample to contact with the probes within said wells;
C) detecting for the presence of bound nucleic acid complex in which sample nucleic acid has bound to one or more of said probes;
wherein the presence of bound nucleic acid complex confirms that nucleic acid from one or more of said six respiratory infection-causing microorganisms is present within the sample, and wherein the absence of bound nucleic acid complex confirms that nucleic acid from all of said six respiratory infection-causing microorganisms is absent within the sample and wherein the probes comprise a detectable label and/or a detectable tag.

2. The quantitative method according to claim 1, wherein the test card further comprises a seventh well that includes a seventh probe, for detecting the presence or absence of Human parainfluenza virus type 1 (HPIV 1), wherein the seventh probe has a nucleic acid sequence that comprises a nucleic acid sequence having at least 90% sequence identity to the nucleic acid sequence of SEQ ID NO: 7.

3. The method according to claim 1, wherein the test card comprises each of an additional seventh through to thirteenth wells and a corresponding seventh through to thirteenth additional probes.

4. The quantitative method according to claim 3, wherein the test card comprises one or more additional wells and corresponding one or more additional probes selected from:
14) a fourteenth well that includes a fourteenth probe, for detecting the presence or absence of Respiratory syncytial virus (RSV #2); (RSV #3), wherein the fourteenth probe has a nucleic acid sequence that comprises a nucleic acid sequence having at least 90% sequence identity to the nucleic acid sequence of SEQ ID NO: 14;
15) a fifteenth well that includes a fifteenth probe, for detecting the presence or absence of Enteroviruses, wherein the fifteenth probe has a nucleic acid sequence that comprises a nucleic acid sequence having at least 90% sequence identity to the nucleic acid sequence of SEQ ID NO: 15;
16) a sixteenth well that includes a sixteenth probe, for detecting the presence or absence of Severe Acute Respiratory Syndrome coronavirus (SARS), wherein the sixteenth probe has a nucleic acid sequence that comprises a nucleic acid sequence having at least 90% sequence identity to the nucleic acid sequence of SEQ ID NO: 16;
17) a seventeenth well that includes a seventeenth probe, for detecting the presence or absence of Group 2 Coronaviruses OC43 and HKU1 (GP2 OC43/HKU1), wherein the seventeenth probe has a nucleic acid sequence that comprises a nucleic acid sequence having at least 90% sequence identity to the nucleic acid sequence of SEQ ID NO: 17;
18) an eighteenth well that includes an eighteenth probe, for detecting the presence or absence of Group 1 Coronavirus NL63 (GP1 NL63), wherein the eighteenth probe has a nucleic acid sequence that comprises a nucleic acid sequence having at least 90% sequence identity to the nucleic acid sequence of SEQ ID NO: 18;
19) a nineteenth well that includes a nineteenth probe, for detecting the presence or absence of Group 1 Coronavirus 229E (GP1 229E), wherein the nineteenth probe has a nucleic acid sequence that comprises a nucleic acid sequence having at least 90% sequence identity to the nucleic acid sequence of SEQ ID NO: 19;
20) a twentieth well that includes a twentieth probe, for detecting the presence or absence of Human Adenoviruses, wherein the twentieth probe has a nucleic acid sequence that comprises a nucleic acid sequence having at least 90% sequence identity to the nucleic acid sequence of SEQ ID NO: 20;
21) a twenty first well that includes a twenty first probe, for detecting the presence or absence of Bocavirus, wherein the twenty first probe has a nucleic acid sequence that comprises a nucleic acid sequence having at least 90% sequence identity to the nucleic acid sequence of SEQ ID NO: 21;
22) a twenty second well that includes a twenty second probe, for detecting the presence or absence of Influenza A (Flu A Quad), wherein the twenty second probe has a nucleic acid sequence that comprises a nucleic acid sequence having at least 90% sequence identity to the nucleic acid sequence of SEQ ID NO: 22;
23) a twenty third well that includes a twenty third probe, for detecting the presence or absence of Influenza A H1 2009 (H1 sw 2009), wherein the twenty third probe has a nucleic acid sequence that comprises a nucleic acid sequence having at least 90% sequence identity to the nucleic acid sequence of SEQ ID NO: 23;
24) a twenty fourth well that includes a twenty fourth probe, for detecting the presence or absence of Influenza A N1 2009 (N1 CFI), wherein the twenty fourth probe has a nucleic acid sequence that comprises a nucleic acid sequence having at least 90% sequence identity to the nucleic acid sequence of SEQ ID NO: 24;
25) a twenty fifth well that includes a twenty fifth probe, for detecting the presence or absence of Influenza A H1 Seasonal (H1 seasonal CFI), wherein the twenty fifth probe has a nucleic acid sequence that comprises a nucleic acid sequence having at least 90% sequence identity to the nucleic acid sequence of SEQ ID NO: 25;
26) a twenty sixth well that includes a twenty sixth probe, for detecting the presence or absence of Influenza A H3 Seasonal (H3 seasonal CFI), wherein the twenty sixth probe has a nucleic acid sequence that comprises a nucleic acid sequence having at least 90% sequence identity to the nucleic acid sequence of SEQ ID NO: 26;

27) a twenty seventh well that includes a twenty seventh probe, for detecting the presence or absence of Influenza A H5 (H5 CFI), wherein the twenty seventh probe has a nucleic acid sequence that comprises a nucleic acid sequence having at least 90% sequence identity to the nucleic acid sequence of SEQ ID NO: 27;

28) a twenty eighth well that includes a twenty eighth probe, for detecting the presence or absence of Influenza A H7 (H7), wherein the twenty eighth probe has a nucleic acid sequence that comprises a nucleic acid sequence having at least 90% sequence identity to the nucleic acid sequence of SEQ ID NO: 28;

29) a twenty ninth well that includes a twenty ninth probe, for detecting the presence or absence of Influenza A H9 (H9 a), wherein the twenty ninth probe has a nucleic acid sequence that comprises a nucleic acid sequence having at least 90% sequence identity to the nucleic acid sequence of SEQ ID NO: 29;

30) a thirtieth well that includes a thirtieth probe, for detecting the presence or absence of Influenza A H9 (H9 b), wherein the thirtieth probe has a nucleic acid sequence that comprises a nucleic acid sequence having at least 90% sequence identity to the nucleic acid sequence of SEQ ID NO: 30;

31) a thirty first well that includes a thirty first probe, for detecting the presence or absence of Human parainfluenza virus type 1 (HPIV 1 #2), wherein the thirty first probe has a nucleic acid sequence that comprises a nucleic acid sequence having at least 90% sequence identity to the nucleic acid sequence of SEQ ID NO: 31;

32) a thirty second well that includes a thirty second probe, for detecting the presence or absence of Human parainfluenza virus type 3 (HPIV 1 #3), wherein the thirty second probe has a nucleic acid sequence that comprises a nucleic acid sequence having at least 90% sequence identity to the nucleic acid sequence of SEQ ID NO: 32;

33) a thirty third well that includes a thirty third probe, for detecting the presence or absence of Rhinoviruses #2, wherein the thirty third probe has a nucleic acid sequence that comprises a nucleic acid sequence having at least 90% sequence identity to the nucleic acid sequence of SEQ ID NO: 33.

5. The method according to claim 4, wherein the test card comprises each of the additional fourteenth through to thirty third wells and the corresponding fourteenth through to thirty third additional probes.

6. The quantitative method according to claim 5, wherein the test card comprises one or more additional wells and corresponding one or more additional probes selected from:

34) a thirty fourth well that includes a thirty fourth probe, for detecting the presence or absence of *Legionella pneumophilia*, wherein the thirty fourth probe has a nucleic acid sequence that comprises a nucleic acid sequence having at least 90% sequence identity to the nucleic acid sequence of SEQ ID NO: 34;

35) a thirty fifth well that includes a thirty fifth probe, for detecting the presence or absence of *Mycoplasma pneumoniae*, wherein the thirty fifth probe has a nucleic acid sequence that comprises a nucleic acid sequence having at least 90% sequence identity to the nucleic acid sequence of SEQ ID NO: 35;

36) a thirty sixth well that includes a thirty sixth probe, for detecting the presence or absence of *Chlamydiophilia pneumoniae*, wherein the thirty sixth probe has a nucleic acid sequence that comprises a nucleic acid sequence having at least 90% sequence identity to the nucleic acid sequence of SEQ ID NO: 36;

37) a thirty seventh well that includes a thirty seventh probe, for detecting the presence or absence of *Coxiella burnetti*, wherein the thirty seventh probe has a nucleic acid sequence that comprises a nucleic acid sequence having at least 90% sequence identity to the nucleic acid sequence of SEQ ID NO: 37;

38) a thirty eighth well that includes a thirty eighth probe, for detecting the presence or absence of *Chlamydiophilia psittaci*, wherein the thirty eighth probe has a nucleic acid sequence that comprises a nucleic acid sequence having at least 90% sequence identity to the nucleic acid sequence of SEQ ID NO: 38;

39) a thirty ninth well that includes a thirty ninth probe, for detecting the presence or absence of *Chlamydiophilia abortus*, wherein the thirty ninth probe has a nucleic acid sequence that comprises a nucleic acid sequence having at least 90% sequence identity to the nucleic acid sequence of SEQ ID NO: 39).

7. The method according to claim 6, wherein the test card comprises each of the additional thirty third through to thirty ninth wells and the corresponding thirty third through to thirty ninth additional probes.

8. The method according to claim 7, wherein the test card comprises one or more additional control wells and corresponding one or more additional control probes selected from:

1) a fortieth well that includes a fortieth probe, for detecting the presence or absence of Escherichia coli Bacteriophage MS2 (MS2 IC), wherein the fortieth probe has a nucleic acid sequence that comprises a nucleic acid sequence having at least 90% sequence identity to the nucleic acid sequence of SEQ ID NO: 40;

2) a forty first well that includes a forty first probe, for detecting the presence or absence of Human Ribonuclease P gene (RNAse P), wherein the forty first probe has a nucleic acid sequence that comprises a nucleic acid sequence having at least 90% sequence identity to the nucleic acid sequence of SEQ ID NO: 41.

9. The method according to claim 8, wherein the test card comprises one or both of the additional fortieth or forty first well and the corresponding fortieth through forty first additional probes.

10. The method according to claim 1, wherein said method includes a nucleic acid amplification step prior to detection.

11. The quantitative method according to claim 2, wherein the test card further comprises:
an eighth well that includes an eighth probe, for detecting the presence or absence of Human parainfluenza virus type 2 (HPIV 2),wherein the eighth probe has a nucleic acid sequence that comprises the nucleic acid sequence of SEQ ID NO: 131.

12. The quantitative method according to claim 11, wherein the test card further comprises:
a ninth well that includes a ninth probe, for detecting the presence or absence of Human parainfluenza virus type 3 (HPIV 3), wherein the ninth probe has a nucleic acid sequence that comprises a nucleic acid sequence having at least 90% sequence identity to the nucleic acid sequence of SEQ ID NO: 9.

13. The quantitative method according to claim 12, wherein the test card further comprises:
  a tenth well that includes a tenth probe, for detecting the presence or absence of Human parainfluenza virus type 4 (HPIV 4), wherein the tenth probe has a nucleic acid sequence that comprises a nucleic acid sequence having at least 90% sequence identity to the nucleic acid sequence of SEQ ID NO: 10.

14. The quantitative method according to claim 13, wherein the test card further comprises:
  eleventh well that includes an eleventh probe, for detecting the presence or absence of Human Adenoviruses #2, wherein the eleventh probe has a nucleic acid sequence that comprises a nucleic acid sequence having at least 90% sequence identity to the nucleic acid sequence of SEQ ID NO: 11.

15. The quantitative method according to claim 14, wherein the test card further comprises:
  a twelfth well that includes a twelfth probe, for detecting the presence or absence of Tamiflu sensitive Influenza A H1 2009 wherein the twelfth probe has a nucleic acid sequence that comprises a nucleic acid sequence having at least 90% sequence identity to the nucleic acid sequence of SEQ ID NO: 12.

16. The quantitative method according to claim 15, wherein the test card further comprises:
  a thirteenth well that includes a thirteenth probe, for detecting the presence or absence of Tamiflu resistant Influenza A H1 2009, wherein the thirteenth probe has a nucleic acid sequence that comprises a nucleic acid sequence having at least 90% sequence identity to the nucleic acid sequence of SEQ ID NO: 13.

17. The quantitative method according to claim 1, wherein the detectable label and/or the detectable tag comprises a radiolabel, a fluorescent molecule, a coloured molecule, an enzymatic marker or a chromogenic marker.

18. The quantitative method according to claim 1, wherein the detectable label is selected from a group consisting of Fam, a minor groove binder (MGB), digoxygenin, fluorescein-isothiocyanate (FITC), R-phycoerythrin, Alexa 532, and Cy3.

* * * * *

SEQUENCE LISTING

<160> NUMBER OF SEQ ID NOS: 345

<210> SEQ ID NO 1
<211> LENGTH: 10
<212> TYPE: DNA
<213> ORGANISM: Artificial Sequence
<220> FEATURE:
<223> OTHER INFORMATION: Probe

<400> SEQUENCE: 1 ggcaatgcwg

```
<210> SEQ ID NO 2
<211> LENGTH: 10
<212> TYPE: DNA
<213> ORGANISM: Artificial Sequence
<220> FEATURE:
<223> OTHER INFORMATION: Probe

<400> SEQUENCE: 2 gayggggaccr                                                            10

<210> SEQ ID NO 3
<211> LENGTH: 10
<212> TYPE: DNA
<213> ORGANISM: Artificial Sequence
<220> FEATURE:
<223> OTHER INFORMATION: Probe

<400> SEQUENCE: 3
caccagacac                                                             10

<210> SEQ ID NO 4
<211> LENGTH: 10
<212> TYPE: DNA
<213> ORGANISM: Artificial Sequence
<220> FEATURE:
<223> OTHER INFORMATION: Probe

<400> SEQUENCE: 4 ggtcattggr                                                             10

<210> SEQ ID NO 5
<211> LENGTH: 10
<212> TYPE: DNA
<213> ORGANISM: Artificial Sequence
<220> FEATURE:
<223> OTHER INFORMATION: Probe

<400> SEQUENCE: 5
cactgggcac                                                             10

<210> SEQ ID NO 6
<211> LENGTH: 10
<212> TYPE: DNA
<213> ORGANISM: Artificial Sequence
<220> FEATURE:
<223> OTHER INFORMATION: Probe

<400> SEQUENCE: 6 rgtgttcatt                                                             10

<210> SEQ ID NO 7
<211> LENGTH: 10
<212> TYPE: DNA
<213> ORGANISM: Artificial Sequence
<220> FEATURE:
<223> OTHER INFORMATION: Probe

<400> SEQUENCE: 7
tttccagggg                                                             10

<210> SEQ ID NO 8
<211> LENGTH: 10
<212> TYPE: DNA
<213> ORGANISM: Artificial Sequence
<220> FEATURE:
<223> OTHER INFORMATION: Probe
```

```
<400> SEQUENCE: 8
ccgcaagtca                                                          10

<210> SEQ ID NO 9
<211> LENGTH: 10
<212> TYPE: DNA
<213> ORGANISM: Artificial Sequence
<220> FEATURE:
<223> OTHER INFORMATION: Probe

<400> SEQUENCE: 9
ttgcctggtg                                                          10

<210> SEQ ID NO 10
<211> LENGTH: 10
<212> TYPE: DNA
<213> ORGANISM: Artificial Sequence
<220> FEATURE:
<223> OTHER INFORMATION: Probe

<400> SEQUENCE: 10 taargtaggt                                                          10

<210> SEQ ID NO 11
<211> LENGTH: 10
<212> TYPE: DNA
<213> ORGANISM: Artificial Sequence
<220> FEATURE:
<223> OTHER INFORMATION: Probe

<400> SEQUENCE: 11 cggcrtcaty                                                          10

<210> SEQ ID NO 12
<211> LENGTH: 10
<212> TYPE: DNA
<213> ORGANISM: Artificial Sequence
<220> FEATURE:
<223> OTHER INFORMATION: Probe

<400> SEQUENCE: 12 atartgrtaa                                                          10

<210> SEQ ID NO 13
<211> LENGTH: 10
<212> TYPE: DNA
<213> ORGANISM: Artificial Sequence
<220> FEATURE:
<223> OTHER INFORMATION: Probe

<400> SEQUENCE: 13
atagtaataa                                                          10

<210> SEQ ID NO 14
<211> LENGTH: 10
<212> TYPE: DNA
<213> ORGANISM: Artificial Sequence
<220> FEATURE:
<223> OTHER INFORMATION: Probe

<400> SEQUENCE: 14
tactgtgaca                                                          10

<210> SEQ ID NO 15
<211> LENGTH: 10
```

<212> TYPE: DNA
<213> ORGANISM: Artificial Sequence
<220> FEATURE:
<223> OTHER INFORMATION: Probe

<400> SEQUENCE: 15 yrgcggaacc                                                          10

<210> SEQ ID NO 16
<211> LENGTH: 10
<212> TYPE: DNA
<213> ORGANISM: Artificial Sequence
<220> FEATURE:
<223> OTHER INFORMATION: Probe

<400> SEQUENCE: 16
taacgagtgt                                                          10

<210> SEQ ID NO 17
<211> LENGTH: 10
<212> TYPE: DNA
<213> ORGANISM: Artificial Sequence
<220> FEATURE:
<223> OTHER INFORMATION: Probe

<400> SEQUENCE: 17
cgaatgaatg                                                          10

<210> SEQ ID NO 18
<211> LENGTH: 10
<212> TYPE: DNA
<213> ORGANISM: Artificial Sequence
<220> FEATURE:
<223> OTHER INFORMATION: Probe

<400> SEQUENCE: 18 ytctaagcat                                                          10

<210> SEQ ID NO 19
<211> LENGTH: 10
<212> TYPE: DNA
<213> ORGANISM: Artificial Sequence
<220> FEATURE:
<223> OTHER INFORMATION: Probe

<400> SEQUENCE: 19
ttctaagcat                                                          10

<210> SEQ ID NO 20
<211> LENGTH: 10
<212> TYPE: DNA
<213> ORGANISM: Artificial Sequence
<220> FEATURE:
<223> OTHER INFORMATION: Probe

<400> SEQUENCE: 20 gagtayctsa                                                          10

<210> SEQ ID NO 21
<211> LENGTH: 10
<212> TYPE: DNA
<213> ORGANISM: Artificial Sequence
<220> FEATURE:
<223> OTHER INFORMATION: Probe

<400> SEQUENCE: 21
actgcatccg                                                          10

<210> SEQ ID NO 22
<211> LENGTH: 10
<212> TYPE: DNA
<213> ORGANISM: Artificial Sequence
<220> FEATURE:
<223> OTHER INFORMATION: Probe

<400> SEQUENCE: 22
tgtcacctct                                                          10

<210> SEQ ID NO 23
<211> LENGTH: 10
<212> TYPE: DNA
<213> ORGANISM: Artificial Sequence
<220> FEATURE:
<223> OTHER INFORMATION: Probe

<400> SEQUENCE: 23 agtgtgtyac                                                          10

<210> SEQ ID NO 24
<211> LENGTH: 10
<212> TYPE: DNA
<213> ORGANISM: Artificial Sequence
<220> FEATURE:
<223> OTHER INFORMATION: Probe

<400> SEQUENCE: 24
gaatttctgg                                                          10

<210> SEQ ID NO 25
<211> LENGTH: 10
<212> TYPE: DNA
<213> ORGANISM: Artificial Sequence
<220> FEATURE:
<223> OTHER INFORMATION: Probe

<400> SEQUENCE: 25
ttgccggatg                                                          10

<210> SEQ ID NO 26
<211> LENGTH: 10
<212> TYPE: DNA
<213> ORGANISM: Artificial Sequence
<220> FEATURE:
<223> OTHER INFORMATION: Probe

<400> SEQUENCE: 26
cagcaactgt                                                          10

<210> SEQ ID NO 27
<211> LENGTH: 10
<212> TYPE: DNA
<213> ORGANISM: Artificial Sequence
<220> FEATURE:
<223> OTHER INFORMATION: Probe

<400> SEQUENCE: 27
tgctccagaa                                                          10

<210> SEQ ID NO 28
<211> LENGTH: 10
<212> TYPE: DNA
<213> ORGANISM: Artificial Sequence

```
<220> FEATURE:
<223> OTHER INFORMATION: Probe
<220> FEATURE:
<221> NAME/KEY: variation
<222> LOCATION: (2)..(2)
<223> OTHER INFORMATION: n can be any nucleic acid base

<400> SEQUENCE: 28 tngccattgy                                                                10

<210> SEQ ID NO 29
<211> LENGTH: 10
<212> TYPE: DNA
<213> ORGANISM: Artificial Sequence
<220> FEATURE:
<223> OTHER INFORMATION: Probe

<400> SEQUENCE: 29 gtyccgtgra                                                                10

<210> SEQ ID NO 30
<211> LENGTH: 10
<212> TYPE: DNA
<213> ORGANISM: Artificial Sequence
<220> FEATURE:
<223> OTHER INFORMATION: Probe

<400> SEQUENCE: 30 ctggartctg                                                                10

<210> SEQ ID NO 31
<211> LENGTH: 10
<212> TYPE: DNA
<213> ORGANISM: Artificial Sequence
<220> FEATURE:
<223> OTHER INFORMATION: Probe

<400> SEQUENCE: 31 cractgtgtc                                                                10

<210> SEQ ID NO 32
<211> LENGTH: 10
<212> TYPE: DNA
<213> ORGANISM: Artificial Sequence
<220> FEATURE:
<223> OTHER INFORMATION: Probe

<400> SEQUENCE: 32
gtgtcaccgc                                                                10

<210> SEQ ID NO 33
<211> LENGTH: 10
<212> TYPE: DNA
<213> ORGANISM: Artificial Sequence
<220> FEATURE:
<223> OTHER INFORMATION: Probe

<400> SEQUENCE: 33 gayggraccr                                                                10

<210> SEQ ID NO 34
<211> LENGTH: 10
<212> TYPE: DNA
<213> ORGANISM: Artificial Sequence
<220> FEATURE:
<223> OTHER INFORMATION: Probe
```

```
<400> SEQUENCE: 34
aattggcttt                                                          10

<210> SEQ ID NO 35
<211> LENGTH: 10
<212> TYPE: DNA
<213> ORGANISM: Artificial Sequence
<220> FEATURE:
<223> OTHER INFORMATION: Probe

<400> SEQUENCE: 35
ggagagtgtg                                                          10

<210> SEQ ID NO 36
<211> LENGTH: 10
<212> TYPE: DNA
<213> ORGANISM: Artificial Sequence
<220> FEATURE:
<223> OTHER INFORMATION: Probe

<400> SEQUENCE: 36
cagacgctgg                                                          10

<210> SEQ ID NO 37
<211> LENGTH: 10
<212> TYPE: DNA
<213> ORGANISM: Artificial Sequence
<220> FEATURE:
<223> OTHER INFORMATION: Probe

<400> SEQUENCE: 37
cggcgtttat                                                          10

<210> SEQ ID NO 38
<211> LENGTH: 10
<212> TYPE: DNA
<213> ORGANISM: Artificial Sequence
<220> FEATURE:
<223> OTHER INFORMATION: Probe

<400> SEQUENCE: 38
cttggtgtga                                                          10

<210> SEQ ID NO 39
<211> LENGTH: 10
<212> TYPE: DNA
<213> ORGANISM: Artificial Sequence
<220> FEATURE:
<223> OTHER INFORMATION: Probe

<400> SEQUENCE: 39
cttggtgtga                                                          10

<210> SEQ ID NO 40
<211> LENGTH: 10
<212> TYPE: DNA
<213> ORGANISM: Artificial Sequence
<220> FEATURE:
<223> OTHER INFORMATION: Probe

<400> SEQUENCE: 40
agatcaaggt                                                          10

<210> SEQ ID NO 41
<211> LENGTH: 10
```

```
<212> TYPE: DNA
<213> ORGANISM: Artificial Sequence
<220> FEATURE:
<223> OTHER INFORMATION: Probe

<400> SEQUENCE: 41
acctgaaggc                                                          10

<210> SEQ ID NO 42
<211> LENGTH: 15
<212> TYPE: DNA
<213> ORGANISM: Artificial Sequence
<220> FEATURE:
<223> OTHER INFORMATION: Primer

<400> SEQUENCE: 42
aagcwggatt ctacc                                                    15

<210> SEQ ID NO 43
<211> LENGTH: 15
<212> TYPE: DNA
<213> ORGANISM: Artificial Sequence
<220> FEATURE:
<223> OTHER INFORMATION: Primer

<400> SEQUENCE: 43
tcccattatg cctag                                                    15

<210> SEQ ID NO 44
<211> LENGTH: 15
<212> TYPE: DNA
<213> ORGANISM: Artificial Sequence
<220> FEATURE:
<223> OTHER INFORMATION: Primer

<400> SEQUENCE: 44
cctgaatgyg gctaa                                                    15

<210> SEQ ID NO 45
<211> LENGTH: 15
<212> TYPE: DNA
<213> ORGANISM: Artificial Sequence
<220> FEATURE:
<223> OTHER INFORMATION: Primer

<400> SEQUENCE: 45
cggacaccca aagta                                                    15

<210> SEQ ID NO 46
<211> LENGTH: 15
<212> TYPE: DNA
<213> ORGANISM: Artificial Sequence
<220> FEATURE:
<223> OTHER INFORMATION: Primer

<400> SEQUENCE: 46
atcccacaaa aycag                                                    15

<210> SEQ ID NO 47
<211> LENGTH: 15
<212> TYPE: DNA
<213> ORGANISM: Artificial Sequence
<220> FEATURE:
<223> OTHER INFORMATION: Primer

<400> SEQUENCE: 47
```
ctacacataa taara                                                    15

<210> SEQ ID NO 48
<211> LENGTH: 15
<212> TYPE: DNA
<213> ORGANISM: Artificial Sequence
<220> FEATURE:
<223> OTHER INFORMATION: Primer

<400> SEQUENCE: 48
gatgtccatc aagct                                                    15

<210> SEQ ID NO 49
<211> LENGTH: 15
<212> TYPE: DNA
<213> ORGANISM: Artificial Sequence
<220> FEATURE:
<223> OTHER INFORMATION: Primer

<400> SEQUENCE: 49
taragcaata ggtct                                                    15

<210> SEQ ID NO 50
<211> LENGTH: 15
<212> TYPE: DNA
<213> ORGANISM: Artificial Sequence
<220> FEATURE:
<223> OTHER INFORMATION: Primer

<400> SEQUENCE: 50
cctgtcacct ctgac                                                    15

<210> SEQ ID NO 51
<211> LENGTH: 15
<212> TYPE: DNA
<213> ORGANISM: Artificial Sequence
<220> FEATURE:
<223> OTHER INFORMATION: Primer

<400> SEQUENCE: 51
tggacaaakc gtcta                                                    15

<210> SEQ ID NO 52
<211> LENGTH: 15
<212> TYPE: DNA
<213> ORGANISM: Artificial Sequence
<220> FEATURE:
<223> OTHER INFORMATION: Primer

<400> SEQUENCE: 52
ggrtacgctg cagac                                                    15

<210> SEQ ID NO 53
<211> LENGTH: 15
<212> TYPE: DNA
<213> ORGANISM: Artificial Sequence
<220> FEATURE:
<223> OTHER INFORMATION: Primer

<400> SEQUENCE: 53
agtccagaca tctag                                                    15

<210> SEQ ID NO 54
<211> LENGTH: 15
<212> TYPE: DNA
<213> ORGANISM: Artificial Sequence

```
<220> FEATURE:
<223> OTHER INFORMATION: Primer

<400> SEQUENCE: 54
atactcagag accca                                                          15

<210> SEQ ID NO 55
<211> LENGTH: 15
<212> TYPE: DNA
<213> ORGANISM: Artificial Sequence
<220> FEATURE:
<223> OTHER INFORMATION: Primer

<400> SEQUENCE: 55
ataytgttgc atagc                                                          15

<210> SEQ ID NO 56
<211> LENGTH: 15
<212> TYPE: DNA
<213> ORGANISM: Artificial Sequence
<220> FEATURE:
<223> OTHER INFORMATION: Primer

<400> SEQUENCE: 56
tgctcctgat carcc                                                          15

<210> SEQ ID NO 57
<211> LENGTH: 15
<212> TYPE: DNA
<213> ORGANISM: Artificial Sequence
<220> FEATURE:
<223> OTHER INFORMATION: Primer

<400> SEQUENCE: 57
tcccaccatr gcata                                                          15

<210> SEQ ID NO 58
<211> LENGTH: 15
<212> TYPE: DNA
<213> ORGANISM: Artificial Sequence
<220> FEATURE:
<223> OTHER INFORMATION: Primer

<400> SEQUENCE: 58
tatcctcaga gatcc                                                          15

<210> SEQ ID NO 59
<211> LENGTH: 15
<212> TYPE: DNA
<213> ORGANISM: Artificial Sequence
<220> FEATURE:
<223> OTHER INFORMATION: Primer

<400> SEQUENCE: 59
acatactgtt gcatg                                                          15

<210> SEQ ID NO 60
<211> LENGTH: 15
<212> TYPE: DNA
<213> ORGANISM: Artificial Sequence
<220> FEATURE:
<223> OTHER INFORMATION: Primer

<400> SEQUENCE: 60
cttgtacagg aratg                                                          15
```

```
<210> SEQ ID NO 61
<211> LENGTH: 15
<212> TYPE: DNA
<213> ORGANISM: Artificial Sequence
<220> FEATURE:
<223> OTHER INFORMATION: Primer

<400> SEQUENCE: 61
tcccaccatr gcata                                                        15

<210> SEQ ID NO 62
<211> LENGTH: 15
<212> TYPE: DNA
<213> ORGANISM: Artificial Sequence
<220> FEATURE:
<223> OTHER INFORMATION: Primer

<400> SEQUENCE: 62
rgtsgayccc atgga                                                        15

<210> SEQ ID NO 63
<211> LENGTH: 15
<212> TYPE: DNA
<213> ORGANISM: Artificial Sequence
<220> FEATURE:
<223> OTHER INFORMATION: Primer

<400> SEQUENCE: 63
sggygtrcgs aggta                                                        15

<210> SEQ ID NO 64
<211> LENGTH: 15
<212> TYPE: DNA
<213> ORGANISM: Artificial Sequence
<220> FEATURE:
<223> OTHER INFORMATION: Primer

<400> SEQUENCE: 64
agtcaaatca gtcga                                                        15

<210> SEQ ID NO 65
<211> LENGTH: 15
<212> TYPE: DNA
<213> ORGANISM: Artificial Sequence
<220> FEATURE:
<223> OTHER INFORMATION: Primer

<400> SEQUENCE: 65
ccctgcayac acatg                                                        15

<210> SEQ ID NO 66
<211> LENGTH: 15
<212> TYPE: DNA
<213> ORGANISM: Artificial Sequence
<220> FEATURE:
<223> OTHER INFORMATION: Primer

<400> SEQUENCE: 66
agtcaaatca gtcga                                                        15

<210> SEQ ID NO 67
<211> LENGTH: 15
<212> TYPE: DNA
<213> ORGANISM: Artificial Sequence
<220> FEATURE:
<223> OTHER INFORMATION: Primer
```

```
<400> SEQUENCE: 67
ccctgcayac acatg                                                          15

<210> SEQ ID NO 68
<211> LENGTH: 15
<212> TYPE: DNA
<213> ORGANISM: Artificial Sequence
<220> FEATURE:
<223> OTHER INFORMATION: Primer

<400> SEQUENCE: 68
catctgytta acaag                                                          15

<210> SEQ ID NO 69
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (5)..(5)
<223> OTHER INFORMATION: n is inosine

<400> SEQUENCE: 69
aaganactga tcctg                                                          15

<210> SEQ ID NO 70
<211> LENGTH: 15
<212> TYPE: DNA
<213> ORGANISM: Artificial Sequence
<220> FEATURE:
<223> OTHER INFORMATION: Primer

<400> SEQUENCE: 70
cctgaatgyg gctaa                                                          15

<210> SEQ ID NO 71
<211> LENGTH: 15
<212> TYPE: DNA
<213> ORGANISM: Artificial Sequence
<220> FEATURE:
<223> OTHER INFORMATION: Primer

<400> SEQUENCE: 71
cggacaccca aagta                                                          15

<210> SEQ ID NO 72
<211> LENGTH: 15
<212> TYPE: DNA
<213> ORGANISM: Artificial Sequence
<220> FEATURE:
<223> OTHER INFORMATION: Primer

<400> SEQUENCE: 72
ttatccaaaa tgtga                                                          15

<210> SEQ ID NO 73
<211> LENGTH: 15
<212> TYPE: DNA
<213> ORGANISM: Artificial Sequence
<220> FEATURE:
<223> OTHER INFORMATION: Primer

<400> SEQUENCE: 73
```
gcatcaccgg atgat                                                        15

<210> SEQ ID NO 74
<211> LENGTH: 15
<212> TYPE: DNA
<213> ORGANISM: Artificial Sequence
<220> FEATURE:
<223> OTHER INFORMATION: Primer

<400> SEQUENCE: 74
ttatcctaar tgtga                                                        15

<210> SEQ ID NO 75
<211> LENGTH: 15
<212> TYPE: DNA
<213> ORGANISM: Artificial Sequence
<220> FEATURE:
<223> OTHER INFORMATION: Primer

<400> SEQUENCE: 75
atcaccactr ctagt                                                        15

<210> SEQ ID NO 76
<211> LENGTH: 15
<212> TYPE: DNA
<213> ORGANISM: Artificial Sequence
<220> FEATURE:
<223> OTHER INFORMATION: Primer

<400> SEQUENCE: 76
ttatcccaaa tgtga                                                        15

<210> SEQ ID NO 77
<211> LENGTH: 15
<212> TYPE: DNA
<213> ORGANISM: Artificial Sequence
<220> FEATURE:
<223> OTHER INFORMATION: Primer

<400> SEQUENCE: 77
agcrtcacca gaagt                                                        15

<210> SEQ ID NO 78
<211> LENGTH: 15
<212> TYPE: DNA
<213> ORGANISM: Artificial Sequence
<220> FEATURE:
<223> OTHER INFORMATION: Primer

<400> SEQUENCE: 78
ctatcctaag tgtga                                                        15

<210> SEQ ID NO 79
<211> LENGTH: 15
<212> TYPE: DNA
<213> ORGANISM: Artificial Sequence
<220> FEATURE:
<223> OTHER INFORMATION: Primer

<400> SEQUENCE: 79
tgcatcacca gaagt                                                        15

<210> SEQ ID NO 80
<211> LENGTH: 15
<212> TYPE: DNA
<213> ORGANISM: Artificial Sequence

```
<220> FEATURE:
<223> OTHER INFORMATION: Primer
<220> FEATURE:
<221> NAME/KEY: variation
<222> LOCATION: (3)..(3)
<223> OTHER INFORMATION: n can be any nucleic acid base

<400> SEQUENCE: 80
kcntacatgc acatc                                                    15

<210> SEQ ID NO 81
<211> LENGTH: 15
<212> TYPE: DNA
<213> ORGANISM: Artificial Sequence
<220> FEATURE:
<223> OTHER INFORMATION: Primer

<400> SEQUENCE: 81
gggrttyctr aactt                                                    15

<210> SEQ ID NO 82
<211> LENGTH: 15
<212> TYPE: DNA
<213> ORGANISM: Artificial Sequence
<220> FEATURE:
<223> OTHER INFORMATION: Primer

<400> SEQUENCE: 82
caggaartga cgtat                                                    15

<210> SEQ ID NO 83
<211> LENGTH: 15
<212> TYPE: DNA
<213> ORGANISM: Artificial Sequence
<220> FEATURE:
<223> OTHER INFORMATION: Primer

<400> SEQUENCE: 83
tgttcactcg ccgga                                                    15

<210> SEQ ID NO 84
<211> LENGTH: 15
<212> TYPE: DNA
<213> ORGANISM: Artificial Sequence
<220> FEATURE:
<223> OTHER INFORMATION: Primer

<400> SEQUENCE: 84
mgaggtcgaa acgta                                                    15

<210> SEQ ID NO 85
<211> LENGTH: 15
<212> TYPE: DNA
<213> ORGANISM: Artificial Sequence
<220> FEATURE:
<223> OTHER INFORMATION: Primer

<400> SEQUENCE: 85
cacggtgagc gtraa                                                    15

<210> SEQ ID NO 86
<211> LENGTH: 15
<212> TYPE: DNA
<213> ORGANISM: Artificial Sequence
<220> FEATURE:
<223> OTHER INFORMATION: Primer
```

```
<400> SEQUENCE: 86
tgtagacaca gtact                                                  15

<210> SEQ ID NO 87
<211> LENGTH: 15
<212> TYPE: DNA
<213> ORGANISM: Artificial Sequence
<220> FEATURE:
<223> OTHER INFORMATION: Primer

<400> SEQUENCE: 87
atgcttgtct tctag                                                  15

<210> SEQ ID NO 88
<211> LENGTH: 15
<212> TYPE: DNA
<213> ORGANISM: Artificial Sequence
<220> FEATURE:
<223> OTHER INFORMATION: Primer

<400> SEQUENCE: 88
atcagttggc taaca                                                  15

<210> SEQ ID NO 89
<211> LENGTH: 15
<212> TYPE: DNA
<213> ORGANISM: Artificial Sequence
<220> FEATURE:
<223> OTHER INFORMATION: Primer

<400> SEQUENCE: 89
agccactgcc ccatt                                                  15

<210> SEQ ID NO 90
<211> LENGTH: 15
<212> TYPE: DNA
<213> ORGANISM: Artificial Sequence
<220> FEATURE:
<223> OTHER INFORMATION: Primer

<400> SEQUENCE: 90
gcccccctac aattg                                                  15

<210> SEQ ID NO 91
<211> LENGTH: 15
<212> TYPE: DNA
<213> ORGANISM: Artificial Sequence
<220> FEATURE:
<223> OTHER INFORMATION: Primer

<400> SEQUENCE: 91
attctgggtt tccta                                                  15

<210> SEQ ID NO 92
<211> LENGTH: 15
<212> TYPE: DNA
<213> ORGANISM: Artificial Sequence
<220> FEATURE:
<223> OTHER INFORMATION: Primer

<400> SEQUENCE: 92
tgttgaacgc agcaa                                                  15

<210> SEQ ID NO 93
<211> LENGTH: 15
```

```
<212> TYPE: DNA
<213> ORGANISM: Artificial Sequence
<220> FEATURE:
<223> OTHER INFORMATION: Primer

<400> SEQUENCE: 93
gcaactagtg accta                                                    15

<210> SEQ ID NO 94
<211> LENGTH: 15
<212> TYPE: DNA
<213> ORGANISM: Artificial Sequence
<220> FEATURE:
<223> OTHER INFORMATION: Primer

<400> SEQUENCE: 94
atgatgcmat maayt                                                    15

<210> SEQ ID NO 95
<211> LENGTH: 15
<212> TYPE: DNA
<213> ORGANISM: Artificial Sequence
<220> FEATURE:
<223> OTHER INFORMATION: Primer

<400> SEQUENCE: 95
ccattggagt ttgac                                                    15

<210> SEQ ID NO 96
<211> LENGTH: 15
<212> TYPE: DNA
<213> ORGANISM: Artificial Sequence
<220> FEATURE:
<223> OTHER INFORMATION: Primer

<400> SEQUENCE: 96
cttcggggcr tcatg                                                    15

<210> SEQ ID NO 97
<211> LENGTH: 15
<212> TYPE: DNA
<213> ORGANISM: Artificial Sequence
<220> FEATURE:
<223> OTHER INFORMATION: Primer

<400> SEQUENCE: 97
cygcatgttt ccrtt                                                    15

<210> SEQ ID NO 98
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)..(1)
<223> OTHER INFORMATION: n is inosine

<400> SEQUENCE: 98
nggyyaccar tcaac                                                    15

<210> SEQ ID NO 99
<211> LENGTH: 15
<212> TYPE: DNA
<213> ORGANISM: Artificial Sequence
<220> FEATURE:
```

```
<223> OTHER INFORMATION: Primer

<400> SEQUENCE: 99
yarcatycca ttgtg                                                    15

<210> SEQ ID NO 100
<211> LENGTH: 15
<212> TYPE: DNA
<213> ORGANISM: Artificial Sequence
<220> FEATURE:
<223> OTHER INFORMATION: Primer

<400> SEQUENCE: 100
ygaycartgc atgga                                                    15

<210> SEQ ID NO 101
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (10)..(10)
<223> OTHER INFORMATION: n is inosine

<400> SEQUENCE: 101
ggcracagtn gaata                                                    15

<210> SEQ ID NO 102
<211> LENGTH: 15
<212> TYPE: DNA
<213> ORGANISM: Artificial Sequence
<220> FEATURE:
<223> OTHER INFORMATION: Primer

<400> SEQUENCE: 102
ggatggaacc gtyaa                                                    15

<210> SEQ ID NO 103
<211> LENGTH: 15
<212> TYPE: DNA
<213> ORGANISM: Artificial Sequence
<220> FEATURE:
<223> OTHER INFORMATION: Primer

<400> SEQUENCE: 103
ttgttgtgac ctcat                                                    15

<210> SEQ ID NO 104
<211> LENGTH: 15
<212> TYPE: DNA
<213> ORGANISM: Artificial Sequence
<220> FEATURE:
<223> OTHER INFORMATION: Primer

<400> SEQUENCE: 104
rgctttcaga caaga                                                    15

<210> SEQ ID NO 105
<211> LENGTH: 15
<212> TYPE: DNA
<213> ORGANISM: Artificial Sequence
<220> FEATURE:
<223> OTHER INFORMATION: Primer

<400> SEQUENCE: 105
```

```
gaccgcatga ttgac                                                   15

<210> SEQ ID NO 106
<211> LENGTH: 15
<212> TYPE: DNA
<213> ORGANISM: Artificial Sequence
<220> FEATURE:
<223> OTHER INFORMATION: Primer

<400> SEQUENCE: 106
cctgaatgyg gctaa                                                   15

<210> SEQ ID NO 107
<211> LENGTH: 15
<212> TYPE: DNA
<213> ORGANISM: Artificial Sequence
<220> FEATURE:
<223> OTHER INFORMATION: Primer

<400> SEQUENCE: 107
cggacaccca aagta                                                   15

<210> SEQ ID NO 108
<211> LENGTH: 15
<212> TYPE: DNA
<213> ORGANISM: Artificial Sequence
<220> FEATURE:
<223> OTHER INFORMATION: Primer

<400> SEQUENCE: 108
atgcaagacg ctatg                                                   15

<210> SEQ ID NO 109
<211> LENGTH: 15
<212> TYPE: DNA
<213> ORGANISM: Artificial Sequence
<220> FEATURE:
<223> OTHER INFORMATION: Primer

<400> SEQUENCE: 109
gtctttcatt tgctg                                                   15

<210> SEQ ID NO 110
<211> LENGTH: 15
<212> TYPE: DNA
<213> ORGANISM: Artificial Sequence
<220> FEATURE:
<223> OTHER INFORMATION: Primer

<400> SEQUENCE: 110
gtggcagttg ggtca                                                   15

<210> SEQ ID NO 111
<211> LENGTH: 15
<212> TYPE: DNA
<213> ORGANISM: Artificial Sequence
<220> FEATURE:
<223> OTHER INFORMATION: Primer

<400> SEQUENCE: 111
cttgatccgc ccaca                                                   15

<210> SEQ ID NO 112
<211> LENGTH: 15
<212> TYPE: DNA
```

```
<213> ORGANISM: Artificial Sequence
<220> FEATURE:
<223> OTHER INFORMATION: Primer

<400> SEQUENCE: 112
tataaaggcg ttgct                                              15

<210> SEQ ID NO 113
<211> LENGTH: 15
<212> TYPE: DNA
<213> ORGANISM: Artificial Sequence
<220> FEATURE:
<223> OTHER INFORMATION: Primer

<400> SEQUENCE: 113
gatggtcgca gactt                                              15

<210> SEQ ID NO 114
<211> LENGTH: 15
<212> TYPE: DNA
<213> ORGANISM: Artificial Sequence
<220> FEATURE:
<223> OTHER INFORMATION: Primer

<400> SEQUENCE: 114
catcgttccc ggcag                                              15

<210> SEQ ID NO 115
<211> LENGTH: 15
<212> TYPE: DNA
<213> ORGANISM: Artificial Sequence
<220> FEATURE:
<223> OTHER INFORMATION: Primer

<400> SEQUENCE: 115
gtttactaat cccca                                              15

<210> SEQ ID NO 116
<211> LENGTH: 15
<212> TYPE: DNA
<213> ORGANISM: Artificial Sequence
<220> FEATURE:
<223> OTHER INFORMATION: Primer

<400> SEQUENCE: 116
tgggaaggtg cttca                                              15

<210> SEQ ID NO 117
<211> LENGTH: 15
<212> TYPE: DNA
<213> ORGANISM: Artificial Sequence
<220> FEATURE:
<223> OTHER INFORMATION: Primer

<400> SEQUENCE: 117
cgcggatgct aatgg                                              15

<210> SEQ ID NO 118
<211> LENGTH: 15
<212> TYPE: DNA
<213> ORGANISM: Artificial Sequence
<220> FEATURE:
<223> OTHER INFORMATION: Primer

<400> SEQUENCE: 118
tgggaaggtg cttca                                              15
```

<210> SEQ ID NO 119
<211> LENGTH: 15
<212> TYPE: DNA
<213> ORGANISM: Artificial Sequence
<220> FEATURE:
<223> OTHER INFORMATION: Primer

<400> SEQUENCE: 119
tcctgcgcgg atgct                                                    15

<210> SEQ ID NO 120
<211> LENGTH: 15
<212> TYPE: DNA
<213> ORGANISM: Artificial Sequence
<220> FEATURE:
<223> OTHER INFORMATION: Primer

<400> SEQUENCE: 120
ctctccgtat tcacg                                                    15

<210> SEQ ID NO 121
<211> LENGTH: 14
<212> TYPE: DNA
<213> ORGANISM: Artificial Sequence
<220> FEATURE:
<223> OTHER INFORMATION: Primer

<400> SEQUENCE: 121
gaccccacga tgac                                                     14

<210> SEQ ID NO 122
<211> LENGTH: 15
<212> TYPE: DNA
<213> ORGANISM: Artificial Sequence
<220> FEATURE:
<223> OTHER INFORMATION: Primer

<400> SEQUENCE: 122
ttggacctgc gagcg                                                    15

<210> SEQ ID NO 123
<211> LENGTH: 15
<212> TYPE: DNA
<213> ORGANISM: Artificial Sequence
<220> FEATURE:
<223> OTHER INFORMATION: Primer

<400> SEQUENCE: 123
gctgtctcca caagt                                                    15

<210> SEQ ID NO 124
<211> LENGTH: 13
<212> TYPE: DNA
<213> ORGANISM: Artificial Sequence
<220> FEATURE:
<223> OTHER INFORMATION: Probe

<400> SEQUENCE: 124
taggcaatgc wgc                                                      13

<210> SEQ ID NO 125
<211> LENGTH: 19
<212> TYPE: DNA
<213> ORGANISM: Artificial Sequence
<220> FEATURE:

<223> OTHER INFORMATION: Probe

<400> SEQUENCE: 125
tcygggaygg gaccracta                                                  19

<210> SEQ ID NO 126
<211> LENGTH: 17
<212> TYPE: DNA
<213> ORGANISM: Artificial Sequence
<220> FEATURE:
<223> OTHER INFORMATION: Probe

<400> SEQUENCE: 126
tcagcaccag acacacc                                                    17

<210> SEQ ID NO 127
<211> LENGTH: 16
<212> TYPE: DNA
<213> ORGANISM: Artificial Sequence
<220> FEATURE:
<223> OTHER INFORMATION: Probe

<400> SEQUENCE: 127
tctggtcatt ggrgcc                                                     16

<210> SEQ ID NO 128
<211> LENGTH: 17
<212> TYPE: DNA
<213> ORGANISM: Artificial Sequence
<220> FEATURE:
<223> OTHER INFORMATION: Probe

<400> SEQUENCE: 128
cgctcactgg gcacggt                                                    17

<210> SEQ ID NO 129
<211> LENGTH: 19
<212> TYPE: DNA
<213> ORGANISM: Artificial Sequence
<220> FEATURE:
<223> OTHER INFORMATION: Probe

<400> SEQUENCE: 129
aactgrgtgt tcattttgt                                                  19

<210> SEQ ID NO 130
<211> LENGTH: 18
<212> TYPE: DNA
<213> ORGANISM: Artificial Sequence
<220> FEATURE:
<223> OTHER INFORMATION: Probe

<400> SEQUENCE: 130
atartttcca ggggcaaa                                                   18

<210> SEQ ID NO 131
<211> LENGTH: 17
<212> TYPE: DNA
<213> ORGANISM: Artificial Sequence
<220> FEATURE:
<223> OTHER INFORMATION: Probe

<400> SEQUENCE: 131
ccatccgcaa gtcaatg                                                    17

```
<210> SEQ ID NO 132
<211> LENGTH: 18
<212> TYPE: DNA
<213> ORGANISM: Artificial Sequence
<220> FEATURE:
<223> OTHER INFORMATION: Probe

<400> SEQUENCE: 132
atagttgcct ggtgcgaa                                                 18

<210> SEQ ID NO 133
<211> LENGTH: 18
<212> TYPE: DNA
<213> ORGANISM: Artificial Sequence
<220> FEATURE:
<223> OTHER INFORMATION: Probe

<400> SEQUENCE: 133
ctgataargt aggtgctt                                                 18

<210> SEQ ID NO 134
<211> LENGTH: 14
<212> TYPE: DNA
<213> ORGANISM: Artificial Sequence
<220> FEATURE:
<223> OTHER INFORMATION: Probe

<400> SEQUENCE: 134
cgcggcrtca tyga                                                     14

<210> SEQ ID NO 135
<211> LENGTH: 18
<212> TYPE: DNA
<213> ORGANISM: Artificial Sequence
<220> FEATURE:
<223> OTHER INFORMATION: Probe

<400> SEQUENCE: 135
cctcatartg rtaattag                                                 18

<210> SEQ ID NO 136
<211> LENGTH: 18
<212> TYPE: DNA
<213> ORGANISM: Artificial Sequence
<220> FEATURE:
<223> OTHER INFORMATION: Probe

<400> SEQUENCE: 136
cctcatagta ataattag                                                 18

<210> SEQ ID NO 137
<211> LENGTH: 18
<212> TYPE: DNA
<213> ORGANISM: Artificial Sequence
<220> FEATURE:
<223> OTHER INFORMATION: Probe

<400> SEQUENCE: 137
atggtactgt gacaatgc                                                 18

<210> SEQ ID NO 138
<211> LENGTH: 18
<212> TYPE: DNA
<213> ORGANISM: Artificial Sequence
<220> FEATURE:
<223> OTHER INFORMATION: Probe
```

```
<400> SEQUENCE: 138
tctgyrgcgg aaccgact                                                 18

<210> SEQ ID NO 139
<211> LENGTH: 16
<212> TYPE: DNA
<213> ORGANISM: Artificial Sequence
<220> FEATURE:
<223> OTHER INFORMATION: Probe

<400> SEQUENCE: 139
agctaacgag tgtgcg                                                   16

<210> SEQ ID NO 140
<211> LENGTH: 17
<212> TYPE: DNA
<213> ORGANISM: Artificial Sequence
<220> FEATURE:
<223> OTHER INFORMATION: Probe

<400> SEQUENCE: 140
cttgcgaatg aatgygc                                                  17

<210> SEQ ID NO 141
<211> LENGTH: 19
<212> TYPE: DNA
<213> ORGANISM: Artificial Sequence
<220> FEATURE:
<223> OTHER INFORMATION: Probe

<400> SEQUENCE: 141
ttgggytcta agcatgtta                                                19

<210> SEQ ID NO 142
<211> LENGTH: 19
<212> TYPE: DNA
<213> ORGANISM: Artificial Sequence
<220> FEATURE:
<223> OTHER INFORMATION: Probe

<400> SEQUENCE: 142
ttaggttcta agcatgtca                                                19

<210> SEQ ID NO 143
<211> LENGTH: 19
<212> TYPE: DNA
<213> ORGANISM: Artificial Sequence
<220> FEATURE:
<223> OTHER INFORMATION: Probe

<400> SEQUENCE: 143
cytcggagta yctsagycc                                                19

<210> SEQ ID NO 144
<211> LENGTH: 18
<212> TYPE: DNA
<213> ORGANISM: Artificial Sequence
<220> FEATURE:
<223> OTHER INFORMATION: Probe

<400> SEQUENCE: 144
tcagactgca tccggtct                                                 18

<210> SEQ ID NO 145
<211> LENGTH: 16
```

```
<212> TYPE: DNA
<213> ORGANISM: Artificial Sequence
<220> FEATURE:
<223> OTHER INFORMATION: Probe

<400> SEQUENCE: 145
tcytgtcacc tctgac                                              16

<210> SEQ ID NO 146
<211> LENGTH: 17
<212> TYPE: DNA
<213> ORGANISM: Artificial Sequence
<220> FEATURE:
<223> OTHER INFORMATION: Probe

<400> SEQUENCE: 146
acagagtgtg tyactgt                                             17

<210> SEQ ID NO 147
<211> LENGTH: 16
<212> TYPE: DNA
<213> ORGANISM: Artificial Sequence
<220> FEATURE:
<223> OTHER INFORMATION: Probe

<400> SEQUENCE: 147
ttggaatttc tggccc                                              16

<210> SEQ ID NO 148
<211> LENGTH: 14
<212> TYPE: DNA
<213> ORGANISM: Artificial Sequence
<220> FEATURE:
<223> OTHER INFORMATION: Probe

<400> SEQUENCE: 148
cgttgccgga tgga                                                14

<210> SEQ ID NO 149
<211> LENGTH: 18
<212> TYPE: DNA
<213> ORGANISM: Artificial Sequence
<220> FEATURE:
<223> OTHER INFORMATION: Probe

<400> SEQUENCE: 149
cctacagcaa ctgttacc                                            18

<210> SEQ ID NO 150
<211> LENGTH: 16
<212> TYPE: DNA
<213> ORGANISM: Artificial Sequence
<220> FEATURE:
<223> OTHER INFORMATION: Probe

<400> SEQUENCE: 150
cattgctcca gaawat                                              16

<210> SEQ ID NO 151
<211> LENGTH: 15
<212> TYPE: DNA
<213> ORGANISM: Artificial Sequence
<220> FEATURE:
<223> OTHER INFORMATION: Probe
<220> FEATURE:
<221> NAME/KEY: variation
<222> LOCATION: (5)..(5)
```

<223> OTHER INFORMATION: n can be any nucleic acid base

<400> SEQUENCE: 151
ttctngccat tgyaa                                                         15

<210> SEQ ID NO 152
<211> LENGTH: 18
<212> TYPE: DNA
<213> ORGANISM: Artificial Sequence
<220> FEATURE:
<223> OTHER INFORMATION: Probe

<400> SEQUENCE: 152
caatgtycct gtracaca                                                      18

<210> SEQ ID NO 153
<211> LENGTH: 16
<212> TYPE: DNA
<213> ORGANISM: Artificial Sequence
<220> FEATURE:
<223> OTHER INFORMATION: Probe

<400> SEQUENCE: 153
aarctggart ctgarg                                                        16

<210> SEQ ID NO 154
<211> LENGTH: 17
<212> TYPE: DNA
<213> ORGANISM: Artificial Sequence
<220> FEATURE:
<223> OTHER INFORMATION: Probe

<400> SEQUENCE: 154
ccttcractg tgtctcc                                                       17

<210> SEQ ID NO 155
<211> LENGTH: 17
<212> TYPE: DNA
<213> ORGANISM: Artificial Sequence
<220> FEATURE:
<223> OTHER INFORMATION: Probe

<400> SEQUENCE: 155
cactgtgtca ccgctca                                                       17

<210> SEQ ID NO 156
<211> LENGTH: 19
<212> TYPE: DNA
<213> ORGANISM: Artificial Sequence
<220> FEATURE:
<223> OTHER INFORMATION: Probe

<400> SEQUENCE: 156
tcyggsaygg raccracta                                                     19

<210> SEQ ID NO 157
<211> LENGTH: 19
<212> TYPE: DNA
<213> ORGANISM: Artificial Sequence
<220> FEATURE:
<223> OTHER INFORMATION: Probe

<400> SEQUENCE: 157
cgctcaattg gctttaacc                                                     19

```
<210> SEQ ID NO 158
<211> LENGTH: 15
<212> TYPE: DNA
<213> ORGANISM: Artificial Sequence
<220> FEATURE:
<223> OTHER INFORMATION: Probe

<400> SEQUENCE: 158
cgtggagagt gtgtg                                                      15

<210> SEQ ID NO 159
<211> LENGTH: 15
<212> TYPE: DNA
<213> ORGANISM: Artificial Sequence
<220> FEATURE:
<223> OTHER INFORMATION: Probe

<400> SEQUENCE: 159
caacagacgc tggcg                                                      15

<210> SEQ ID NO 160
<211> LENGTH: 16
<212> TYPE: DNA
<213> ORGANISM: Artificial Sequence
<220> FEATURE:
<223> OTHER INFORMATION: Probe

<400> SEQUENCE: 160
tgtcggcgtt tattgg                                                     16

<210> SEQ ID NO 161
<211> LENGTH: 16
<212> TYPE: DNA
<213> ORGANISM: Artificial Sequence
<220> FEATURE:
<223> OTHER INFORMATION: Probe

<400> SEQUENCE: 161
ctacttggtg tgaygc                                                     16

<210> SEQ ID NO 162
<211> LENGTH: 16
<212> TYPE: DNA
<213> ORGANISM: Artificial Sequence
<220> FEATURE:
<223> OTHER INFORMATION: Probe

<400> SEQUENCE: 162
ctacttggtg tgaygc                                                     16

<210> SEQ ID NO 163
<211> LENGTH: 19
<212> TYPE: DNA
<213> ORGANISM: Artificial Sequence
<220> FEATURE:
<223> OTHER INFORMATION: Probe

<400> SEQUENCE: 163
tcgatagatc aaggtgcct                                                  19

<210> SEQ ID NO 164
<211> LENGTH: 19
<212> TYPE: DNA
<213> ORGANISM: Artificial Sequence
<220> FEATURE:
<223> OTHER INFORMATION: Probe
```

```
<400> SEQUENCE: 164
ttctgacctg aaggctctg                                            19

<210> SEQ ID NO 165
<211> LENGTH: 23
<212> TYPE: DNA
<213> ORGANISM: Artificial Sequence
<220> FEATURE:
<223> OTHER INFORMATION: Primer

<400> SEQUENCE: 165
gggwggwgaa gcwggattct acc                                       23

<210> SEQ ID NO 166
<211> LENGTH: 27
<212> TYPE: DNA
<213> ORGANISM: Artificial Sequence
<220> FEATURE:
<223> OTHER INFORMATION: Primer

<400> SEQUENCE: 166
acctctrtac tctcccatta tgcctag                                   27

<210> SEQ ID NO 167
<211> LENGTH: 20
<212> TYPE: DNA
<213> ORGANISM: Artificial Sequence
<220> FEATURE:
<223> OTHER INFORMATION: Primer

<400> SEQUENCE: 167
cggcccctga atgyggctaa                                           20

<210> SEQ ID NO 168
<211> LENGTH: 21
<212> TYPE: DNA
<213> ORGANISM: Artificial Sequence
<220> FEATURE:
<223> OTHER INFORMATION: Primer

<400> SEQUENCE: 168
gaaacacgga cacccaaagt a                                         21

<210> SEQ ID NO 169
<211> LENGTH: 26
<212> TYPE: DNA
<213> ORGANISM: Artificial Sequence
<220> FEATURE:
<223> OTHER INFORMATION: Primer

<400> SEQUENCE: 169
catcaggtaa yatcccacaa aaycag                                    26

<210> SEQ ID NO 170
<211> LENGTH: 31
<212> TYPE: DNA
<213> ORGANISM: Artificial Sequence
<220> FEATURE:
<223> OTHER INFORMATION: Primer

<400> SEQUENCE: 170
gtgaatatta argcacctac acataataar a                              31

<210> SEQ ID NO 171
<211> LENGTH: 23
```

```
<212> TYPE: DNA
<213> ORGANISM: Artificial Sequence
<220> FEATURE:
<223> OTHER INFORMATION: Primer

<400> SEQUENCE: 171
gcagctctga tgtccatcaa gct                                            23

<210> SEQ ID NO 172
<211> LENGTH: 28
<212> TYPE: DNA
<213> ORGANISM: Artificial Sequence
<220> FEATURE:
<223> OTHER INFORMATION: Primer

<400> SEQUENCE: 172
cagcttgctt gcttaragca ataggtct                                       28

<210> SEQ ID NO 173
<211> LENGTH: 22
<212> TYPE: DNA
<213> ORGANISM: Artificial Sequence
<220> FEATURE:
<223> OTHER INFORMATION: Primer

<400> SEQUENCE: 173
gaccratcct gtcacctctg ac                                             22

<210> SEQ ID NO 174
<211> LENGTH: 24
<212> TYPE: DNA
<213> ORGANISM: Artificial Sequence
<220> FEATURE:
<223> OTHER INFORMATION: Primer

<400> SEQUENCE: 174
agggcattyt ggacaaakcg tcta                                           24

<210> SEQ ID NO 175
<211> LENGTH: 18
<212> TYPE: DNA
<213> ORGANISM: Artificial Sequence
<220> FEATURE:
<223> OTHER INFORMATION: Primer

<400> SEQUENCE: 175
agtggrtacg ctgcagac                                                  18

<210> SEQ ID NO 176
<211> LENGTH: 28
<212> TYPE: DNA
<213> ORGANISM: Artificial Sequence
<220> FEATURE:
<223> OTHER INFORMATION: Primer

<400> SEQUENCE: 176
gttcagcatt ataagtccag acatctag                                       28

<210> SEQ ID NO 177
<211> LENGTH: 30
<212> TYPE: DNA
<213> ORGANISM: Artificial Sequence
<220> FEATURE:
<223> OTHER INFORMATION: Primer

<400> SEQUENCE: 177
```

```
gcyccttya tatgtatact cagagaccca                               30

<210> SEQ ID NO 178
<211> LENGTH: 30
<212> TYPE: DNA
<213> ORGANISM: Artificial Sequence
<220> FEATURE:
<223> OTHER INFORMATION: Primer

<400> SEQUENCE: 178
tgttcttcca gttacatayt gttgcatagc                              30

<210> SEQ ID NO 179
<211> LENGTH: 26
<212> TYPE: DNA
<213> ORGANISM: Artificial Sequence
<220> FEATURE:
<223> OTHER INFORMATION: Primer

<400> SEQUENCE: 179
aagtgyatga ctgctcctga tcarcc                                  26

<210> SEQ ID NO 180
<211> LENGTH: 26
<212> TYPE: DNA
<213> ORGANISM: Artificial Sequence
<220> FEATURE:
<223> OTHER INFORMATION: Primer

<400> SEQUENCE: 180
ttgccaatrt ctcccaccat rgcata                                  26

<210> SEQ ID NO 181
<211> LENGTH: 29
<212> TYPE: DNA
<213> ORGANISM: Artificial Sequence
<220> FEATURE:
<223> OTHER INFORMATION: Primer

<400> SEQUENCE: 181
gctcctttya tctgtatcct cagagatcc                               29

<210> SEQ ID NO 182
<211> LENGTH: 28
<212> TYPE: DNA
<213> ORGANISM: Artificial Sequence
<220> FEATURE:
<223> OTHER INFORMATION: Primer

<400> SEQUENCE: 182
tgatcttccc gtcacatact gttgcatg                                28

<210> SEQ ID NO 183
<211> LENGTH: 31
<212> TYPE: DNA
<213> ORGANISM: Artificial Sequence
<220> FEATURE:
<223> OTHER INFORMATION: Primer

<400> SEQUENCE: 183
ggttataaga caatttcttg tacaggarat g                            31

<210> SEQ ID NO 184
<211> LENGTH: 26
<212> TYPE: DNA
<213> ORGANISM: Artificial Sequence
```

```
<220> FEATURE:
<223> OTHER INFORMATION: Primer

<400> SEQUENCE: 184
tttgcaatrt ctcccaccat rgcata                                    26

<210> SEQ ID NO 185
<211> LENGTH: 26
<212> TYPE: DNA
<213> ORGANISM: Artificial Sequence
<220> FEATURE:
<223> OTHER INFORMATION: Primer

<400> SEQUENCE: 185
atgacttttg argtsgaycc catgga                                    26

<210> SEQ ID NO 186
<211> LENGTH: 23
<212> TYPE: DNA
<213> ORGANISM: Artificial Sequence
<220> FEATURE:
<223> OTHER INFORMATION: Primer

<400> SEQUENCE: 186
gccgagaasg gygtrcgsag gta                                       23

<210> SEQ ID NO 187
<211> LENGTH: 25
<212> TYPE: DNA
<213> ORGANISM: Artificial Sequence
<220> FEATURE:
<223> OTHER INFORMATION: Primer

<400> SEQUENCE: 187
agggaaarat agtcaaatca gtcga                                     25

<210> SEQ ID NO 188
<211> LENGTH: 22
<212> TYPE: DNA
<213> ORGANISM: Artificial Sequence
<220> FEATURE:
<223> OTHER INFORMATION: Primer

<400> SEQUENCE: 188
cagttatccc tgcayacaca tg                                        22

<210> SEQ ID NO 189
<211> LENGTH: 25
<212> TYPE: DNA
<213> ORGANISM: Artificial Sequence
<220> FEATURE:
<223> OTHER INFORMATION: Primer

<400> SEQUENCE: 189
agggaaarat agtcaaatca gtcga                                     25

<210> SEQ ID NO 190
<211> LENGTH: 22
<212> TYPE: DNA
<213> ORGANISM: Artificial Sequence
<220> FEATURE:
<223> OTHER INFORMATION: Primer

<400> SEQUENCE: 190
cagttatccc tgcayacaca tg                                        22
```

<210> SEQ ID NO 191
<211> LENGTH: 26
<212> TYPE: DNA
<213> ORGANISM: Artificial Sequence
<220> FEATURE:
<223> OTHER INFORMATION: Primer

<400> SEQUENCE: 191
gaagggtcma acatctgytt aacaag                                    26

<210> SEQ ID NO 192
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (18)..(18)
<223> OTHER INFORMATION: n is inosine

<400> SEQUENCE: 192
gctwgtggga araaaganac tgatcctg                                  28

<210> SEQ ID NO 193
<211> LENGTH: 20
<212> TYPE: DNA
<213> ORGANISM: Artificial Sequence
<220> FEATURE:
<223> OTHER INFORMATION: Primer

<400> SEQUENCE: 193
cggcccctga atgyggctaa                                           20

<210> SEQ ID NO 194
<211> LENGTH: 21
<212> TYPE: DNA
<213> ORGANISM: Artificial Sequence
<220> FEATURE:
<223> OTHER INFORMATION: Primer

<400> SEQUENCE: 194
gaaacacgga cacccaaagt a                                         21

<210> SEQ ID NO 195
<211> LENGTH: 26
<212> TYPE: DNA
<213> ORGANISM: Artificial Sequence
<220> FEATURE:
<223> OTHER INFORMATION: Primer

<400> SEQUENCE: 195
atgggttggg attatccaaa atgtga                                    26

<210> SEQ ID NO 196
<211> LENGTH: 25
<212> TYPE: DNA
<213> ORGANISM: Artificial Sequence
<220> FEATURE:
<223> OTHER INFORMATION: Primer

<400> SEQUENCE: 196
agcagttgta gcatcaccgg atgat                                     25

<210> SEQ ID NO 197
<211> LENGTH: 26

<212> TYPE: DNA
<213> ORGANISM: Artificial Sequence
<220> FEATURE:
<223> OTHER INFORMATION: Primer

<400> SEQUENCE: 197
atgggttggg attatcctaa rtgtga              26

<210> SEQ ID NO 198
<211> LENGTH: 26
<212> TYPE: DNA
<213> ORGANISM: Artificial Sequence
<220> FEATURE:
<223> OTHER INFORMATION: Primer

<400> SEQUENCE: 198
gcagtagttg catcaccact rctagt              26

<210> SEQ ID NO 199
<211> LENGTH: 26
<212> TYPE: DNA
<213> ORGANISM: Artificial Sequence
<220> FEATURE:
<223> OTHER INFORMATION: Primer

<400> SEQUENCE: 199
atgggttggg attatcccaa atgtga              26

<210> SEQ ID NO 200
<211> LENGTH: 23
<212> TYPE: DNA
<213> ORGANISM: Artificial Sequence
<220> FEATURE:
<223> OTHER INFORMATION: Primer

<400> SEQUENCE: 200
gctgtactag crtcaccaga agt                 23

<210> SEQ ID NO 201
<211> LENGTH: 26
<212> TYPE: DNA
<213> ORGANISM: Artificial Sequence
<220> FEATURE:
<223> OTHER INFORMATION: Primer

<400> SEQUENCE: 201
atgggatggg actatcctaa gtgtga              26

<210> SEQ ID NO 202
<211> LENGTH: 23
<212> TYPE: DNA
<213> ORGANISM: Artificial Sequence
<220> FEATURE:
<223> OTHER INFORMATION: Primer

<400> SEQUENCE: 202
gctgtagttg catcaccaga agt                 23

<210> SEQ ID NO 203
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: variation
<222> LOCATION: (13)..(13)

<223> OTHER INFORMATION: n can be any nucleic acid base

<400> SEQUENCE: 203
gccccartgg kcntacatgc acatc                                          25

<210> SEQ ID NO 204
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (6)..(6)
<223> OTHER INFORMATION: n is inosine

<400> SEQUENCE: 204
gccacngtgg grttyctraa ctt                                            23

<210> SEQ ID NO 205
<211> LENGTH: 21
<212> TYPE: DNA
<213> ORGANISM: Artificial Sequence
<220> FEATURE:
<223> OTHER INFORMATION: Primer

<400> SEQUENCE: 205
cackcccagg aartgacgta t                                              21

<210> SEQ ID NO 206
<211> LENGTH: 22
<212> TYPE: DNA
<213> ORGANISM: Artificial Sequence
<220> FEATURE:
<223> OTHER INFORMATION: Primer

<400> SEQUENCE: 206
ccagagatgt tcactcgccg ga                                             22

<210> SEQ ID NO 207
<211> LENGTH: 27
<212> TYPE: DNA
<213> ORGANISM: Artificial Sequence
<220> FEATURE:
<223> OTHER INFORMATION: Primer

<400> SEQUENCE: 207
gagtcttcta acmgaggtcg aaacgta                                        27

<210> SEQ ID NO 208
<211> LENGTH: 18
<212> TYPE: DNA
<213> ORGANISM: Artificial Sequence
<220> FEATURE:
<223> OTHER INFORMATION: Primer

<400> SEQUENCE: 208
gggcacggtg agcgtraa                                                  18

<210> SEQ ID NO 209
<211> LENGTH: 26
<212> TYPE: DNA
<213> ORGANISM: Artificial Sequence
<220> FEATURE:
<223> OTHER INFORMATION: Primer

<400> SEQUENCE: 209
tcaacagaca ctgtagacac agtact                                        26

<210> SEQ ID NO 210
<211> LENGTH: 25
<212> TYPE: DNA
<213> ORGANISM: Artificial Sequence
<220> FEATURE:
<223> OTHER INFORMATION: Primer

<400> SEQUENCE: 210
gtttcccgtt atgcttgtct tctag                                         25

<210> SEQ ID NO 211
<211> LENGTH: 20
<212> TYPE: DNA
<213> ORGANISM: Artificial Sequence
<220> FEATURE:
<223> OTHER INFORMATION: Primer

<400> SEQUENCE: 211
atggcatcag ttggctaaca                                               20

<210> SEQ ID NO 212
<211> LENGTH: 17
<212> TYPE: DNA
<213> ORGANISM: Artificial Sequence
<220> FEATURE:
<223> OTHER INFORMATION: Primer

<400> SEQUENCE: 212
acagccactg ccccatt                                                  17

<210> SEQ ID NO 213
<211> LENGTH: 21
<212> TYPE: DNA
<213> ORGANISM: Artificial Sequence
<220> FEATURE:
<223> OTHER INFORMATION: Primer

<400> SEQUENCE: 213
ggaatagccc ccctacaatt g                                             21

<210> SEQ ID NO 214
<211> LENGTH: 22
<212> TYPE: DNA
<213> ORGANISM: Artificial Sequence
<220> FEATURE:
<223> OTHER INFORMATION: Primer

<400> SEQUENCE: 214
aattcgcatt ctgggtttcc ta                                            22

<210> SEQ ID NO 215
<211> LENGTH: 21
<212> TYPE: DNA
<213> ORGANISM: Artificial Sequence
<220> FEATURE:
<223> OTHER INFORMATION: Primer

<400> SEQUENCE: 215
cctttttgtt gaacgcagca a                                             21

<210> SEQ ID NO 216
<211> LENGTH: 23
<212> TYPE: DNA

```
<213> ORGANISM: Artificial Sequence
<220> FEATURE:
<223> OTHER INFORMATION: Primer

<400> SEQUENCE: 216
cggatgaggc aactagtgac cta                                              23

<210> SEQ ID NO 217
<211> LENGTH: 20
<212> TYPE: DNA
<213> ORGANISM: Artificial Sequence
<220> FEATURE:
<223> OTHER INFORMATION: Primer

<400> SEQUENCE: 217
gccgaatgat gcmatmaayt                                                  20

<210> SEQ ID NO 218
<211> LENGTH: 20
<212> TYPE: DNA
<213> ORGANISM: Artificial Sequence
<220> FEATURE:
<223> OTHER INFORMATION: Primer

<400> SEQUENCE: 218
cgcacccatt ggagtttgac                                                  20

<210> SEQ ID NO 219
<211> LENGTH: 23
<212> TYPE: DNA
<213> ORGANISM: Artificial Sequence
<220> FEATURE:
<223> OTHER INFORMATION: Primer

<400> SEQUENCE: 219
tggtttagct tcggggcrtc atg                                              23

<210> SEQ ID NO 220
<211> LENGTH: 24
<212> TYPE: DNA
<213> ORGANISM: Artificial Sequence
<220> FEATURE:
<223> OTHER INFORMATION: Primer

<400> SEQUENCE: 220
aatrgtgcac ygcatgtttc crtt                                             24

<210> SEQ ID NO 221
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (6)..(6)
<223> OTHER INFORMATION: n is inosine

<400> SEQUENCE: 221
tgcatnggyy accartcaac                                                  20

<210> SEQ ID NO 222
<211> LENGTH: 23
<212> TYPE: DNA
<213> ORGANISM: Artificial Sequence
<220> FEATURE:
<223> OTHER INFORMATION: Primer
```

<400> SEQUENCE: 222
gttgcacaya rcatyccatt gtg                                          23

<210> SEQ ID NO 223
<211> LENGTH: 22
<212> TYPE: DNA
<213> ORGANISM: Artificial Sequence
<220> FEATURE:
<223> OTHER INFORMATION: Primer

<400> SEQUENCE: 223
aatgtgayga ycartgcatg ga                                           22

<210> SEQ ID NO 224
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (17)..(17)
<223> OTHER INFORMATION: n is inosine

<400> SEQUENCE: 224
gagatgaggc racagtngaa ta                                           22

<210> SEQ ID NO 225
<211> LENGTH: 24
<212> TYPE: DNA
<213> ORGANISM: Artificial Sequence
<220> FEATURE:
<223> OTHER INFORMATION: Primer

<400> SEQUENCE: 225
attcagacag gatggaaccg tyaa                                         24

<210> SEQ ID NO 226
<211> LENGTH: 26
<212> TYPE: DNA
<213> ORGANISM: Artificial Sequence
<220> FEATURE:
<223> OTHER INFORMATION: Primer

<400> SEQUENCE: 226
gatactaagc tttgttgtga cctcat                                       26

<210> SEQ ID NO 227
<211> LENGTH: 26
<212> TYPE: DNA
<213> ORGANISM: Artificial Sequence
<220> FEATURE:
<223> OTHER INFORMATION: Primer

<400> SEQUENCE: 227
acccgattrg argctttcag acaaga                                       26

<210> SEQ ID NO 228
<211> LENGTH: 22
<212> TYPE: DNA
<213> ORGANISM: Artificial Sequence
<220> FEATURE:
<223> OTHER INFORMATION: Primer

<400> SEQUENCE: 228
ctgttgrgac cgcatgattg ac                                    22

<210> SEQ ID NO 229
<211> LENGTH: 20
<212> TYPE: DNA
<213> ORGANISM: Artificial Sequence
<220> FEATURE:
<223> OTHER INFORMATION: Primer

<400> SEQUENCE: 229
cggcccctga atgyggctaa                                       20

<210> SEQ ID NO 230
<211> LENGTH: 21
<212> TYPE: DNA
<213> ORGANISM: Artificial Sequence
<220> FEATURE:
<223> OTHER INFORMATION: Primer

<400> SEQUENCE: 230
gaaacacgga cacccaaagt a                                     21

<210> SEQ ID NO 231
<211> LENGTH: 21
<212> TYPE: DNA
<213> ORGANISM: Artificial Sequence
<220> FEATURE:
<223> OTHER INFORMATION: Primer

<400> SEQUENCE: 231
aaaggcatgc aagacgctat g                                     21

<210> SEQ ID NO 232
<211> LENGTH: 25
<212> TYPE: DNA
<213> ORGANISM: Artificial Sequence
<220> FEATURE:
<223> OTHER INFORMATION: Primer

<400> SEQUENCE: 232
tgttaagaac gtctttcatt tgctg                                 25

<210> SEQ ID NO 233
<211> LENGTH: 21
<212> TYPE: DNA
<213> ORGANISM: Artificial Sequence
<220> FEATURE:
<223> OTHER INFORMATION: Primer

<400> SEQUENCE: 233
cctttcgtgg cagttgggtc a                                     21

<210> SEQ ID NO 234
<211> LENGTH: 21
<212> TYPE: DNA
<213> ORGANISM: Artificial Sequence
<220> FEATURE:
<223> OTHER INFORMATION: Primer

<400> SEQUENCE: 234
actgagcttg atccgcccac a                                     21

<210> SEQ ID NO 235
<211> LENGTH: 22
<212> TYPE: DNA
<213> ORGANISM: Artificial Sequence
<220> FEATURE:
<223> OTHER INFORMATION: Primer

<400> SEQUENCE: 235
caagggctat aaaggcgttg ct                                          22

<210> SEQ ID NO 236
<211> LENGTH: 25
<212> TYPE: DNA
<213> ORGANISM: Artificial Sequence
<220> FEATURE:
<223> OTHER INFORMATION: Primer

<400> SEQUENCE: 236
catgataatt gatggtcgca gactt                                       25

<210> SEQ ID NO 237
<211> LENGTH: 20
<212> TYPE: DNA
<213> ORGANISM: Artificial Sequence
<220> FEATURE:
<223> OTHER INFORMATION: Primer

<400> SEQUENCE: 237
aatttcatcg ttcccggcag                                             20

<210> SEQ ID NO 238
<211> LENGTH: 20
<212> TYPE: DNA
<213> ORGANISM: Artificial Sequence
<220> FEATURE:
<223> OTHER INFORMATION: Primer

<400> SEQUENCE: 238
gccgcgttta ctaatcccca                                             20

<210> SEQ ID NO 239
<211> LENGTH: 23
<212> TYPE: DNA
<213> ORGANISM: Artificial Sequence
<220> FEATURE:
<223> OTHER INFORMATION: Primer

<400> SEQUENCE: 239
gcactatgtg ggaaggtgct tca                                         23

<210> SEQ ID NO 240
<211> LENGTH: 18
<212> TYPE: DNA
<213> ORGANISM: Artificial Sequence
<220> FEATURE:
<223> OTHER INFORMATION: Primer

<400> SEQUENCE: 240
ctgcgcggat gctaatgg                                               18

<210> SEQ ID NO 241
<211> LENGTH: 23
<212> TYPE: DNA
<213> ORGANISM: Artificial Sequence
<220> FEATURE:
<223> OTHER INFORMATION: Primer

<400> SEQUENCE: 241
gcactatgtg ggaaggtgct tca                                         23

<210> SEQ ID NO 242
<211> LENGTH: 21
<212> TYPE: DNA
<213> ORGANISM: Artificial Sequence
<220> FEATURE:
<223> OTHER INFORMATION: Primer

<400> SEQUENCE: 242
gtagtatcct gcgcggatgc t                                              21

<210> SEQ ID NO 243
<211> LENGTH: 26
<212> TYPE: DNA
<213> ORGANISM: Artificial Sequence
<220> FEATURE:
<223> OTHER INFORMATION: Primer

<400> SEQUENCE: 243
tggcactacc cctctccgta ttcacg                                         26

<210> SEQ ID NO 244
<211> LENGTH: 22
<212> TYPE: DNA
<213> ORGANISM: Artificial Sequence
<220> FEATURE:
<223> OTHER INFORMATION: Primer

<400> SEQUENCE: 244
gtacgggcga ccccacgatg ac                                             22

<210> SEQ ID NO 245
<211> LENGTH: 19
<212> TYPE: DNA
<213> ORGANISM: Artificial Sequence
<220> FEATURE:
<223> OTHER INFORMATION: Primer

<400> SEQUENCE: 245
agatttggac ctgcgagcg                                                 19

<210> SEQ ID NO 246
<211> LENGTH: 20
<212> TYPE: DNA
<213> ORGANISM: Artificial Sequence
<220> FEATURE:
<223> OTHER INFORMATION: Primer

<400> SEQUENCE: 246
gagcggctgt ctccacaagt                                                20

<210> SEQ ID NO 247
<211> LENGTH: 17
<212> TYPE: DNA
<213> ORGANISM: Artificial Sequence
<220> FEATURE:
<223> OTHER INFORMATION: Probe

<400> SEQUENCE: 247
ctggtgcart tygcccg                                                   17

<210> SEQ ID NO 248
<211> LENGTH: 20
<212> TYPE: DNA
<213> ORGANISM: Artificial Sequence
<220> FEATURE:
<223> OTHER INFORMATION: Probe

<400> SEQUENCE: 248
caggaygcyt cggartacct                                        20

<210> SEQ ID NO 249
<211> LENGTH: 21
<212> TYPE: DNA
<213> ORGANISM: Artificial Sequence
<220> FEATURE:
<223> OTHER INFORMATION: Probe
<220> FEATURE:
<221> NAME/KEY: variation
<222> LOCATION: (14)..(14)
<223> OTHER INFORMATION: n can be any nucleic acid base

<400> SEQUENCE: 249
ccaygcttgt ggancttatg c                                      21

<210> SEQ ID NO 250
<211> LENGTH: 20
<212> TYPE: DNA
<213> ORGANISM: Artificial Sequence
<220> FEATURE:
<223> OTHER INFORMATION: Probe

<400> SEQUENCE: 250
ttycccattc cattcattgt                                        20

<210> SEQ ID NO 251
<211> LENGTH: 18
<212> TYPE: DNA
<213> ORGANISM: Artificial Sequence
<220> FEATURE:
<223> OTHER INFORMATION: Probe

<400> SEQUENCE: 251
cccwgtgttt gcagtrga                                          18

<210> SEQ ID NO 252
<211> LENGTH: 17
<212> TYPE: DNA
<213> ORGANISM: Artificial Sequence
<220> FEATURE:
<223> OTHER INFORMATION: Probe

<400> SEQUENCE: 252
taggaccacg ggatgca                                           17

<210> SEQ ID NO 253
<211> LENGTH: 21
<212> TYPE: DNA
<213> ORGANISM: Artificial Sequence
<220> FEATURE:
<223> OTHER INFORMATION: Probe

<400> SEQUENCE: 253
aagttgtcct cgctgccact c                                      21

<210> SEQ ID NO 254
<211> LENGTH: 18
<212> TYPE: DNA
<213> ORGANISM: Artificial Sequence
<220> FEATURE:
<223> OTHER INFORMATION: Probe

<400> SEQUENCE: 254

-continued cagtgcccgc gacggacg                                          18

<210> SEQ ID NO 255
<211> LENGTH: 15
<212> TYPE: DNA
<213> ORGANISM: Artificial Sequence
<220> FEATURE:
<223> OTHER INFORMATION: Probe

<400> SEQUENCE: 255
tggtttagct tcggg                                             15

<210> SEQ ID NO 256
<211> LENGTH: 25
<212> TYPE: DNA
<213> ORGANISM: Artificial Sequence
<220> FEATURE:
<223> OTHER INFORMATION: Primer

<400> SEQUENCE: 256
gggcaaatat ggaracatac gtgaa                                  25

<210> SEQ ID NO 257
<211> LENGTH: 29
<212> TYPE: DNA
<213> ORGANISM: Artificial Sequence
<220> FEATURE:
<223> OTHER INFORMATION: Primer

<400> SEQUENCE: 257 tcttttttcta rgacattgta ytgaacagc                             29

<210> SEQ ID NO 258
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: variation
<222> LOCATION: (3)..(3)
<223> OTHER INFORMATION: n can be any nucleic acid base
<220> FEATURE:
<221> NAME/KEY: modified_base
<222> LOCATION: (18)..(18)
<223> OTHER INFORMATION: n is inosine

<400> SEQUENCE: 258
gtnaaactga gyagyggnta caarga                                 26

<210> SEQ ID NO 259
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (4)..(4)
<223> OTHER INFORMATION: n is inosine
<220> FEATURE:
<221> NAME/KEY: modified_base
<222> LOCATION: (10)..(10)
<223> OTHER INFORMATION: n is inosine
<220> FEATURE:
<221> NAME/KEY: modified_base
<222> LOCATION: (12)..(12)
<223> OTHER INFORMATION: n is inosine

<400> SEQUENCE: 259

```
ggcnagaagn anraarcatg aygcc                                              25
```

<210> SEQ ID NO 260
<211> LENGTH: 15
<212> TYPE: DNA
<213> ORGANISM: Artificial Sequence
<220> FEATURE:
<223> OTHER INFORMATION: Primer

<400> SEQUENCE: 260

```
ggaracatac gtgaa                                                         15
```

<210> SEQ ID NO 261
<211> LENGTH: 15
<212> TYPE: DNA
<213> ORGANISM: Artificial Sequence
<220> FEATURE:
<223> OTHER INFORMATION: Primer

<400> SEQUENCE: 261

```
attgtaytga acagc                                                         15
```

<210> SEQ ID NO 262
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (7)..(7)
<223> OTHER INFORMATION: n is inosine

<400> SEQUENCE: 262

```
yagyggntac aarga                                                         15
```

<210> SEQ ID NO 263
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (2)..(2)
<223> OTHER INFORMATION: n is inosine

<400> SEQUENCE: 263

```
anraarcatg aygcc                                                         15
```

<210> SEQ ID NO 264
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (9)..(9)
<223> OTHER INFORMATION: n is inosine

<400> SEQUENCE: 264

```
cartggkcnt acatgcayat ckc                                                23
```

<210> SEQ ID NO 265
<211> LENGTH: 20
<212> TYPE: DNA

```
<213> ORGANISM: Artificial Sequence
<220> FEATURE:
<223> OTHER INFORMATION: Primer

<400> SEQUENCE: 265
gcrcgggcra aytgcaccag                                                20

<210> SEQ ID NO 266
<211> LENGTH: 20
<212> TYPE: DNA
<213> ORGANISM: Artificial Sequence
<220> FEATURE:
<223> OTHER INFORMATION: Primer

<400> SEQUENCE: 266
gcgcgggcaa actgcacgag                                                20

<210> SEQ ID NO 267
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)..(1)
<223> OTHER INFORMATION: n is inosine

<400> SEQUENCE: 267
ntacatgcay atckc                                                     15

<210> SEQ ID NO 268
<211> LENGTH: 15
<212> TYPE: DNA
<213> ORGANISM: Artificial Sequence
<220> FEATURE:
<223> OTHER INFORMATION: Primer

<400> SEQUENCE: 268
ggcraaytgc accag                                                     15

<210> SEQ ID NO 269
<211> LENGTH: 15
<212> TYPE: DNA
<213> ORGANISM: Artificial Sequence
<220> FEATURE:
<223> OTHER INFORMATION: Primer

<400> SEQUENCE: 269
ggcaaactgc acgag                                                     15

<210> SEQ ID NO 270
<211> LENGTH: 21
<212> TYPE: DNA
<213> ORGANISM: Artificial Sequence
<220> FEATURE:
<223> OTHER INFORMATION: Primer

<400> SEQUENCE: 270
ggtggyagat ggcgtrccat a                                              21

<210> SEQ ID NO 271
<211> LENGTH: 27
<212> TYPE: DNA
<213> ORGANISM: Artificial Sequence
<220> FEATURE:
<223> OTHER INFORMATION: Primer
```

<400> SEQUENCE: 271
tctracaaac ttactagagg atggctg                              27

<210> SEQ ID NO 272
<211> LENGTH: 15
<212> TYPE: DNA
<213> ORGANISM: Artificial Sequence
<220> FEATURE:
<223> OTHER INFORMATION: Primer

<400> SEQUENCE: 272
agatggcgtr ccata                                           15

<210> SEQ ID NO 273
<211> LENGTH: 15
<212> TYPE: DNA
<213> ORGANISM: Artificial Sequence
<220> FEATURE:
<223> OTHER INFORMATION: Primer

<400> SEQUENCE: 273
actagaggat ggctg                                           15

<210> SEQ ID NO 274
<211> LENGTH: 24
<212> TYPE: DNA
<213> ORGANISM: Artificial Sequence
<220> FEATURE:
<223> OTHER INFORMATION: Primer

<400> SEQUENCE: 274
atggtytcag ctatgaacac agca                                 24

<210> SEQ ID NO 275
<211> LENGTH: 24
<212> TYPE: DNA
<213> ORGANISM: Artificial Sequence
<220> FEATURE:
<223> OTHER INFORMATION: Primer

<400> SEQUENCE: 275
tgccagyttt tggacgtctt ctcc                                 24

<210> SEQ ID NO 276
<211> LENGTH: 15
<212> TYPE: DNA
<213> ORGANISM: Artificial Sequence
<220> FEATURE:
<223> OTHER INFORMATION: Primer

<400> SEQUENCE: 276
gctatgaaca cagca                                           15

<210> SEQ ID NO 277
<211> LENGTH: 15
<212> TYPE: DNA
<213> ORGANISM: Artificial Sequence
<220> FEATURE:
<223> OTHER INFORMATION: Primer

<400> SEQUENCE: 277
ttggacgtct tctcc                                           15

<210> SEQ ID NO 278

```
<211> LENGTH: 26
<212> TYPE: DNA
<213> ORGANISM: Artificial Sequence
<220> FEATURE:
<223> OTHER INFORMATION: Primer

<400> SEQUENCE: 278
cgaacgggtg agtaacacgt gggtga                                          26

<210> SEQ ID NO 279
<211> LENGTH: 25
<212> TYPE: DNA
<213> ORGANISM: Artificial Sequence
<220> FEATURE:
<223> OTHER INFORMATION: Primer

<400> SEQUENCE: 279
ctcatcccac accgctaaag cgctt                                           25

<210> SEQ ID NO 280
<211> LENGTH: 15
<212> TYPE: DNA
<213> ORGANISM: Artificial Sequence
<220> FEATURE:
<223> OTHER INFORMATION: Primer

<400> SEQUENCE: 280
gtaacacgtg ggtga                                                      15

<210> SEQ ID NO 281
<211> LENGTH: 15
<212> TYPE: DNA
<213> ORGANISM: Artificial Sequence
<220> FEATURE:
<223> OTHER INFORMATION: Primer

<400> SEQUENCE: 281
accgctaaag cgctt                                                      15

<210> SEQ ID NO 282
<211> LENGTH: 25
<212> TYPE: DNA
<213> ORGANISM: Artificial Sequence
<220> FEATURE:
<223> OTHER INFORMATION: Primer

<400> SEQUENCE: 282
gacgggcctc ttcgtcrtac gcaat                                           25

<210> SEQ ID NO 283
<211> LENGTH: 23
<212> TYPE: DNA
<213> ORGANISM: Artificial Sequence
<220> FEATURE:
<223> OTHER INFORMATION: Primer

<400> SEQUENCE: 283
gagtgctagg tcgggacggt gag                                             23

<210> SEQ ID NO 284
<211> LENGTH: 15
<212> TYPE: DNA
<213> ORGANISM: Artificial Sequence
<220> FEATURE:
<223> OTHER INFORMATION: Primer

<400> SEQUENCE: 284
```

```
ttcgtcrtac gcaat                                                       15

<210> SEQ ID NO 285
<211> LENGTH: 15
<212> TYPE: DNA
<213> ORGANISM: Artificial Sequence
<220> FEATURE:
<223> OTHER INFORMATION: Primer

<400> SEQUENCE: 285
ggtcgggacg gtgag                                                       15

<210> SEQ ID NO 286
<211> LENGTH: 18
<212> TYPE: DNA
<213> ORGANISM: Artificial Sequence
<220> FEATURE:
<223> OTHER INFORMATION: Probe

<400> SEQUENCE: 286
cacgarggct ccacrtac                                                    18

<210> SEQ ID NO 287
<211> LENGTH: 10
<212> TYPE: DNA
<213> ORGANISM: Artificial Sequence
<220> FEATURE:
<223> OTHER INFORMATION: Probe
<220> FEATURE:
<221> NAME/KEY: modified_base
<222> LOCATION: (9)..(9)
<223> OTHER INFORMATION: n is inosine

<400> SEQUENCE: 287 ggcaatgcng                                                             10

<210> SEQ ID NO 288
<211> LENGTH: 10
<212> TYPE: DNA
<213> ORGANISM: Artificial Sequence
<220> FEATURE:
<223> OTHER INFORMATION: Probe

<400> SEQUENCE: 288
ggcaatgcag                                                             10

<210> SEQ ID NO 289
<211> LENGTH: 10
<212> TYPE: DNA
<213> ORGANISM: Artificial Sequence
<220> FEATURE:
<223> OTHER INFORMATION: Probe

<400> SEQUENCE: 289
ggcaatgctg                                                             10

<210> SEQ ID NO 290
<211> LENGTH: 10
<212> TYPE: DNA
<213> ORGANISM: Artificial Sequence
<220> FEATURE:
<223> OTHER INFORMATION: Probe

<400> SEQUENCE: 290 aggcaatgcw                                                             10
```

```
<210> SEQ ID NO 291
<211> LENGTH: 13
<212> TYPE: DNA
<213> ORGANISM: Artificial Sequence
<220> FEATURE:
<223> OTHER INFORMATION: Probe

<400> SEQUENCE: 291
gcaatgcwgc wcc                                                      13

<210> SEQ ID NO 292
<211> LENGTH: 10
<212> TYPE: DNA
<213> ORGANISM: Artificial Sequence
<220> FEATURE:
<223> OTHER INFORMATION: Probe

<400> SEQUENCE: 292 gayggraccr                                                          10

<210> SEQ ID NO 293
<211> LENGTH: 10
<212> TYPE: DNA
<213> ORGANISM: Artificial Sequence
<220> FEATURE:
<223> OTHER INFORMATION: Probe

<400> SEQUENCE: 293 gayrggaccr                                                          10

<210> SEQ ID NO 294
<211> LENGTH: 10
<212> TYPE: DNA
<213> ORGANISM: Artificial Sequence
<220> FEATURE:
<223> OTHER INFORMATION: Probe

<400> SEQUENCE: 294 gatgggaccr                                                          10

<210> SEQ ID NO 295
<211> LENGTH: 10
<212> TYPE: DNA
<213> ORGANISM: Artificial Sequence
<220> FEATURE:
<223> OTHER INFORMATION: Probe

<400> SEQUENCE: 295 gacgggaccr                                                          10

<210> SEQ ID NO 296
<211> LENGTH: 10
<212> TYPE: DNA
<213> ORGANISM: Artificial Sequence
<220> FEATURE:
<223> OTHER INFORMATION: Probe

<400> SEQUENCE: 296 gaygggaccg                                                          10

<210> SEQ ID NO 297
<211> LENGTH: 10
<212> TYPE: DNA
<213> ORGANISM: Artificial Sequence
<220> FEATURE:
<223> OTHER INFORMATION: Probe
```

```
<400> SEQUENCE: 297 gayggacca                                                              10

<210> SEQ ID NO 298
<211> LENGTH: 10
<212> TYPE: DNA
<213> ORGANISM: Artificial Sequence
<220> FEATURE:
<223> OTHER INFORMATION: Probe

<400> SEQUENCE: 298 aygggaccra                                                             10

<210> SEQ ID NO 299
<211> LENGTH: 10
<212> TYPE: DNA
<213> ORGANISM: Artificial Sequence
<220> FEATURE:
<223> OTHER INFORMATION: Probe

<400> SEQUENCE: 299 ggaygggacc                                                             10

<210> SEQ ID NO 300
<211> LENGTH: 10
<212> TYPE: DNA
<213> ORGANISM: Artificial Sequence
<220> FEATURE:
<223> OTHER INFORMATION: Probe
<220> FEATURE:
<221> NAME/KEY: modified_base
<222> LOCATION: (10)..(10)
<223> OTHER INFORMATION: n is inosine

<400> SEQUENCE: 300 gaygggaccn                                                             10

<210> SEQ ID NO 301
<211> LENGTH: 10
<212> TYPE: DNA
<213> ORGANISM: Artificial Sequence
<220> FEATURE:
<223> OTHER INFORMATION: Probe
<220> FEATURE:
<221> NAME/KEY: modified_base
<222> LOCATION: (3)..(3)
<223> OTHER INFORMATION: n is inosine

<400> SEQUENCE: 301 gangggaccr                                                             10

<210> SEQ ID NO 302
<211> LENGTH: 10
<212> TYPE: DNA
<213> ORGANISM: Artificial Sequence
<220> FEATURE:
<223> OTHER INFORMATION: Probe

<400> SEQUENCE: 302
accagacaca                                                             10

<210> SEQ ID NO 303
<211> LENGTH: 10
<212> TYPE: DNA
<213> ORGANISM: Artificial Sequence
<220> FEATURE:
```

```
<223> OTHER INFORMATION: Probe

<400> SEQUENCE: 303
gcaccagaca                                                          10

<210> SEQ ID NO 304
<211> LENGTH: 10
<212> TYPE: DNA
<213> ORGANISM: Artificial Sequence
<220> FEATURE:
<223> OTHER INFORMATION: Probe
<220> FEATURE:
<221> NAME/KEY: modified_base
<222> LOCATION: (4)..(4)
<223> OTHER INFORMATION: n is inosine

<400> SEQUENCE: 304 cacnagacac                                                          10

<210> SEQ ID NO 305
<211> LENGTH: 10
<212> TYPE: DNA
<213> ORGANISM: Artificial Sequence
<220> FEATURE:
<223> OTHER INFORMATION: Probe
<220> FEATURE:
<221> NAME/KEY: modified_base
<222> LOCATION: (8)..(8)
<223> OTHER INFORMATION: n is inosine

<400> SEQUENCE: 305 caccaganac                                                          10

<210> SEQ ID NO 306
<211> LENGTH: 10
<212> TYPE: DNA
<213> ORGANISM: Artificial Sequence
<220> FEATURE:
<223> OTHER INFORMATION: Probe

<400> SEQUENCE: 306 caccwgacac                                                          10

<210> SEQ ID NO 307
<211> LENGTH: 10
<212> TYPE: DNA
<213> ORGANISM: Artificial Sequence
<220> FEATURE:
<223> OTHER INFORMATION: Probe

<400> SEQUENCE: 307 caccagacwc                                                          10

<210> SEQ ID NO 308
<211> LENGTH: 10
<212> TYPE: DNA
<213> ORGANISM: Artificial Sequence
<220> FEATURE:
<223> OTHER INFORMATION: Probe

<400> SEQUENCE: 308 caccaracac                                                          10

<210> SEQ ID NO 309
<211> LENGTH: 10
<212> TYPE: DNA
<213> ORGANISM: Artificial Sequence
```

```
<220> FEATURE:
<223> OTHER INFORMATION: Probe

<400> SEQUENCE: 309 ggtcatyggr                                                              10

<210> SEQ ID NO 310
<211> LENGTH: 10
<212> TYPE: DNA
<213> ORGANISM: Artificial Sequence
<220> FEATURE:
<223> OTHER INFORMATION: Probe

<400> SEQUENCE: 310
ggtcattggg                                                              10

<210> SEQ ID NO 311
<211> LENGTH: 10
<212> TYPE: DNA
<213> ORGANISM: Artificial Sequence
<220> FEATURE:
<223> OTHER INFORMATION: Probe

<400> SEQUENCE: 311
ggtcattgga                                                              10

<210> SEQ ID NO 312
<211> LENGTH: 10
<212> TYPE: DNA
<213> ORGANISM: Artificial Sequence
<220> FEATURE:
<223> OTHER INFORMATION: Probe

<400> SEQUENCE: 312 gtcattggrg                                                              10

<210> SEQ ID NO 313
<211> LENGTH: 10
<212> TYPE: DNA
<213> ORGANISM: Artificial Sequence
<220> FEATURE:
<223> OTHER INFORMATION: Probe

<400> SEQUENCE: 313
tggtcattgg                                                              10

<210> SEQ ID NO 314
<211> LENGTH: 10
<212> TYPE: DNA
<213> ORGANISM: Artificial Sequence
<220> FEATURE:
<223> OTHER INFORMATION: Probe

<400> SEQUENCE: 314 ggtcatcggr                                                              10

<210> SEQ ID NO 315
<211> LENGTH: 10
<212> TYPE: DNA
<213> ORGANISM: Artificial Sequence
<220> FEATURE:
<223> OTHER INFORMATION: Probe

<400> SEQUENCE: 315 rgtcattggr                                                              10
```

```
<210> SEQ ID NO 316
<211> LENGTH: 10
<212> TYPE: DNA
<213> ORGANISM: Artificial Sequence
<220> FEATURE:
<223> OTHER INFORMATION: Probe

<400> SEQUENCE: 316 agtcattggr                                                            10

<210> SEQ ID NO 317
<211> LENGTH: 10
<212> TYPE: DNA
<213> ORGANISM: Artificial Sequence
<220> FEATURE:
<223> OTHER INFORMATION: Probe
<220> FEATURE:
<221> NAME/KEY: modified_base
<222> LOCATION: (4)..(4)
<223> OTHER INFORMATION: n is inosine

<400> SEQUENCE: 317 ggtnattggr                                                            10

<210> SEQ ID NO 318
<211> LENGTH: 10
<212> TYPE: DNA
<213> ORGANISM: Artificial Sequence
<220> FEATURE:
<223> OTHER INFORMATION: Probe
<220> FEATURE:
<221> NAME/KEY: modified_base
<222> LOCATION: (8)..(8)
<223> OTHER INFORMATION: n is inosine

<400> SEQUENCE: 318 ggtcattngr                                                            10

<210> SEQ ID NO 319
<211> LENGTH: 10
<212> TYPE: DNA
<213> ORGANISM: Artificial Sequence
<220> FEATURE:
<223> OTHER INFORMATION: Probe

<400> SEQUENCE: 319
actgggcacg                                                            10

<210> SEQ ID NO 320
<211> LENGTH: 10
<212> TYPE: DNA
<213> ORGANISM: Artificial Sequence
<220> FEATURE:
<223> OTHER INFORMATION: Probe

<400> SEQUENCE: 320
tcactgggca                                                            10

<210> SEQ ID NO 321
<211> LENGTH: 10
<212> TYPE: DNA
<213> ORGANISM: Artificial Sequence
<220> FEATURE:
<223> OTHER INFORMATION: Probe

<400> SEQUENCE: 321 crctgggcac                                                            10
```

```
<210> SEQ ID NO 322
<211> LENGTH: 10
<212> TYPE: DNA
<213> ORGANISM: Artificial Sequence
<220> FEATURE:
<223> OTHER INFORMATION: Probe

<400> SEQUENCE: 322
cgctgggcac                                                                10

<210> SEQ ID NO 323
<211> LENGTH: 10
<212> TYPE: DNA
<213> ORGANISM: Artificial Sequence
<220> FEATURE:
<223> OTHER INFORMATION: Probe
<220> FEATURE:
<221> NAME/KEY: modified_base
<222> LOCATION: (8)..(8)
<223> OTHER INFORMATION: n is inosine

<400> SEQUENCE: 323 cactgggnac                                                                10

<210> SEQ ID NO 324
<211> LENGTH: 10
<212> TYPE: DNA
<213> ORGANISM: Artificial Sequence
<220> FEATURE:
<223> OTHER INFORMATION: Probe
<220> FEATURE:
<221> NAME/KEY: modified_base
<222> LOCATION: (3)..(3)
<223> OTHER INFORMATION: n is inosine

<400> SEQUENCE: 324 cantgggcac                                                                10

<210> SEQ ID NO 325
<211> LENGTH: 10
<212> TYPE: DNA
<213> ORGANISM: Artificial Sequence
<220> FEATURE:
<223> OTHER INFORMATION: Probe

<400> SEQUENCE: 325 cactggrcac                                                                10

<210> SEQ ID NO 326
<211> LENGTH: 10
<212> TYPE: DNA
<213> ORGANISM: Artificial Sequence
<220> FEATURE:
<223> OTHER INFORMATION: Probe

<400> SEQUENCE: 326 cactrggcac                                                                10

<210> SEQ ID NO 327
<211> LENGTH: 10
<212> TYPE: DNA
<213> ORGANISM: Artificial Sequence
<220> FEATURE:
<223> OTHER INFORMATION: Probe

<400> SEQUENCE: 327 cacygggcac                                                                10
```

```
<210> SEQ ID NO 328
<211> LENGTH: 10
<212> TYPE: DNA
<213> ORGANISM: Artificial Sequence
<220> FEATURE:
<223> OTHER INFORMATION: Probe

<400> SEQUENCE: 328 grgtgttcat                                                                 10

<210> SEQ ID NO 329
<211> LENGTH: 10
<212> TYPE: DNA
<213> ORGANISM: Artificial Sequence
<220> FEATURE:
<223> OTHER INFORMATION: Probe

<400> SEQUENCE: 329
gtgttcattt                                                                 10

<210> SEQ ID NO 330
<211> LENGTH: 10
<212> TYPE: DNA
<213> ORGANISM: Artificial Sequence
<220> FEATURE:
<223> OTHER INFORMATION: Probe

<400> SEQUENCE: 330
agtgttcatt                                                                 10

<210> SEQ ID NO 331
<211> LENGTH: 10
<212> TYPE: DNA
<213> ORGANISM: Artificial Sequence
<220> FEATURE:
<223> OTHER INFORMATION: Probe

<400> SEQUENCE: 331
ggtgttcatt                                                                 10

<210> SEQ ID NO 332
<211> LENGTH: 10
<212> TYPE: DNA
<213> ORGANISM: Artificial Sequence
<220> FEATURE:
<223> OTHER INFORMATION: Probe
<220> FEATURE:
<221> NAME/KEY: modified_base
<222> LOCATION: (7)..(7)
<223> OTHER INFORMATION: n is inosine

<400> SEQUENCE: 332 rgtgttnatt                                                                 10

<210> SEQ ID NO 333
<211> LENGTH: 10
<212> TYPE: DNA
<213> ORGANISM: Artificial Sequence
<220> FEATURE:
<223> OTHER INFORMATION: Probe

<400> SEQUENCE: 333 rgtrttcatt                                                                 10

<210> SEQ ID NO 334
<211> LENGTH: 10
<212> TYPE: DNA
```

```
<213> ORGANISM: Artificial Sequence
<220> FEATURE:
<223> OTHER INFORMATION: Probe

<400> SEQUENCE: 334 rgtgttcawt                                                              10

<210> SEQ ID NO 335
<211> LENGTH: 10
<212> TYPE: DNA
<213> ORGANISM: Artificial Sequence
<220> FEATURE:
<223> OTHER INFORMATION: Probe

<400> SEQUENCE: 335 rgtgtwcatt                                                              10

<210> SEQ ID NO 336
<211> LENGTH: 10
<212> TYPE: DNA
<213> ORGANISM: Artificial Sequence
<220> FEATURE:
<223> OTHER INFORMATION: Probe

<400> SEQUENCE: 336 rgtgttcwtt                                                              10

<210> SEQ ID NO 337
<211> LENGTH: 10
<212> TYPE: DNA
<213> ORGANISM: Artificial Sequence
<220> FEATURE:
<223> OTHER INFORMATION: Probe
<220> FEATURE:
<221> NAME/KEY: modified_base
<222> LOCATION: (3)..(3)
<223> OTHER INFORMATION: n is inosine

<400> SEQUENCE: 337 rgngttcatt                                                              10

<210> SEQ ID NO 338
<211> LENGTH: 10
<212> TYPE: DNA
<213> ORGANISM: Artificial Sequence
<220> FEATURE:
<223> OTHER INFORMATION: Probe

<400> SEQUENCE: 338 gtgcarttyg                                                              10

<210> SEQ ID NO 339
<211> LENGTH: 10
<212> TYPE: DNA
<213> ORGANISM: Artificial Sequence
<220> FEATURE:
<223> OTHER INFORMATION: Probe

<400> SEQUENCE: 339 ygcytcggar                                                              10

<210> SEQ ID NO 340
<211> LENGTH: 10
<212> TYPE: DNA
<213> ORGANISM: Artificial Sequence
<220> FEATURE:
<223> OTHER INFORMATION: Probe
```

```
<220> FEATURE:
<221> NAME/KEY: variation
<222> LOCATION: (9)..(9)
<223> OTHER INFORMATION: n can be any nucleic acid base

<400> SEQUENCE: 340 cttgtgganc                                                            10

<210> SEQ ID NO 341
<211> LENGTH: 10
<212> TYPE: DNA
<213> ORGANISM: Artificial Sequence
<220> FEATURE:
<223> OTHER INFORMATION: Probe

<400> SEQUENCE: 341
cattccattc                                                            10

<210> SEQ ID NO 342
<211> LENGTH: 10
<212> TYPE: DNA
<213> ORGANISM: Artificial Sequence
<220> FEATURE:
<223> OTHER INFORMATION: Probe

<400> SEQUENCE: 342 wgtgtttgca                                                            10

<210> SEQ ID NO 343
<211> LENGTH: 10
<212> TYPE: DNA
<213> ORGANISM: Artificial Sequence
<220> FEATURE:
<223> OTHER INFORMATION: Probe

<400> SEQUENCE: 343
accacgggat                                                            10

<210> SEQ ID NO 344
<211> LENGTH: 10
<212> TYPE: DNA
<213> ORGANISM: Artificial Sequence
<220> FEATURE:
<223> OTHER INFORMATION: Probe

<400> SEQUENCE: 344
gtcctcgctg                                                            10

<210> SEQ ID NO 345
<211> LENGTH: 10
<212> TYPE: DNA
<213> ORGANISM: Artificial Sequence
<220> FEATURE:
<223> OTHER INFORMATION: Probe

<400> SEQUENCE: 345
gcccgcgacg                                                            10
```